United States Patent
Brown et al.

(10) Patent No.: US 9,932,317 B2
(45) Date of Patent: Apr. 3, 2018

(54) QUINAZOLINE COMPOUNDS AND THEIR USE IN THERAPY

(71) Applicants: Imperial Innovations Limited, London (GB); Emory University, Atlanta, GA (US)

(72) Inventors: Robert Brown, London (GB); Matthew John Fuchter, London (GB); Nadine Chapman-Rothe, London (GB); Nitipol Srimongkolpithak, London (GB); Joachim Caron, London (GB); James Snyder, Atlanta, GA (US); Thota Ganesh, Atlanta, GA (US); Jin Liu, Atlanta, GA (US); Aiming Sun, Atlanta, GA (US)

(73) Assignees: Imperial Innovations Limited, London (GB); Emory University, Atlanta, GA (US)

( * ) Notice: Subject to any disclaimer, the term of this patent is extended or adjusted under 35 U.S.C. 154(b) by 0 days.

(21) Appl. No.: 14/385,268

(22) PCT Filed: Mar. 19, 2013

(86) PCT No.: PCT/GB2013/050689
§ 371 (c)(1),
(2) Date: Sep. 15, 2014

(87) PCT Pub. No.: WO2013/140148
PCT Pub. Date: Sep. 26, 2013

(65) Prior Publication Data
US 2015/0057263 A1    Feb. 26, 2015

Related U.S. Application Data

(60) Provisional application No. 61/612,694, filed on Mar. 19, 2012.

(51) Int. Cl.
| C07D 401/12 | (2006.01) |
| C07D 401/14 | (2006.01) |
| A61K 31/517 | (2006.01) |
| C07D 239/95 | (2006.01) |
| C07D 405/14 | (2006.01) |
| C07D 491/056 | (2006.01) |
| C07D 403/12 | (2006.01) |
| C07D 401/04 | (2006.01) |
| A61K 31/519 | (2006.01) |
| A61K 31/5377 | (2006.01) |
| A61K 31/55 | (2006.01) |
| A61K 31/551 | (2006.01) |

(52) U.S. Cl.
CPC ......... *C07D 239/95* (2013.01); *A61K 31/517* (2013.01); *A61K 31/519* (2013.01); *A61K 31/5377* (2013.01); *A61K 31/55* (2013.01); *A61K 31/551* (2013.01); *C07D 401/04* (2013.01); *C07D 401/12* (2013.01); *C07D 401/14* (2013.01); *C07D 403/12* (2013.01); *C07D 405/14* (2013.01); *C07D 491/056* (2013.01)

(58) Field of Classification Search
None
See application file for complete search history.

(56) References Cited

U.S. PATENT DOCUMENTS

| 6,156,758 | A | 12/2000 | Kung et al. |
| 7,115,739 | B2 * | 10/2006 | Bebbington ......... C07D 231/12 544/254 |
| 9,458,131 | B2 * | 10/2016 | Yoon .................... A61K 31/517 |
| 2005/0250770 | A1 | 11/2005 | Ono et al. |
| 2009/0312305 | A1 | 12/2009 | Beard et al. |
| 2013/0053397 | A1 | 2/2013 | Brackley, III et al. |
| 2013/0059849 | A1 | 3/2013 | Burgess et al. |

FOREIGN PATENT DOCUMENTS

| JP | 2000281660 A | 10/2000 |
| JP | 2007269629 A | 10/2007 |
| WO | 2005082865 A1 | 9/2005 |

OTHER PUBLICATIONS

Xiang et al. Molecules, vol. 20, pp. 7620-7636 (2015).*
(Continued)

*Primary Examiner* — Emily Bernhardt
(74) *Attorney, Agent, or Firm* — Kilyk & Bowersox, P.L.L.C.

(57) ABSTRACT

This invention relates to quinazoline compounds of Formula (I) which are inhibitors of the histone lysine methyltransferase (HKMTase) EZH2, and to uses of such compounds as medicaments, in particular in the treatment of a disease or disorder in which inhibition of EZH2 provides a therapeutic or prophylactic effect.

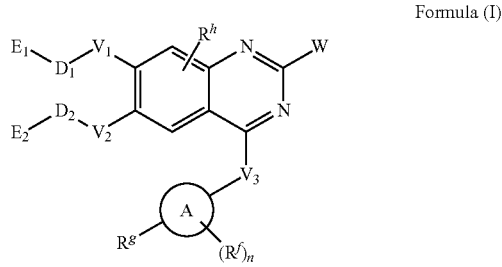

Formula (I)

7 Claims, 19 Drawing Sheets

(56) References Cited

OTHER PUBLICATIONS

Yoon et al. Chemical Abstract vol. 158, No. 704584 (2013) (Abstract for WO 2013070852, May 16, 2013).*
Kubicek et al. PNAS Apr. 3, 2012 vol. 109 No. 14, 34 pages.*
International Search Report issued in corresponding International Patent Application No. PCT/GB2013/050689 dated Jul. 29, 2013 (6 pages).
International Preliminary Report on Patentability issued in corresponding International Patent Application No. PCT/GB2013/050689 dated Sep. 23, 2014 (10 pages).
Liu et al., "Protein Lysine Methyltransferase G9a Inhibitors: Design, Synthesis, and Structure Activity Relationships of 2,4-Diamino-7-aminoalkoxy-quinazolines," Journal of Medicinal Chemistry, Aug. 12, 2010, vol. 53, No. 15, pp. 5844-5857 (42 pages).
Liu et al., "Optimization of Cellular Activity of G9a Inhibitors 7-Aminoalkoxy-quinazolines," Journal of Medicinal Chemistry, Sep. 8, 2011, vol. 54, No. 17, pp. 6139-6150 (29 pages).
Liu et al., "Discovery of a 2,4-Diamino-7-aminoalkoxy-quinazoline as a Potent and Selective Inhibitor of Histone Lysine Methyltransferase G9a," Journal of Medicinal Chemistry, Dec. 24, 2009, vol. 52, No. 24, pp. 7950-7953 (21 pages).
Chang et al., "Adding a Lysine Mimic in the Design of Potent Inhibitors of Histone Lysine Methyltransferases," Journal of Molecular Biology, Jul. 2, 2010, vol. 400, No. 1, pp. 1-7 (9 pages).
Kubicek et al., "Reversal of H3K9me2 by a Small-Molecule Inhibitor for the G9a Histone Methyltransferase," Molecular Cell, vol. 25, No. 3, Feb. 9, 2007, pp. 473-481.
European Examination Report issued in corresponding European Patent Application No. 13721004.3 dated Feb. 21, 2017 (7 pages).
Decarlo et al., "Oncoepigenomics: Making histone lysine methylation count," European Journal of Medicinal Chemistry 56, 2012, pp. 179-194.
Jones, P., "Development of second generation epigenetic agents," Med. Chem. Commun., 2012, 3, pp. 135-161.
Zagni et al., "Histone Methyltransferase Inhibitors: Novel Epigenetic Agents for Cancer Treatment," Current Medicinal Chemistry, 2013, 20, pp. 167-185.

* cited by examiner

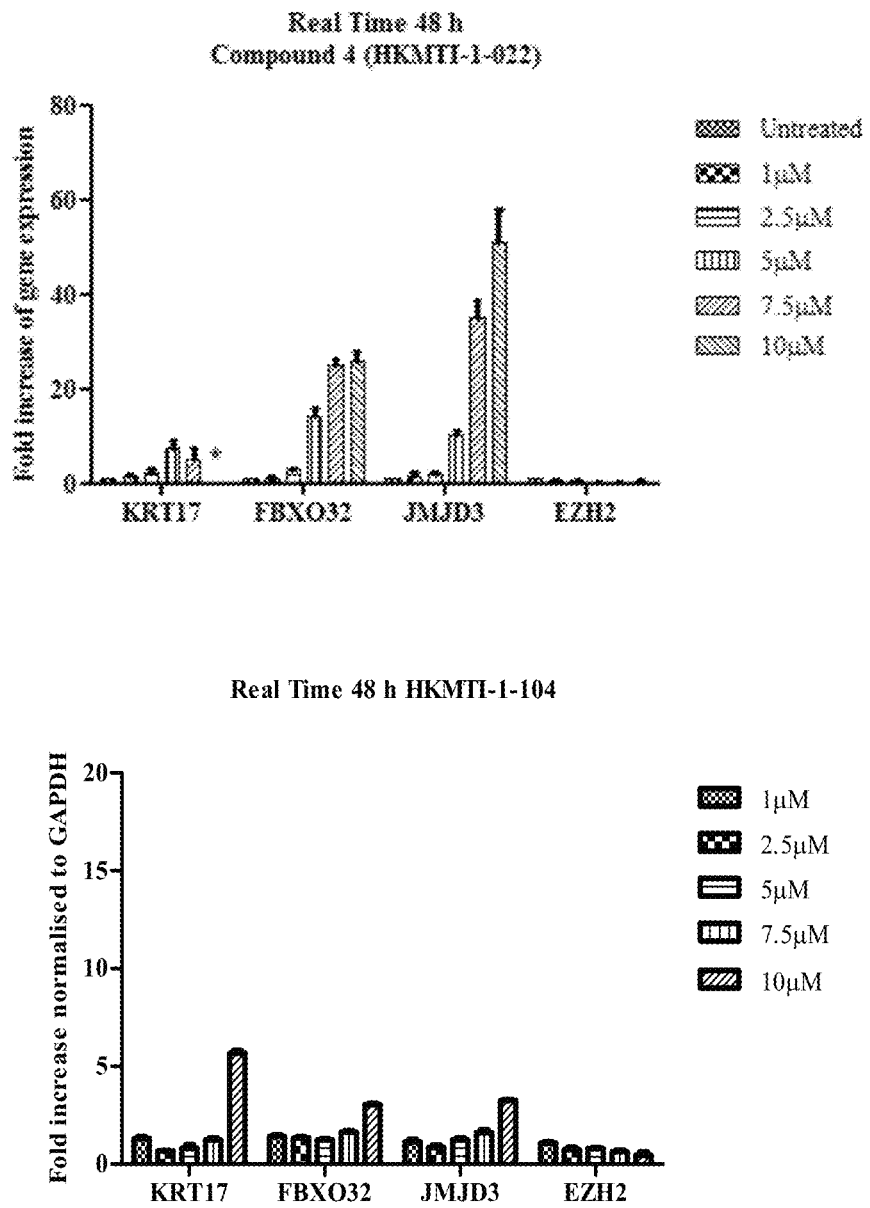
Figure 1(d)(contd)

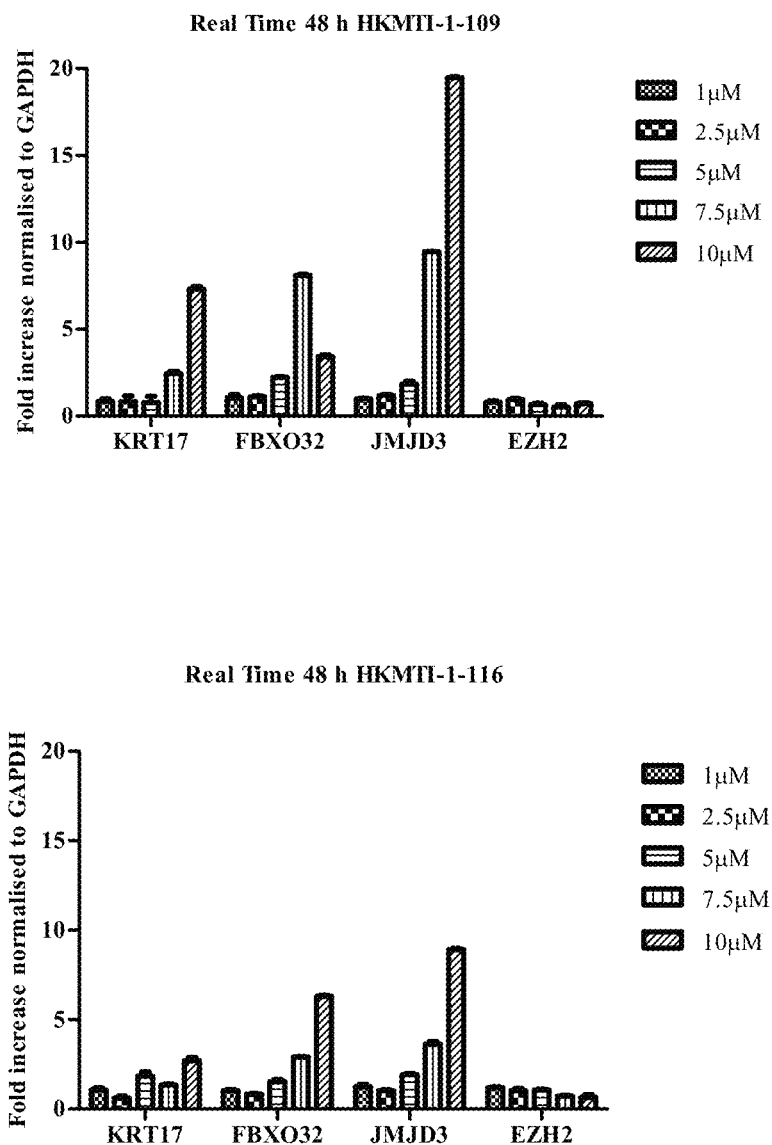
Figure 1(d) (contd)

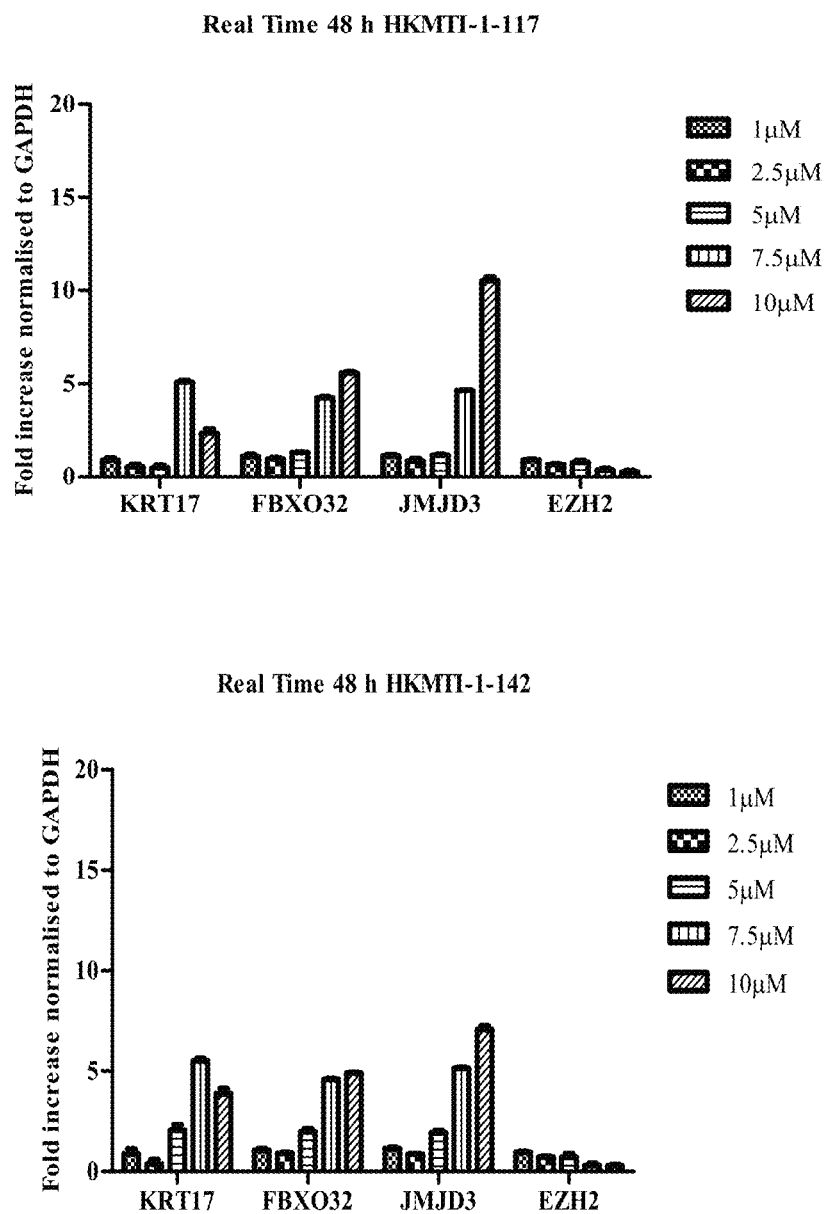
Figure 1(d)(contd)

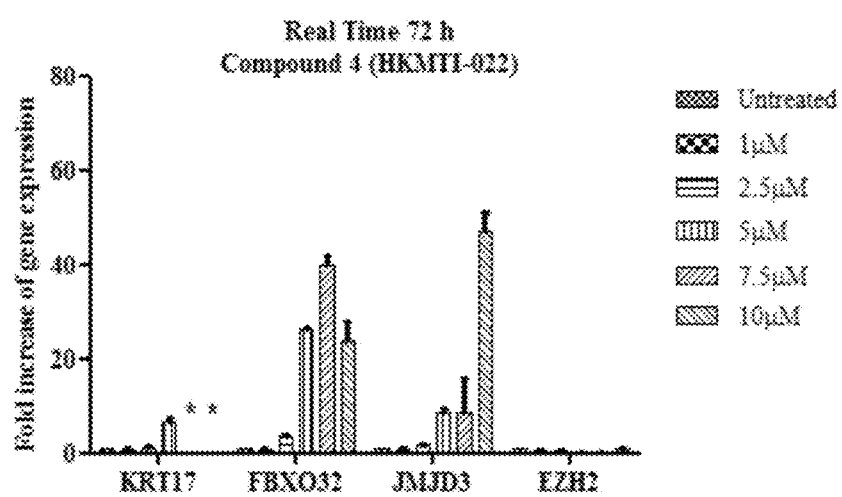
Figure 1(e)(contd)

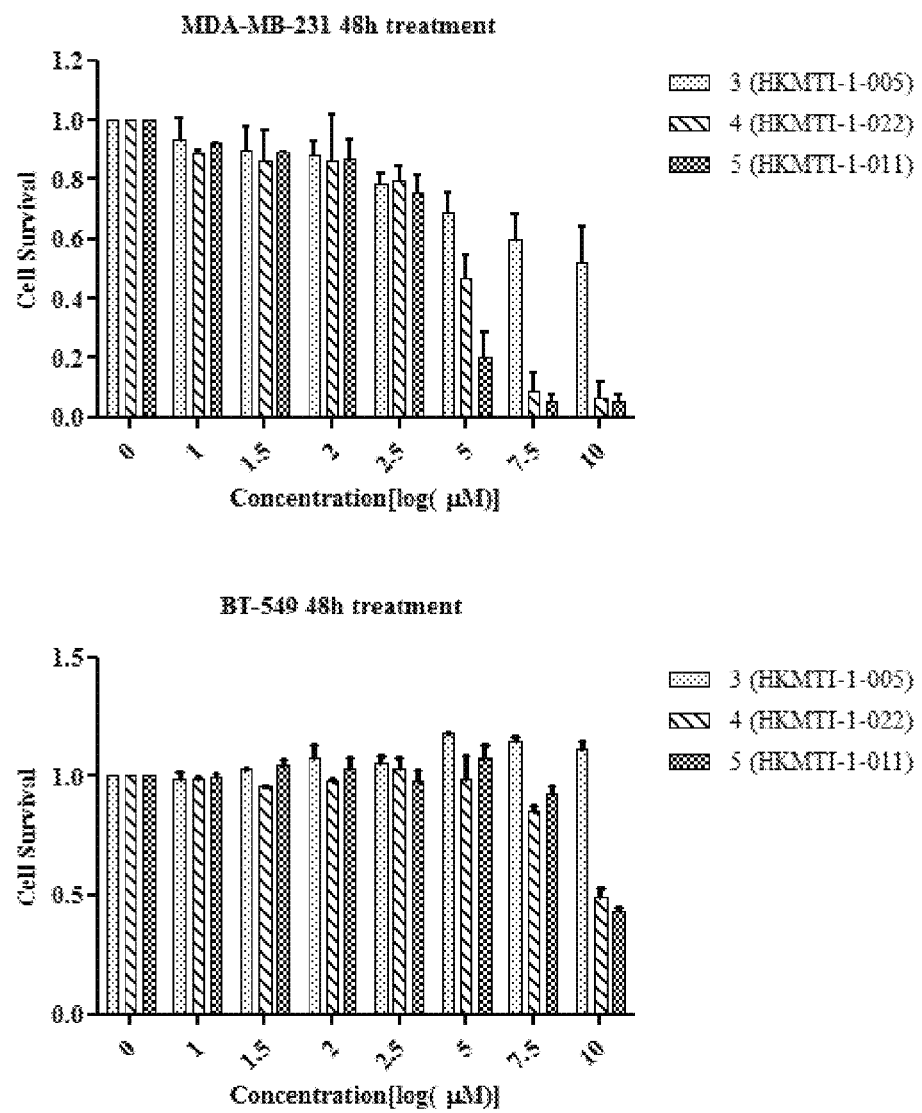
Figure 3(a) (contd)

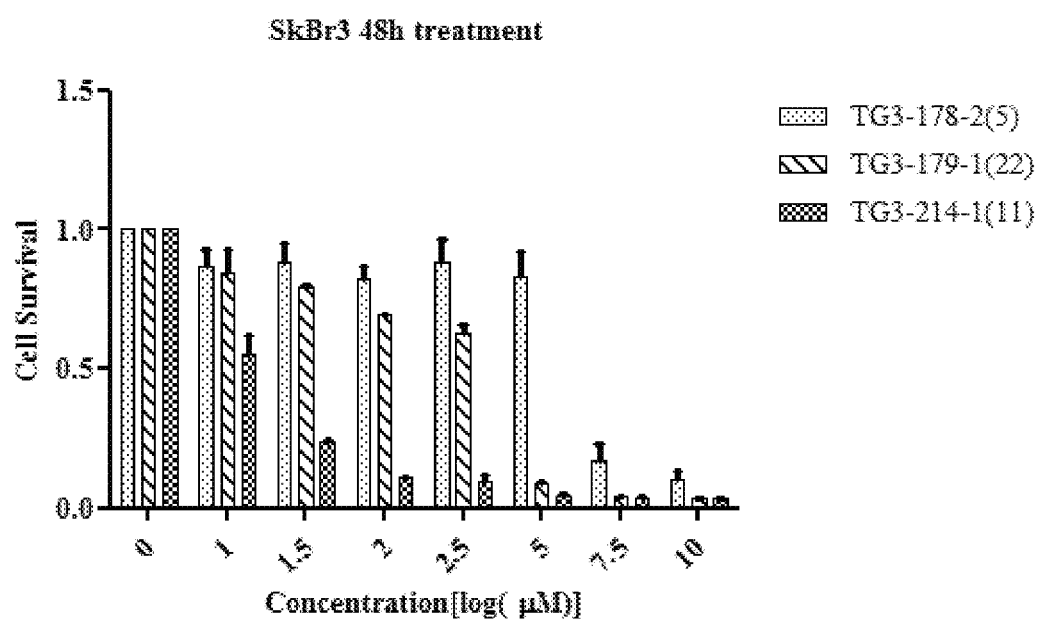
Figure 3(a) (contd)

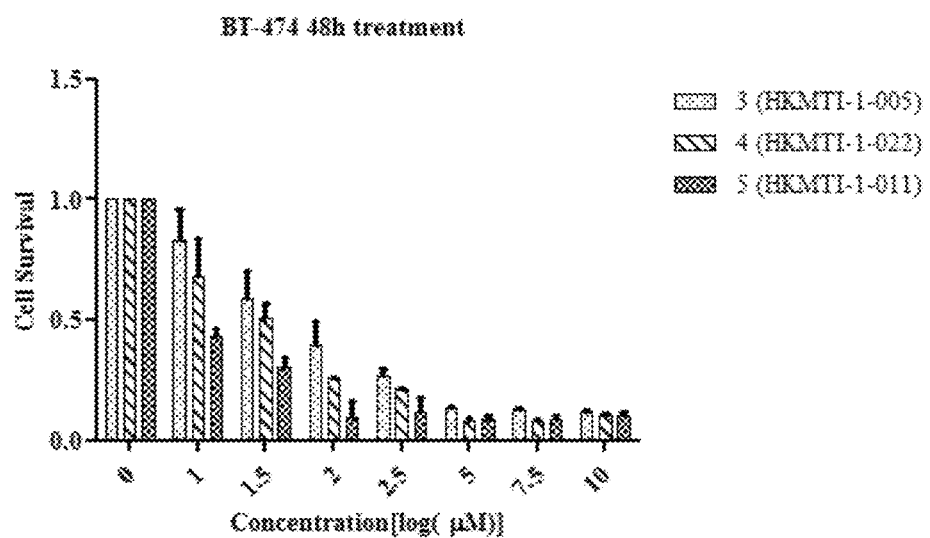
Figure 3(a) (contd)

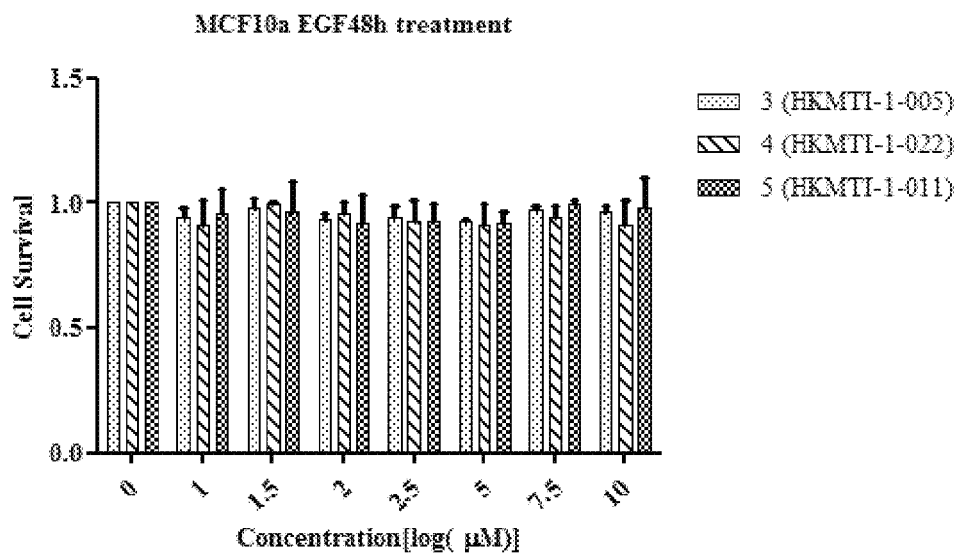
Figure 3(a) (contd)
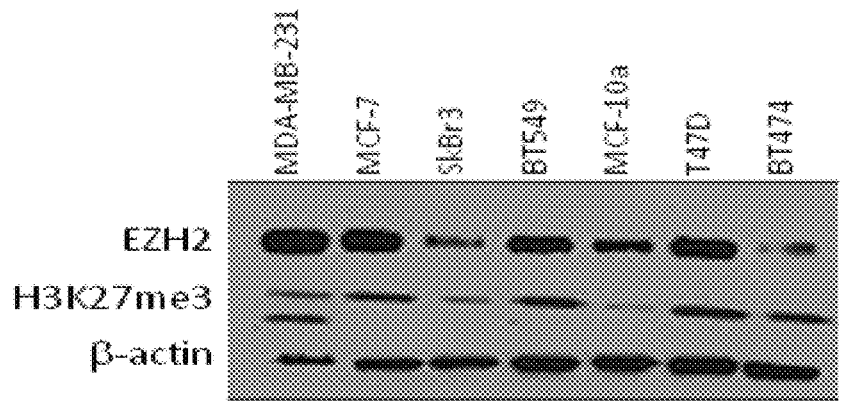
Figure 3(b)

Table 1: Effects on gene expression of compounds in cell-based screen

|  | Compound | KRT17 | FBXO32 | JMJD3 | EZH2 |
|---|---|---|---|---|---|
| G9a inhibitor | BIX01294 | 1.1 | 3.3 | 2.7 | 0.9 |
| G9a inhibitor | UNC0224 | 1.3 | 1.0 | 1.6 | 0.6 |
| Hit | HKMTI-1-005 | 4.1 | 3.7 | 3.1 | 0.6 |
| Hit | HKMTI-1-022 | 4.3 | 29.4 | 11.6 | 0.2 |
| Hit | HKMTI-1-011 | 7.0 | 33.3 | 6.3 | 0.2 |
| Hit | HKMTI-1-067 | 1.27 | 5.88 | 2.45 | 0.70 |
| Hit | HKMTI-1-069 | 1.25 | 4.74 | 2.05 | 0.55 |
| Hit | HKMTI-1-070 | 1.37 | 5.24 | 3.86 | 0.29 |
| Hit | HKMTI-1-076 | 2.21 | 7.21 | 1.03 | 0.56 |
| Hit | HKMTI-1-080 | 1.46 | 4.06 | 2.79 | 0.67 |
| Hit | HKMTI-1-083 | 1.42 | 4.66 | 0.80 | 0.39 |
| Hit | HKMTI-1-091 | 3.18 | 4.86 | 4.46 | 0.13 |
| Hit | HKMTI-1-093 | 5.87 | 5.73 | 7.97 | 0.58 |
| Hit | HKMTI-1-095 | 1.88 | 4.06 | 2.26 | 0.89 |
| Hit | HKMTI-1-104 | 2.65 | 2.20 | 2.28 | 0.54 |
| Hit | HKMTI-1-108 | 4.76 | 3.82 | 3.24 | 0.21 |
| Hit | HKMTI-1-109 | 6.52 | 9.19 | 4.31 | 0.38 |
| Hit | HKMTI-1-116 | 2.64 | 4.30 | 2.63 | 0.45 |
| Hit | HKMTI-1-117 | 5.95 | 4.65 | 3.90 | 0.38 |
| Hit | HKMTI-1-142 | 6.80 | 12.76 | 5.19 | 0.72 |
| Negative control | HKMTI-1-012 | 0.7 | 1.1 | 1.6 | 0.9 |

Figure 4

Table 2. Numbers of genes significantly changing in gene expression following compound treatment

| Compound | Time | Number of up-regulated genes | Number of up-regulated EZH2 targets | Number of down-regulated genes | Number of down-regulated EZH2 targets |
|---|---|---|---|---|---|
| HKMTI-1-005 | 24h | 1047 | 71 | 1021 | 78 |
| HKMTI-1-005 | 48h | 1108 | 58 | 1075 | 104 |
| HKMTI-1-012 | 24h | 407 | 27 | 359 | 29 |
| HKMTI-1-012 | 48h | 2 | 0 | 11 | 0 |

Figure 5

Supplementary Table1: Primers for quantitative PCR

| Name of gene | forward | reverse | Product | Pub med REF |
|---|---|---|---|---|
| GAPDH_1 | CCTGTTCGACAGTCAGCCG | CGACCAAATCCGTTGAC TCC | 101bp | 12615718 |
| GAPDH_2 | CCCCTTCATTGACCTCAACT ACAT | CGCTCCTGGAAGATGGT GA | 135bp | PMC2517635 |
| KRT17 | CAACACTGAGCTGGAAGTCA | GCTGGCTGTGAGGATCT TGT | 124bp | |
| FBXO32 | TGTTGCAGCCAAGAAGAGAA | CAATATCCATGGCGCTC TTT | 120bp | Primer 3 |
| JMJD3 | CCTGAAATCCATCACAGT | GTGCCTGTCAGATCCCA GTT | | |
| EZH2 | AGTGTGACCCTGACCTCTGT | AGATGGTGCCAGCAATA GAT | 122bp | RTPrimerDB probe ID: 4521 |
| RUNX2 | CAGAAGCTGGAGGACCAGAC | TGGGAGAATGGGTTCAG TTC | | |
| RUNX3 | TTCCTAACTGTTGGCTTTCC | TAGGTGCTTTCCTGGGT TTA | 95bp | RTPrimerDB probe ID: 4757 |

Figure 6

Supplementary Table 2

| Name | forward | reverse | Product |
|---|---|---|---|
| ChIP_Upstr_FBXO32 | TTTCTCCACTCCCAACCTG | GCCCCTTAGCTGTCACTAACC | 117bp |
| ChIP_Ex1_FBXO32 | GGGCAGAACTGGGTGAAGAC | CTGAGGTCGCTCACGAAACT | 80bp |
| ChIP_Intr1_FBXO32_1 | AGAACACCTGGTCCCTCTGA | CTCCGGTGTCCTTAAAGCAG | 111bp |
| ChIP_Intr1_FBXO32_2 | CCTGCCACCTTTGGTTAAAA | CATCCAAGCAACGACTGGTA | 116bp |
| ChIP_Intr1_FBXO32_3 | GGAGTGAGATCATGGGAGGA | CACTTGCCATTCCCCTTCTA | 95bp |
| | | | |
| ChIP_KRT17_UTR1 | TGGCATTGATGAGTGAGAGG | AGCCGAGAGACATTCCTCAA | |
| ChIP_KRT17_Ex1 | GCTGCTACAGCTTTGGCTCT | TCACCTCCAGCTCAGTGTTG | |
| ChIP_KRT17_Int1-2_2 | GGGGACATTTTCCCATTCTT | CTTGCCCCGTGCTGTATTAT | |
| ChIP_KRT17_Int3-4 | CCTTAGAGGGCTTCCCTGTC | CGTGGGAGGTTCCTTGTGTA | |
| ChIP_KRT17_publ | AACCCATTTCCCCACCAGACAGG | AAATCCTCGTGCTGAGTGCCG | |
| | | | |
| ChIP_RUNX_Prom1_UTR | AAAAAGAGAGGTAGCCACAA | AGTGTCAACCCAACCTCAGC | |
| ChIP_RUNX_Ex1 | ACAGCCAACCAAGTGAATCC | GGAAGGAGTCGAAGATGCTG | |
| ChIP_RUNX_Int1 | AAGAGGGGTTGGTGGTCTCT | CTGCCCTTTGAGGTCTTGAG | |
| ChIP_RUNX_Int2 | GCCCTGCAGCAGGAATGACTTT | TCCGCACCAACGTCTCTAC | |
| ChIP_RUNX_Ex3 | GGGAAGGAGGTTGAAAGAGG | TCACCTCCTCAAAGCGATCT | |
| | | | |
| GAPDH_NEW_ChIP | CACCGTCAAGGCTGAGAACG | ATACCCAAGGGAGCCACACC | 134bp |
| | | | |
| Beta-globin_ChIP | GCTGGTGGTCTACCCTTGGA | AGGTTGTCCAGGTGAGCCAG | 150bp |

Supplementary Table 3

| Product Name | Target Sequence | Manufacturer and Catalog no. |
|---|---|---|
| G9a( HS_BAT8_ 1) | ATCGAGGTGATCCGCATGCTA | QIAGEN SI00091189 |
| G9a( HS_EHMT2_ 1) | CCTCTTCGACTTAGACAACAA | QIAGEN SI03083241 |
| SUV39H1(HS_SUV39H1 _ 6) | CAGGTGTACAACGTCTTCATA | QIAGEN SI02665019 |
| SUV39H1 (HS_SUV39H1_ 4) | ACGGAGGTGGATGCCAGGAAA | QIAGEN SI00048685 |
| EZH2(HS_EZH2_ 4 ) | TTCGAGCTCCTCTGAAGCAAA | QIAGEN SI00063973 |
| EZH2(HS_EZH2 _7) | AACCATGTTTACAACTATCAA | QIAGEN SI02665166 |

QUINAZOLINE COMPOUNDS AND THEIR USE IN THERAPY

This application is a National Stage Application of PCT/GB2013/050689, filed Mar. 19, 2013, which claims the benefit under 35 U.S.C. §119(e) of U.S. Provisional Patent Application No. 61/612,694, filed Mar. 19, 2012, which is incorporated in its entirety by reference herein.

FIELD OF INVENTION

This invention relates to compounds of formula (IA), (IB) and (IC), which are inhibitors of the histone lysine methyltransferase (HKMTase) EZH2, and to uses of such compounds as medicaments, in particular in the treatment of a disease or disorder in which inhibition of EZH2 provides a therapeutic or prophylactic effect. Such diseases include neurodegenerative diseases such as Huntington's disease, viral conditions such as HIV, and cancers, including ovarian cancer, breast cancer, prostate cancer, liver cancer, skin cancer, bladder cancer, head and neck cancer, myelodysplastic syndrome, and solid and multiple haematological tumours (including glioblastoma, renal, esophageal, colon, non-small cell lung, small cell lung, multiple myeloma and chronic myeloid leukaemia tumours).

BACKGROUND TO THE INVENTION

Transcriptional regulation by epigenetic processes has been implicated in the aetiology of many diseases. In cancer, aberrant epigenetic silencing of genes implicated in tumorigenesis and progression has been observed in all tumour types. Epigenetic silencing can be associated with repressive histone marks, such as H3K27me3 (3). The epigenetic H3K27me3 repressive mark is executed and maintained by the polycomb repressive (PRC2) complex via its HKMT catalytic subunit EZH2 (5). EZH2 along with EED and SUZ12 are the indispensible core components of PRC2. Unlike most other epigenetic marks that are mediated by multiple enzymes, the trimethylation of H3K27 appears to be mediated primarily by EZH2 suggesting EZH2 inhibition as a key target for development of epigenetic therapies (6). EZH2 over-expression is a prognostic marker for shorter patient survival for a variety of cancers (9-11). It has been implicated in tumor angiogenesis (12), while mouse models demonstrated its role in driving tumorgenesis (13). Furthermore, maintenance of cancer stem cells seems to depend on EZH2 expression and knock-down of EZH2 in tumour cells blocks tumour cell growth (14-16). Thus, there is strong evidence that inhibition of EZH2 may be useful for the treatment of cancer, and it would be desirable to identify small molecule inhibitors of that target.

Small molecule inhibitors of EZH2 based on indole (A) and azaindazole cores (B) have previously been described, see WO2011/140324 and WO2012/005805.

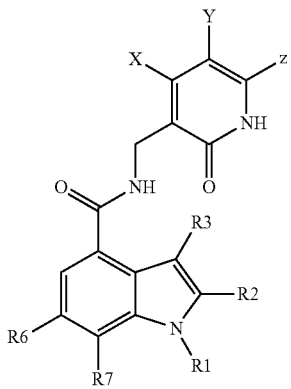

(A)

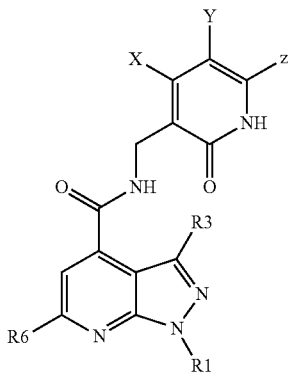

(B)

However, there remains a need for further compounds having useful EZH2 inhibitory effects.

The aminoquinazoline compound BIX-01294 (see structure (C) below) and related compounds have been described as having activity against the protein lysine methyltransferase G9a (see J. Med. Chem. 2011, 54 (17), p. 6139-6150)

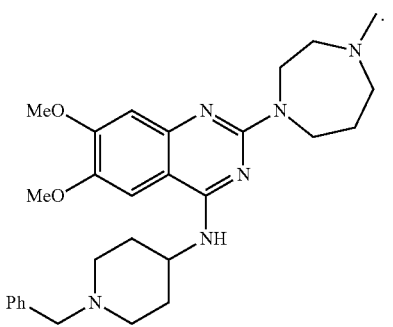

(C)

SUMMARY OF THE INVENTION

The invention provides a compound of formula (IA)

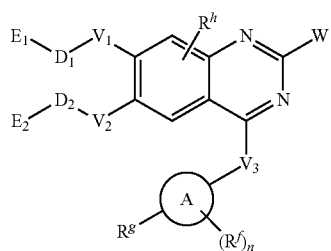

(IA)

or a pharmaceutically acceptable salt thereof;
wherein W is

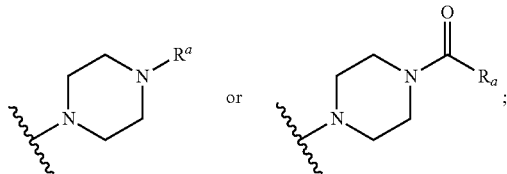

$R^a$ is selected from the group consisting of hydrogen, $C_{1-8}$ alkyl optionally substituted with up to three halogens, $C_{2-8}$ alkenyl optionally substituted with up to three halogens, $C_{2-8}$ alkynyl optionally substituted with up to three halogens, optionally substituted 5 to 10-membered carbocyclyl, optionally substituted 5 to 10-membered heterocyclyl, optionally substituted 5 to 10-membered carbocyclyl-$C_{1-6}$ alkyl and optionally substituted 5 to 10-membered heterocyclyl-$C_{1-6}$ alkyl, said carbocyclyl or heterocyclyl being optionally substituted with up to 3 substituents each independently selected from the group consisting of $OR^1$, $N(R^2)_2$, $SR^3$, —C(O)$C_{1-4}$alkyl, —C(O)$C_{1-4}$-trihaloalkyl, —C(O)O$C_{1-4}$alkyl, —C(O)O$C_{1-4}$-trihaloalkyl, —C(O)NH$_2$, —C(O)NHC$_{1-4}$ alkyl, —C(O)N($C_{1-4}$alkyl)$_2$, —S(O)$C_{1-4}$alkyl, —S(O)$_2$$C_{1-4}$alkyl, —S(O)$_2$NH$_2$, —S(O)$_2$NHC$_{1-4}$alkyl, —S(O)$_2$N($C_{1-4}$alkyl)$_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

each $R^1$ is independently selected from the group consisting of hydrogen, $C_{1-4}$alkyl, $C_{1-4}$trifluoroalkyl, —C(O)$C_{1-4}$alkyl, and —C(O)$C_{1-4}$trihaloalkyl;

each $R^2$ is independently selected from the group consisting of hydrogen, $C_{1-4}$alkyl, $C_{1-4}$trifluoroalkyl, —C(O)$C_{1-4}$alkyl, —C(O)$C_{1-4}$trihaloalkyl, —S(O)$_2$$C_{1-4}$alkyl, and —S(O)$_2$$C_{1-4}$trihaloalkyl;

each $R^3$ is independently selected from the group consisting of hydrogen, $C_{1-4}$alkyl, $C_{1-4}$trifluoroalkyl, —C(O)$C_{1-4}$alkyl, and —C(O)$C_{1-4}$trihaloalkyl;

$V_1$ and $D_1$ are both absent and $E_1$ is hydrogen or halogen; or $V_1$ is selected from the group consisting of $NR^c$, O or S;

$D_1$ is absent or selected from the group consisting of optionally substituted $C_{1-8}$ alkylene, optionally substituted $C_{2-8}$ alkenylene and optionally substituted $C_{2-8}$ alkynylene, said $C_{1-8}$ alkylene, $C_{2-8}$ alkenylene or $C_{2-8}$ alkynylene being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NHC$_{1-4}$alkyl, —C(O)N($C_{1-4}$alkyl)$_2$, —S(O)$C_{1-4}$alkyl, —S(O)$_2$$C_{1-4}$alkyl, —S(O)$_2$NH$_2$, —S(O)$_2$NHC$_{1-4}$alkyl, —S(O)$_2$N($C_{1-4}$alkyl)$_2$, halogen, nitro and cyano;

$E_1$ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NHC$_{1-4}$alkyl, —C(O)N($C_{1-4}$alkyl)$_2$, —S(O)$C_{1-4}$alkyl, —S(O)$_2$$C_{1-4}$alkyl, —S(O)$_2$NH$_2$, —S(O)$_2$NHC$_{1-4}$alkyl, —S(O)$_2$N($C_{1-4}$alkyl)$_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

$V_2$ and $D_2$ are both absent and $E_2$ is hydrogen or halogen; or $V_2$ is selected from the group consisting of $NR^c$, O or S;

$D_2$ is absent or selected from the group consisting of optionally substituted $C_{1-8}$ alkylene, optionally substituted $C_{2-8}$ alkenylene and optionally substituted $C_{2-8}$ alkynylene, said $C_{1-8}$ alkylene, $C_{2-8}$ alkenylene or $C_{2-8}$ alkynylene being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NHC$_{1-4}$alkyl, —C(O)N($C_{1-4}$alkyl)$_2$, —S(O)$C_{1-4}$alkyl, —S(O)$_2$$C_{1-4}$alkyl, —S(O)$_2$NH$_2$, —S(O)$_2$NHC$_{1-4}$alkyl, —S(O)$_2$N($C_{1-4}$alkyl)$_2$, halogen, nitro and cyano;

$E_2$ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NHC$_{1-4}$alkyl, C(O)N($C_{1-4}$alkyl)$_2$, —S(O)$C_{1-4}$alkyl, —S(O)$_2$$C_{1-4}$alkyl, —S(O)$_2$NH$_2$, —S(O)$_2$NHC$_{1-4}$alkyl, —S(O)$_2$N($C_{1-4}$alkyl)$_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

each $R^c$ is independently selected from the group consisting of hydrogen and $C_{1-6}$ alkyl;

or wherein $V_1$ and $V_2$ are each independently selected from the group consisting of $NR^c$, O or S, $E_1$ and $E_2$ are both absent, and $D_1$ and $D_2$ together form a linker group between $V_1$ and $V_2$, said linker comprising optionally substituted $C_{1-4}$ alkylene, and said alkylene being optionally substituted with 1 or 2 substituents each independently selected from the group consisting of halogen, cyano and $OR^1$;

$V_3$ is $NR^e$, O or S;

$R^e$ is hydrogen or $C_{1-6}$ alkyl;

A is a 5- to 7-membered carbocyclic or heterocyclic ring;

n is an integer of from 0 to 2;

each $R^f$ is independently selected from the group consisting of optionally substituted $C_{1-8}$ alkyl, optionally substituted $C_{2-8}$ alkenyl, optionally substituted $C_{2-8}$ alkynyl, optionally substituted 5 to 10-membered carbocyclyl, optionally substituted 5 to 10-membered heterocyclyl, optionally substituted 5 to 10-membered carbocyclyl-$C_{1-6}$ alkyl and optionally substituted 5 to 10-membered heterocyclyl-$C_{1-6}$ alkyl, said alkyl, alkenyl or alkynyl being optionally substituted with up to 3 substituents each independently selected from the group consisting of $OR^1$, $N(R^2)_2$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro and cyano, and said carbocyclyl or heterocyclyl being optionally substituted with up to 3 substituents each independently selected from the group consisting of $OR^1$, $N(R^2)_2$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, $C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

$R^g$ is selected from the group consisting of hydrogen, optionally substituted $C_{1-8}$ alkyl-C(O)—, optionally substituted $C_{1-8}$ alkyl, optionally substituted $C_{2-8}$ alkenyl, optionally substituted $C_{2-8}$ alkynyl, optionally substituted 5 to 10-membered carbocyclyl-C(O), optionally substituted 5 to 10-membered carbocyclyl, optionally substituted 5-10 membered heterocyclyl-C(O)—, optionally substituted 5 to 10-membered heterocyclyl, optionally substituted 5 to 10-membered carbocyclyl-$C_{1-6}$ alkyl and optionally substituted 5 to 10-membered heterocyclyl-$C_{1-6}$ alkyl, said alkyl-C(O)—, alkyl, alkenyl or alkynyl being optionally substituted with up to 3 substituents each independently selected from the group consisting of $OR^1$, $N(R^2)_2$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro and cyano, and said carbocyclyl-C(O)—, carbocyclyl, heterocyclyl-C(O)—, or heterocyclyl being optionally substituted with up to 3 substituents each independently selected from the group consisting of $OR^1$, $N(R^2)_2$, $SR^3$, —$C(O)C_{1-4}$alkyl, —$C(O)$phenyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens; and $R^h$ is absent or selected from the group consisting of halogen, cyano, $C_{1-6}$ alkyl optionally substituted with up to 3 halogens, and $C_{1-6}$ alkoxy.

In a preferred embodiment, the invention provides for a compound of Formula IA (IA)

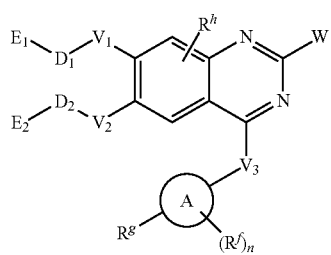

or a pharmaceutically acceptable salt thereof;
wherein W is

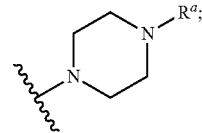

$R^a$ is selected from the group consisting of hydrogen, $C_{1-8}$ alkyl optionally substituted with up to three halogens, $C_{2-8}$ alkenyl optionally substituted with up to three halogens, $C_{2-8}$ alkynyl optionally substituted with up to three halogens, optionally substituted 5 to 10-membered carbocyclyl, optionally substituted 5 to 10-membered heterocyclyl, optionally substituted 5 to 10-membered carbocyclyl-$C_{1-6}$ alkyl and optionally substituted 5 to 10-membered heterocyclyl-$C_{1-6}$ alkyl, said carbocyclyl or heterocyclyl being optionally substituted with up to 3 substituents each independently selected from the group consisting of $OR^1$, $N(R^2)_2$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

each $R^1$ is independently selected from the group consisting of hydrogen, $C_{1-4}$alkyl, $C_{1-4}$trifluoroalkyl, —$C(O)C_{1-4}$alkyl, and —$C(O)C_{1-4}$trihaloalkyl;

each $R^2$ is independently selected from the group consisting of hydrogen, $C_{1-4}$alkyl, $C_{1-4}$trifluoroalkyl, —$C(O)C_{1-4}$alkyl, —$C(O)C_{1-4}$trihaloalkyl, —$S(O)_2C_{1-4}$alkyl, and —$S(O)_2C_{1-4}$trihaloalkyl;

each $R^3$ is independently selected from the group consisting of hydrogen, $C_{1-4}$alkyl, $C_{1-4}$trifluoroalkyl, —$C(O)C_{1-4}$alkyl, and —$C(O)C_{1-4}$trihaloalkyl;

either $V_1$ and $D_1$ are both absent and $E_1$ is hydrogen or halogen; or $V_1$ is selected from the group consisting of $NR^c$, O or S;

$D_1$ is absent or selected from the group consisting of optionally substituted $C_{1-8}$ alkylene, optionally substituted $C_{2-8}$ alkenylene and optionally substituted $C_{2-8}$ alkynylene, said $C_{1-8}$ alkylene, $C_{2-8}$ alkenylene or $C_{2-8}$ alkynylene being optionally substituted with up to 3 substituents each independently selected from the group consisting of $OR^1$, $N(R^2)_2$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro and cyano;

$E_1$ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of $OR^1$, $N(R^2)_2$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

either $V_2$ and $D_2$ are both absent and $E_2$ is hydrogen or halogen; or $V_2$ is selected from the group consisting of $NR^c$, O or S;

$D_2$ is absent or selected from the group consisting of optionally substituted $C_{1-8}$ alkylene, optionally substituted $C_{2-8}$ alkenylene and optionally substituted $C_{2-8}$ alkynylene, said $C_{1-8}$ alkylene, $C_{2-8}$ alkenylene or $C_{2-8}$ alkynylene being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro and cyano;

$E_2$ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of $OR^1$, $N(R^2)_2$, $SR^3$, —C(O)$C_{1-4}$alkyl, —C(O)$C_{1-4}$-trihaloalkyl, —C(O)O$C_{1-4}$alkyl, —C(O)O$C_{1-4}$trihaloalkyl, —C(O)NH$_2$, —C(O)NH$C_{1-4}$alkyl, C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

each $R^c$ is independently selected from the group consisting of hydrogen and $C_{1-6}$ alkyl;

$V_3$ is $NR^e$, O or S;

$R^e$ is hydrogen or $C_{1-6}$ alkyl;

A is a 5- to 7-membered carbocyclic or heterocyclic ring;

n is an integer of from 0 to 2;

each $R^f$ is independently selected from the group consisting of optionally substituted $C_{1-8}$ alkyl, optionally substituted $C_{2-8}$ alkenyl, optionally substituted $C_{2-8}$ alkynyl, optionally substituted 5 to 10-membered carbocyclyl, optionally substituted 5 to 10-membered heterocyclyl, optionally substituted 5 to 10-membered carbocyclyl-$C_{1-6}$ alkyl and optionally substituted 5 to 10-membered heterocyclyl-$C_{1-6}$ alkyl, said alkyl, alkenyl or alkynyl being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro and cyano, and said carbocyclyl or heterocyclyl being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

$R^g$ is selected from the group consisting of hydrogen, optionally substituted $C_{1-8}$ alkyl, optionally substituted $C_{2-8}$ alkenyl, optionally substituted $C_{2-8}$ alkynyl, optionally substituted 5 to 10-membered carbocyclyl, optionally substituted 5 to 10-membered heterocyclyl, optionally substituted 5 to 10-membered carbocyclyl-$C_{1-6}$ alkyl and optionally substituted 5 to 10-membered heterocyclyl-$C_{1-6}$ alkyl, said alkyl, alkenyl or alkynyl being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O) O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro and cyano, and said carbocyclyl or heterocyclyl being optionally substituted with up to 3 substituents each independently selected from the group consisting of $OR^1$, $N(R^2)_2$, $SR^3$, —C(O)$C_{1-4}$alkyl, —C(O)phenyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$ alkyl, —S(O)$_2$N($C_{1-4}$alkyl)$_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens; and $R^h$ is absent or selected from the group consisting of halogen, cyano, $C_{1-6}$ alkyl optionally substituted with up to 3 halogens, and $C_{1-6}$ alkoxy.

The invention also provides a compound of formula (IB)

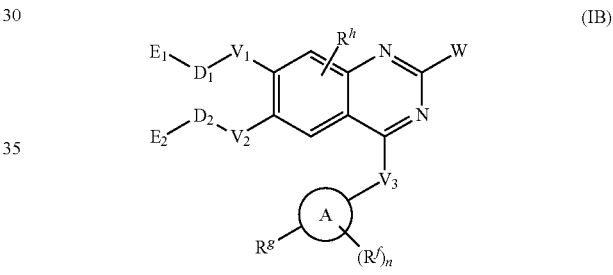

(IB)

or a pharmaceutically acceptable salt thereof;

wherein W is a 4 to 6-membered carbocycle or 4 to 6-membered heterocycle containing up to 2 heteroatoms and having the formula (IIB)

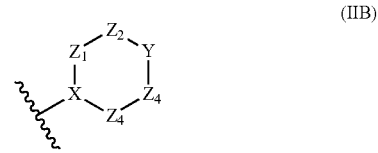

(IIB)

wherein

X is N or $CR^b$;

Y is $NR^b$, $NC(O)R^a$, $CR^aR^b$, O, C(O), $CR^aNR^bR^b$ or $CR^bC(O)R^a$ each of $Z_2$ and $Z_4$ is independently selected from the group consisting of O, S, $NR^b$, and $CR^bR^b$;

each of $Z_1$ and $Z_3$ is independently absent or selected from the group consisting of O, S, $NR^b$, and $CR^bR^b$;

with the proviso that two neighbouring ring atoms in W are not both heteroatoms;

$R^a$ is selected from the group consisting of hydrogen, halogen, $C_{1-8}$ alkyl optionally substituted with up to three halogens or $OC_{1-8}$ alkyl, $C_{2-8}$ alkenyl optionally substituted with up to three halogens, $C_{2-8}$ alkynyl optionally substituted with up to three halogens, optionally substituted 3 to 10-membered carbocyclyl, optionally substituted 3 to 10-membered heterocyclyl, optionally substituted 3 to 10-membered carbocyclyl-$C_{1-6}$ alkyl and optionally substituted 3 to 10-membered heterocyclyl-$C_{1-6}$ alkyl, said carbocyclyl or heterocyclyl being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

each $R^b$ is independently selected from the group consisting of hydrogen, $C_{1-8}$ alkyl optionally substituted with up to three halogens, $C_{2-8}$ alkenyl optionally substituted with up to three halogens, $C_{2-8}$ alkynyl optionally substituted with up to three halogens, optionally substituted 5 to 10-membered carbocyclyl, optionally substituted 5 to 10-membered heterocyclyl, optionally substituted 5 to 10-membered carbocyclyl-$C_{1-6}$ alkyl and optionally substituted 5 to 10-membered heterocyclyl-$C_{1-6}$ alkyl, said carbocyclyl or heterocyclyl being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

each $R^1$ is independently selected from the group consisting of hydrogen, $C_{1-4}$alkyl, $C_{1-4}$-trifluoroalkyl, —C(O)$C_{1-4}$alkyl, and —C(O)$C_{1-4}$trihaloalkyl;

each $R^2$ is independently selected from the group consisting of hydrogen, $C_{1-4}$alkyl, $C_{1-4}$trifluoroalkyl, —C(O)$C_{1-4}$alkyl, —C(O)$C_{1-4}$trihaloalkyl, —S(O)$_2C_{1-4}$alkyl, and —S(O)$_2C_{1-4}$trihaloalkyl;

each $R^3$ is independently selected from the group consisting of hydrogen, $C_{1-4}$alkyl, $C_{1-4}$trifluoroalkyl, —C(O)$C_{1-4}$alkyl, and —C(O)$C_{1-4}$trihaloalkyl;

and wherein up to 3 of said $R^a$ groups, said $R^b$ groups, or a combination of said $R^a$ and $R^b$ groups, may be other than hydrogen;

$V_1$ and $D_1$ are both absent and $E_1$ is hydrogen or halogen; or $V_1$ is selected from the group consisting of $NR^e$, O or S;

$D_1$ is absent or selected from the group consisting of optionally substituted $C_{1-8}$ alkylene, optionally substituted $C_{2-8}$ alkenylene and optionally substituted $C_{2-8}$ alkynylene, said $C_{1-8}$ alkylene, $C_{2-8}$ alkenylene or $C_{2-8}$ alkynylene being optionally substituted with up to 3 substituents each independently selected from the group consisting of $OR^1$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro and cyano;

$E_1$ is selected from the group consisting of hydrogen and optionally substituted 5 to 10-membered carbocyclyl, said carbocyclyl being optionally substituted with up to 3 substituents each independently selected from the group consisting of $OR^1$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

$V_2$ and $D_2$ are both absent and $E_2$ is hydrogen or halogen; or $V_2$ is selected from the group consisting of $NR^e$, O or S;

$D_2$ is absent or selected from the group consisting of optionally substituted $C_{1-8}$ alkylene, optionally substituted $C_{2-8}$ alkenylene and optionally substituted $C_{2-8}$ alkynylene, said $C_{1-8}$ alkylene, $C_{2-8}$ alkenylene or $C_{2-8}$ alkynylene being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro and cyano;

$E_2$ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro, cyano, $C_{1-4}$alkyl optionally substituted with up to 3 halogens, $C_{2-4}$-alkenyl optionally substituted with up to 3 halogens, and $C_{2-4}$alkynyl optionally substituted with up to 3 halogens;

each $R^c$ is independently selected from the group consisting of hydrogen and $C_{1-6}$ alkyl;

or wherein $V_1$ and $V_2$ are each independently selected from the group consisting of $NR^e$, O or S, $E_1$ and $E_2$ are both absent, and $D_1$ and $D_2$ together form a linker group between $V_1$ and $V_2$, said linker comprising optionally substituted $C_{1-4}$ alkylene, and said alkylene being optionally substituted with 1 or 2 substituents each independently selected from the group consisting of halogen, cyano and $OR^1$;

$V_3$ is $NR^e$, O or S;

$R^e$ is hydrogen or $C_{1-6}$ alkyl;

A is a 5- to 7-membered carbocyclic or heterocyclic ring;

n is an integer of from 0 to 2;

each $R^f$ is independently selected from the group consisting of optionally substituted $C_{1-8}$ alkyl, optionally substituted $C_{2-8}$ alkenyl, optionally substituted $C_{2-8}$ alkynyl, optionally substituted 5 to 10-membered carbocyclyl, optionally substituted 5 to 10-membered heterocyclyl, optionally substituted 5 to 10-membered carbocyclyl-$C_{1-6}$ alkyl and optionally substituted 5 to 10-membered heterocyclyl-$C_{1-6}$ alkyl, said alkyl, alkenyl or alkynyl being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2C_{1-4}$alkyl, —S(O)$_2$NH$_2$, S(O)$_2$NH$C_{1-4}$alkyl, —S(O)$_2$N($C_{1-4}$alkyl)$_2$, halogen, nitro and cyano, and said carbocyclyl or heterocyclyl being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens;

R$^g$ is selected from the group consisting of hydrogen, optionally substituted C$_{1-8}$ alkyl-C(O)—, optionally substituted C$_{1-8}$ alkyl, optionally substituted C$_{2-8}$ alkenyl, optionally substituted C$_{2-8}$ alkynyl, optionally substituted 5 to 10-membered carbocyclyl-C(O), optionally substituted 5 to 10-membered carbocyclyl, optionally substituted 5-10 membered heterocyclyl-C(O)—, optionally substituted 5 to 10-membered heterocyclyl, optionally substituted 5 to 10-membered carbocyclyl-C$_{1-6}$ alkyl and optionally substituted 5 to 10-membered heterocyclyl-C$_{1-6}$ alkyl, said alkyl-C(O)—, alkyl, alkenyl or alkynyl being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro and cyano, and said carbocyclyl-C(O)—, carbocyclyl, heterocyclyl-C(O)—, or heterocyclyl being optionally substituted with up to 3 substituents each independently selected from the group consisting of OR$^1$, N(R$^2$)$_2$, SR$^3$, —C(O)C$_{1-4}$alkyl, —C(O)phenyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens; and R$^h$ is absent or selected from the group consisting of halogen, cyano, C$_{1-6}$ alkyl optionally substituted with up to 3 halogens, and C$_{1-6}$ alkoxy, wherein the compound is not a compound of formula (IIIB) or (IVB)

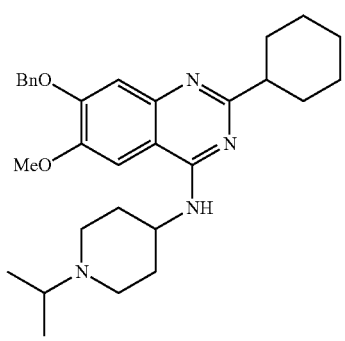

(IIIB)

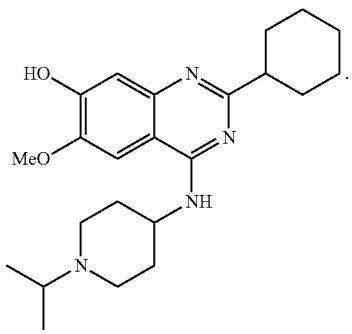

(IVB)

In a preferred embodiment the invention also provides a compound of formula (IB)

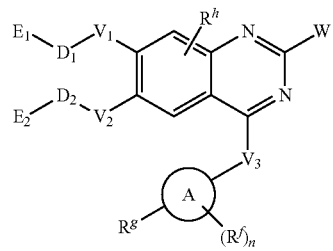

(IB)

or a pharmaceutically acceptable salt thereof;
wherein W is a 6-membered carbocycle or 6-membered heterocycle containing up to 2 heteroatoms and having the formula (IIB)

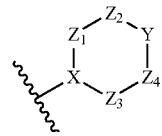

(IIB)

wherein
X is N or CR$^b$;
Y is NR$^a$, or CR$^a$R$^b$;
each of Z$_1$, Z$_2$, Z$_3$ and Z$_4$ is independently selected from the group consisting of O, S, NR$^b$, and CR$^b$R$^b$;
with the proviso that two neighbouring ring atoms in W are not both heteroatoms;
R$^a$ is selected from the group consisting of hydrogen, C$_{1-8}$ alkyl optionally substituted with up to three halogens, C$_{2-8}$ alkenyl optionally substituted with up to three halogens, C$_{2-8}$ alkynyl optionally substituted with up to three halogens, optionally substituted 5 to 10-membered carbocyclyl, optionally substituted 5 to 10-membered heterocyclyl, optionally substituted 5 to 10-membered carbocyclyl-C$_{1-6}$ alkyl and optionally substituted 5 to 10-membered heterocyclyl-C$_{1-6}$ alkyl, said carbocyclyl or heterocyclyl being optionally substituted with up to 3 substituents each independently selected from the group consisting of OR$^1$, N(R$^2$)$_2$, SR$^3$, —C(O)C$_{1-4}$ alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)₂NHC₁₋₄alkyl, —S(O)₂N(C₁₋₄alkyl)₂, halogen, nitro, cyano, C₁₋₄ alkyl optionally substituted with up to 3 halogens, C₂₋₄-alkenyl optionally substituted with up to 3 halogens, and C₂₋₄alkynyl optionally substituted with up to 3 halogens;

each $R^b$ is independently selected from the group consisting of hydrogen, C₁₋₈ alkyl optionally substituted with up to three halogens, C₂₋₈ alkenyl optionally substituted with up to three halogens, C₂₋₈ alkynyl optionally substituted with up to three halogens, optionally substituted 5 to 10-membered carbocyclyl, optionally substituted 5 to 10-membered heterocyclyl, optionally substituted 5 to 10-membered carbocyclyl-C₁₋₆ alkyl and optionally substituted 5 to 10-membered heterocyclyl-C₁₋₆ alkyl, said carbocyclyl or heterocyclyl being optionally substituted with up to 3 substituents each independently selected from the group consisting of OR¹, N(R²)₂, SR³, —C(O)C₁₋₄trihaloalkyl, —C(O)OC₁₋₄alkyl, —C(O)OC₁₋₄trihaloalkyl, —C(O)NH₂, —C(O)NHC₁₋₄alkyl, —C(O)N(C₁₋₄alkyl)₂, —S(O)₂C₁₋₄alkyl, —S(O)₂NH₂, —S(O)₂NHC₁₋₄alkyl, —S(O)₂N(C₁₋₄alkyl)₂, halogen, nitro, cyano, C₁₋₄ alkyl optionally substituted with up to 3 halogens, C₂₋₄-alkenyl optionally substituted with up to 3 halogens, and C₂₋₄alkynyl optionally substituted with up to 3 halogens;

each $R^1$ is independently selected from the group consisting of hydrogen, C₁₋₄alkyl, C₁₋₄trifluoroalkyl, —C(O)C₁₋₄alkyl, and —C(O)C₁₋₄trihaloalkyl;

each $R^2$ is independently selected from the group consisting of hydrogen, C₁₋₄alkyl, C₁₋₄trifluoroalkyl, —C(O)C₁₋₄trihaloalkyl, —S(O)₂C₁₋₄alkyl, and —S(O)₂C₁₋₄trihaloalkyl;

each $R^3$ is independently selected from the group consisting of hydrogen, C₁₋₄alkyl, C₁₋₄trifluoroalkyl, —C(O)C₁₋₄alkyl, and —C(O)C₁₋₄trihaloalkyl;

and wherein up to 3 of said $R^a$ groups, said $R^b$ groups, or a combination of said $R^a$ and $R^b$ groups, may be other than hydrogen;

either $V_1$ and $D_1$ are both absent and $E_1$ is hydrogen or halogen; or $V_1$ is selected from the group consisting of $NR^c$, O or S;
$D_1$ is absent or selected from the group consisting of optionally substituted C₁₋₈ alkylene, optionally substituted C₂₋₈ alkenylene and optionally substituted C₂₋₈ alkynylene, said C₁₋₈ alkylene, C₂₋₈ alkenylene or C₂₋₈ alkynylene being optionally substituted with up to 3 substituents each independently selected from the group consisting of OR¹, SR³, —C(O)C₁₋₄alkyl, —C(O)C₁₋₄trihaloalkyl, —C(O)OC₁₋₄alkyl, —C(O)OC₁₋₄trihaloalkyl, —C(O)NH₂, —C(O)NHC₁₋₄alkyl, —C(O)N(C₁₋₄alkyl)₂, —S(O)C₁₋₄alkyl, —S(O)₂C₁₋₄alkyl, —S(O)₂NH₂, —S(O)₂NHC₁₋₄alkyl, —S(O)₂N(C₁₋₄alkyl)₂, halogen, nitro and cyano;

$E_1$ is selected from the group consisting of hydrogen and optionally substituted 5 to 10-membered carbocyclyl, said carbocyclyl being optionally substituted with up to 3 substituents each independently selected from the group consisting of OR¹, SR³, —C(O)C₁₋₄alkyl, —C(O)C₁₋₄trihaloalkyl, —C(O)OC₁₋₄alkyl, —C(O)OC₁₋₄trihaloalkyl, —C(O)NH₂, —C(O)NHC₁₋₄alkyl, —C(O)N(C₁₋₄alkyl)₂, —S(O)C₁₋₄alkyl, —S(O)₂C₁₋₄alkyl, —S(O)₂NH₂, —S(O)₂NHC₁₋₄alkyl, —S(O)₂N(C₁₋₄alkyl)₂, halogen, nitro, cyano, C₁₋₄ alkyl optionally substituted with up to 3 halogens, C₂₋₄-alkenyl optionally substituted with up to 3 halogens, and C₂₋₄alkynyl optionally substituted with up to 3 halogens;

either $V_2$ and $D_2$ are both absent and $E_2$ is hydrogen or halogen; or $V_2$ is selected from the group consisting of $NR^c$, O or S;

$D_2$ is absent or selected from the group consisting of optionally substituted C₁₋₈ alkylene, optionally substituted C₂₋₈ alkenylene and optionally substituted C₂₋₈ alkynylene, said C₁₋₈ alkylene, C₂₋₈ alkenylene or C₂₋₈ alkynylene being optionally substituted with up to 3 substituents each independently selected from the group consisting of OR¹, N(R²)₂, SR³, —C(O)C₁₋₄alkyl, —C(O)C₁₋₄trihaloalkyl, —C(O)OC₁₋₄alkyl, —C(O)OC₁₋₄trihaloalkyl, —C(O)NH₂, —C(O)NHC₁₋₄alkyl, —C(O)N(C₁₋₄alkyl)₂, —S(O)C₁₋₄alkyl, —S(O)₂C₁₋₄alkyl, —S(O)₂NH₂, —S(O)₂NHC₁₋₄alkyl, —S(O)₂N(C₁₋₄alkyl)₂, halogen, nitro and cyano;

$E_2$ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of OR¹, N(R²)₂, SR³, —C(O)C₁₋₄alkyl, —C(O)C₁₋₄trihaloalkyl, —C(O)OC₁₋₄alkyl, —C(O)OC₁₋₄trihaloalkyl, —C(O)NH₂, —C(O)NHC₁₋₄alkyl, —C(O)N(C₁₋₄alkyl)₂, —S(O)C₁₋₄alkyl, —S(O)₂C₁₋₄alkyl, —S(O)₂NH₂, —S(O)₂NHC₁₋₄alkyl, —S(O)₂N(C₁₋₄alkyl)₂, halogen, nitro, cyano, C₁₋₄ alkyl optionally substituted with up to 3 halogens, C₂₋₄-alkenyl optionally substituted with up to 3 halogens, and C₂₋₄alkynyl optionally substituted with up to 3 halogens;

each $R^c$ is independently selected from the group consisting of hydrogen and C₁₋₆ alkyl;

$V_3$ is $NR^e$, O or S;

$R^e$ is hydrogen or C₁₋₆ alkyl;

A is a 5- to 7-membered carbocyclic or heterocyclic ring;

n is an integer of from 0 to 2;

each $R^f$ is independently selected from the group consisting of optionally substituted C₁₋₈ alkyl, optionally substituted C₂₋₈ alkenyl, optionally substituted C₂₋₈ alkynyl, optionally substituted 5 to 10-membered carbocyclyl, optionally substituted 5 to 10-membered heterocyclyl, optionally substituted 5 to 10-membered carbocyclyl-C₁₋₆ alkyl and optionally substituted 5 to 10-membered heterocyclyl-C₁₋₆ alkyl, said alkyl, alkenyl or alkynyl being optionally substituted with up to 3 substituents each independently selected from the group consisting of OR¹, N(R²)₂, SR³, —C(O)C₁₋₄alkyl, —C(O)C₁₋₄trihaloalkyl, —C(O)OC₁₋₄alkyl, —C(O)OC₁₋₄trihaloalkyl, —C(O)NH₂, —C(O)NHC₁₋₄alkyl, —C(O)N(C₁₋₄alkyl)₂, —S(O)C₁₋₄alkyl, —S(O)₂C₁₋₄alkyl, —S(O)₂NH₂, —S(O)₂NHC₁₋₄alkyl, —S(O)₂N(C₁₋₄alkyl)₂, halogen, nitro and cyano, and said carbocyclyl or heterocyclyl being optionally substituted with up to 3 substituents each independently selected from the group consisting of OR¹, N(R²)₂, SR³, —C(O)C₁₋₄alkyl, —C(O)C₁₋₄trihaloalkyl, —C(O)OC₁₋₄alkyl, —C(O)OC₁₋₄trihaloalkyl, —C(O)NH₂, —C(O)NHC₁₋₄alkyl, —C(O)N(C₁₋₄alkyl)₂, —S(O)C₁₋₄alkyl, —S(O)₂C₁₋₄alkyl, —S(O)₂NH₂, —S(O)₂NHC₁₋₄alkyl, —S(O)₂N(C₁₋₄alkyl)₂, halogen, nitro, cyano, C₁₋₄alkyl optionally substituted with up to 3 halogens, C₂₋₄-alkenyl optionally substituted with up to 3 halogens, and C₂₋₄alkynyl optionally substituted with up to 3 halogens;

$R^g$ is selected from the group consisting of hydrogen, optionally substituted C₁₋₈ alkyl, optionally substituted C₂₋₈ alkenyl, optionally substituted C₂₋₈ alkynyl, optionally substituted 5 to 10-membered carbocyclyl, optionally substituted 5 to 10-membered heterocyclyl, optionally substituted 5 to 10-membered carbocyclyl-C₁₋₆ alkyl and optionally substituted 5 to 10-membered heterocyclyl-C₁₋₆ alkyl, said alkyl, alkenyl or alkynyl being optionally substituted with up to 3 substituents each independently selected from the group consisting of OR¹, N(R²)₂, SR³, —C(O)C₁₋₄alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro and cyano, and said carbocyclyl or heterocyclyl being optionally substituted with up to 3 substituents each independently selected from the group consisting of OR$^1$, N(R$^2$)$_2$, SR$^3$, —C(O)C$_{1-4}$alkyl, —C(O)phenyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens; and R$^h$ is absent or selected from the group consisting of halogen, cyano, C$_{1-6}$ alkyl optionally substituted with up to 3 halogens, and C$_{1-6}$ alkoxy, wherein the compound is not a compound of formula (IIIB) or (IVB)

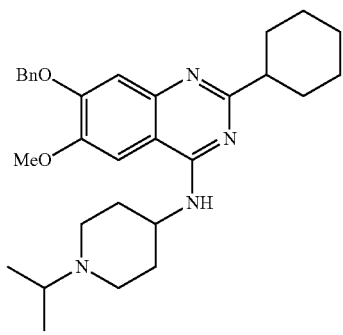

(IIIB)

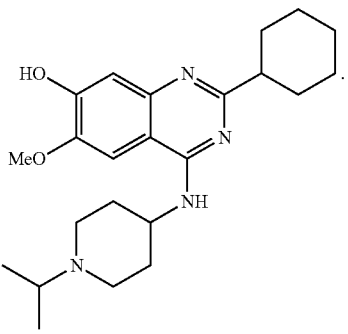

(IVB)

The invention also provides a compound of formula (IC)

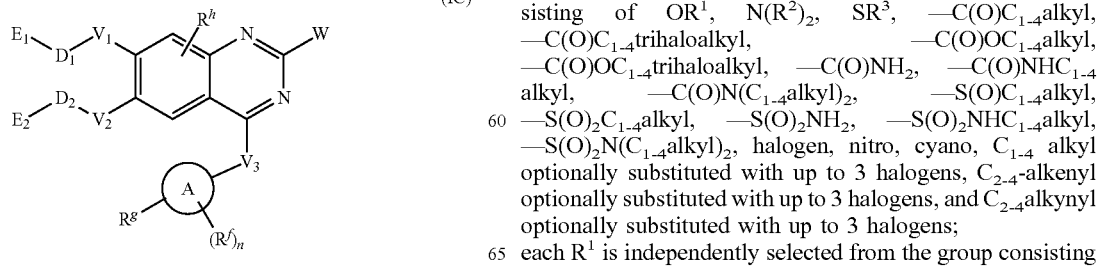

(IC)

or a pharmaceutically acceptable salt thereof;

wherein W is a 4 to 6-membered carbocycle or 4 to 6-membered heterocycle containing up to 2 heteroatoms and having the formula (IIB)

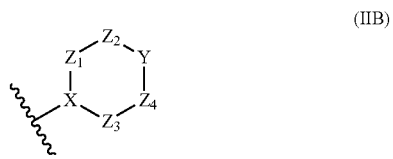

(IIB)

wherein
X is N or CR$^b$;
Y is NR$^b$, NC(O)R$^a$, CR$^a$R$^b$, O, C(O), CR$^a$R$^b$R$^b$ or CR$^b$C(O)R$^a$ each of Z$_2$ and Z$_4$ is independently selected from the group consisting of O, S, NR$^b$, and CR$^b$R$^b$;

each of Z$_1$ and Z$_3$ is independently absent or selected from the group consisting of O, S, NR$^b$, and CR$^b$R$^b$;

with the proviso that two neighbouring ring atoms in W are not both heteroatoms;

R$^a$ is selected from the group consisting of hydrogen, halogen, C$_{1-8}$ alkyl optionally substituted with up to three halogens or OC$_{1-8}$ alkyl, C$_{2-8}$ alkenyl optionally substituted with up to three halogens, C$_{2-8}$ alkynyl optionally substituted with up to three halogens, optionally substituted 3 to 10-membered carbocyclyl, optionally substituted 3 to 10-membered heterocyclyl, optionally substituted 3 to 10-membered carbocyclyl-C$_{1-6}$ alkyl and optionally substituted 3 to 10-membered heterocyclyl-C$_{1-6}$ alkyl, said carbocyclyl or heterocyclyl being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$ alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens;

each R$^b$ is independently selected from the group consisting of hydrogen, C$_{1-8}$ alkyl optionally substituted with up to three halogens, C$_{2-8}$ alkenyl optionally substituted with up to three halogens, C$_{2-8}$ alkynyl optionally substituted with up to three halogens, optionally substituted 5 to 10-membered carbocyclyl, optionally substituted 5 to 10-membered heterocyclyl, optionally substituted 5 to 10-membered carbocyclyl-C$_{1-6}$ alkyl and optionally substituted 5 to 10-membered heterocyclyl-C$_{1-6}$ alkyl, said carbocyclyl or heterocyclyl being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens;

each R$^1$ is independently selected from the group consisting of hydrogen, C$_{1-4}$alkyl, C$_{1-4}$trifluoroalkyl, —C(O)C$_{1-4}$alkyl, and —C(O)C$_{1-4}$trihaloalkyl;

each $R^2$ is independently selected from the group consisting of hydrogen, $C_{1-4}$alkyl, $C_{1-4}$trifluoroalkyl, —C(O)$C_{1-4}$alkyl, —C(O)$C_{1-4}$trihaloalkyl, —S(O)$_2C_{1-4}$alkyl, and —S(O)$_2C_{1-4}$trihaloalkyl;

each $R^3$ is independently selected from the group consisting of hydrogen, $C_{1-4}$alkyl, $C_{1-4}$-trifluoroalkyl, —C(O)$C_{1-4}$alkyl, and —C(O)$C_{1-4}$trihaloalkyl;

and wherein up to 3 of said $R^a$ groups, said $R^b$ groups, or a combination of said $R^a$ and $R^b$ groups, may be other than hydrogen;

$V_1$ and $D_1$ are both absent and $E_1$ is hydrogen or halogen; or $V_1$ is selected from the group consisting of $NR^c$, O or S; $D_1$ is absent or selected from the group consisting of optionally substituted $C_{1-8}$ alkylene, optionally substituted $C_{2-8}$ alkenylene and optionally substituted $C_{2-8}$ alkynylene, said $C_{1-8}$ alkylene, $C_{2-8}$ alkenylene or $C_{2-8}$ alkynylene being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)$NH_2$, —C(O)$NHC_{1-4}$alkyl, —C(O)$N(C_{1-4}$alkyl$)_2$, —S(O)$C_{1-4}$alkyl, —S(O)$_2C_{1-4}$alkyl, —S(O)$_2NH_2$, —S(O)$_2NHC_{1-4}$alkyl, —S(O)$_2N(C_{1-4}$alkyl$)_2$, halogen, nitro and cyano;

$E_1$ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)$NH_2$, —C(O)$NHC_{1-4}$alkyl, —C(O)$N(C_{1-4}$alkyl$)_2$, —S(O)$C_{1-4}$alkyl, —S(O)$_2C_{1-4}$alkyl, —S(O)$_2NH_2$, S(O)$_2NHC_{1-4}$alkyl, —S(O)$_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

$V_2$ and $D_2$ are both absent and $E_2$ is hydrogen or halogen; or $V_2$ is selected from the group consisting of $NR^c$, O or S; $D_2$ is absent or selected from the group consisting of optionally substituted $C_{1-8}$ alkylene, optionally substituted $C_{2-8}$ alkenylene and optionally substituted $C_{2-8}$ alkynylene, said $C_{1-8}$ alkylene, $C_{2-8}$ alkenylene or $C_{2-8}$ alkynylene being optionally substituted with up to 3 substituents each independently selected from the group consisting of $OR^1$, $N(R^2)_2$, $SR^3$, —C(O)$C_{1-4}$alkyl, —C(O)$C_{1-4}$-trihaloalkyl, —C(O)O$C_{1-4}$alkyl, —C(O)O$C_{1-4}$trihaloalkyl, —C(O)$NH_2$, —C(O)$NHC_{1-4}$alkyl, —C(O)$N(C_{1-4}$alkyl$)_2$, —S(O)$C_{1-4}$alkyl, —S(O)$_2C_{1-4}$alkyl, —S(O)$_2NH_2$, —S(O)$_2NHC_{1-4}$alkyl, —S(O)$_2N(C_{1-4}$alkyl$)_2$, halogen, nitro and cyano;

$E_2$ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of $OR^1$, $N(R^2)_2$, $SR^3$, —C(O)$C_{1-4}$alkyl, —C(O)$C_{1-4}$trihaloalkyl, —C(O)O$C_{1-4}$alkyl, —C(O)O$C_{1-4}$trihalo alkyl, —C(O)$NH_2$, —C(O)$NHC_{1-4}$alkyl, —C(O)$N(C_{1-4}$alkyl$)_2$, —S(O)$C_{1-4}$alkyl, —S(O)$_2C_{1-4}$alkyl, —S(O)$_2NH_2$, —S(O)$_2NHC_{1-4}$alkyl, —S(O)$_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

each $R^c$ is independently selected from the group consisting of hydrogen and $C_{1-6}$ alkyl;

or wherein $V_1$ and $V_2$ are each independently selected from the group consisting of $NR^c$, O or S, $E_1$ and $E_2$ are both absent, and $D_1$ and $D_2$ together form a linker group between $V_1$ and $V_2$, said linker comprising optionally substituted $C_{1-4}$ alkylene, and said alkylene being optionally substituted with 1 or 2 substituents each independently selected from the group consisting of halogen, cyano and $OR^1$;

$V_3$ is $NR^e$;

$R^e$ is hydrogen;

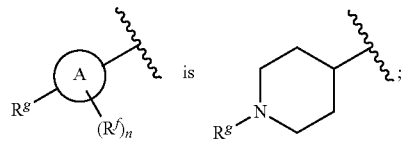

$R^g$ is selected from the group consisting of optionally substituted 6 to 10-membered aryl, optionally substituted 5 to 10-membered heteroaryl, optionally substituted 6 to 10-membered aryl-$C_{1-6}$ alkyl and optionally substituted 5 to 10-membered heteroaryl-$C_{1-6}$ alkyl, said aryl or heteroaryl being optionally substituted with up to 3 substituents each independently selected from the group consisting of $OR^1$, $N(R^2)_2$, $SR^3$, —C(O)$C_{1-4}$alkyl, —C(O)phenyl, —C(O)$C_{1-4}$-trihaloalkyl, —C(O)O$C_{1-4}$ alkyl, —C(O)O$C_{1-4}$trihaloalkyl, —C(O)$NH_2$, —C(O)$NHC_{1-4}$alkyl, —C(O)$N(C_{1-4}$alkyl$)_2$, —S(O)$C_{1-4}$alkyl, —S(O)$_2C_{1-4}$alkyl, —S(O)$_2NH_2$, —S(O)$_2NHC_{1-4}$ alkyl, —S(O)$_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens; and $R^h$ is absent or selected from the group consisting of halogen, cyano, $C_{1-6}$ alkyl optionally substituted with up to 3 halogens, and $C_{1-6}$ alkoxy.

In a preferred embodiment, the invention also provides a compound of formula (IC)

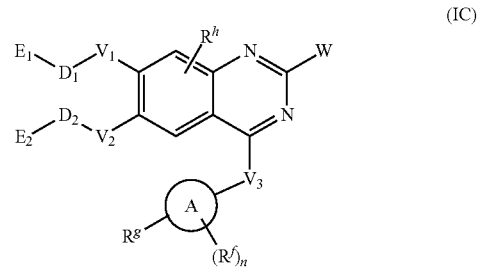

(IC)

or a pharmaceutically acceptable salt thereof;
wherein W is a 6-membered carbocycle or 6-membered heterocycle containing up to 2 heteroatoms and having the formula (IIC)

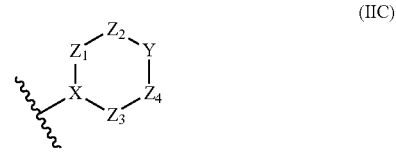

(IIC)

wherein
X is N or CR$^b$;
Y is NR$^a$ or CR$^a$R$^b$;
each of Z$_1$, Z$_2$, Z$_3$ and Z$_4$ is independently selected from the group consisting of O, S, NR$^b$, and CR$^b$R$^b$;
with the proviso that two neighbouring ring atoms in W are not both heteroatoms;
R$^a$ is selected from the group consisting of hydrogen, C$_{1-8}$ alkyl optionally substituted with up to three halogens, C$_{2-8}$ alkenyl optionally substituted with up to three halogens, C$_{2-8}$ alkynyl optionally substituted with up to three halogens, optionally substituted 5 to 10-membered carbocyclyl, optionally substituted 5 to 10-membered heterocyclyl, optionally substituted 5 to 10-membered carbocyclyl-C$_{1-6}$ alkyl and optionally substituted 5 to 10-membered heterocyclyl-C$_{1-6}$ alkyl, said carbocyclyl or heterocyclyl being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens;
each R$^b$ is independently selected from the group consisting of hydrogen, C$_{1-8}$ alkyl optionally substituted with up to three halogens, C$_{2-8}$ alkenyl optionally substituted with up to three halogens, C$_{2-8}$ alkynyl optionally substituted with up to three halogens, optionally substituted 5 to 10-membered carbocyclyl, optionally substituted 5 to 10-membered heterocyclyl, optionally substituted 5 to 10-membered carbocyclyl-C$_{1-6}$ alkyl and optionally substituted 5 to 10-membered heterocyclyl-C$_{1-6}$ alkyl, said carbocyclyl or heterocyclyl being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens;
each R$^1$ is independently selected from the group consisting of hydrogen, C$_{1-4}$alkyl, C$_{1-4}$trifluoroalkyl, —C(O)C$_{1-4}$alkyl, and —C(O)C$_{1-4}$trihaloalkyl;
each R$^2$ is independently selected from the group consisting of hydrogen, C$_{1-4}$alkyl, C$_{1-4}$trifluoroalkyl, —C(O)C$_{1-4}$alkyl, —C(O)C$_{1-4}$trihaloalkyl, —S(O)$_2$C$_{1-4}$alkyl, and —S(O)$_2$C$_{1-4}$trihaloalkyl;
each R$^3$ is independently selected from the group consisting of hydrogen, C$_{1-4}$alkyl, C$_{1-4}$-trifluoroalkyl, —C(O)C$_{1-4}$alkyl, and —C(O)C$_{1-4}$trihaloalkyl;
and wherein up to 3 of said R$^a$ groups, said R$^b$ groups, or a combination of said R$^a$ and R$^b$ groups, may be other than hydrogen;
either V$_1$ and D$_1$ are both absent and E$_1$ is hydrogen or halogen; or
V$_1$ is selected from the group consisting of NR$^c$, O or S;
D$_1$ is absent or selected from the group consisting of optionally substituted C$_{1-8}$ alkylene, optionally substituted C$_{2-8}$ alkenylene and optionally substituted C$_{2-8}$ alkynylene, said C$_{1-8}$ alkylene, C$_{2-8}$ alkenylene or C$_{2-8}$ alkynylene being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro and cyano;
E$_1$ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens;
either V$_2$ and D$_2$ are both absent and E$_2$ is hydrogen or halogen; or
V$_2$ is selected from the group consisting of NR$^c$, O or S;
D$_2$ is absent or selected from the group consisting of optionally substituted C$_{1-8}$ alkylene, optionally substituted C$_{2-8}$ alkenylene and optionally substituted C$_{2-8}$ alkynylene, said C$_{1-8}$ alkylene, C$_{2-8}$ alkenylene or C$_{2-8}$ alkynylene being optionally substituted with up to 3 substituents each independently selected from the group consisting of OR$^1$,qj N(R$^2$)$_2$, SR$^3$, —C(O)C$_{1-4}$ alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro and cyano;
E$_2$ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens;
each R$^c$ is independently selected from the group consisting of hydrogen and C$_{1-6}$ alkyl;
V$_3$ is NR$^e$;
R$^e$ is hydrogen;

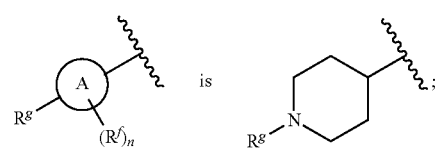

R$^g$ is selected from the group consisting of optionally substituted 6 to 10-membered aryl; optionally substituted 5 to 10-membered heteroaryl, optionally substituted 6 to 10-membered aryl-C$_{1-6}$ alkyl and optionally substituted 5 to 10-membered heteroaryl-C$_{1-6}$ alkyl, said aryl or heteroaryl being optionally substituted with up to 3 substituents each independently selected from the group consisting of OR$^1$, N(R²)₂, SR³, —C(O)C₁₋₄alkyl, —C(O)phenyl, —C(O)C₁₋₄trihaloalkyl, —C(O)OC₁₋₄ alkyl, —C(O)OC₁₋₄trihaloalkyl, —C(O)NH₂, —C(O)NHC₁₋₄alkyl, —C(O)N(C₁₋₄alkyl)₂, —S(O)C₁₋₄alkyl, —S(O)₂C₁₋₄alkyl, —S(O)₂NH₂, —S(O)₂NHC₁₋₄alkyl, —S(O)₂N(C₁₋₄alkyl)₂, halogen, nitro, cyano, C₁₋₄ alkyl optionally substituted with up to 3 halogens, C₂₋₄-alkenyl optionally substituted with up to 3 halogens, and C₂₋₄alkynyl optionally substituted with up to 3 halogens; and R$^h$ is absent or selected from the group consisting of halogen, cyano, C₁₋₆ alkyl optionally substituted with up to 3 halogens, and C₁₋₆ alkoxy.

The invention also provides for a compound of formula (ID)

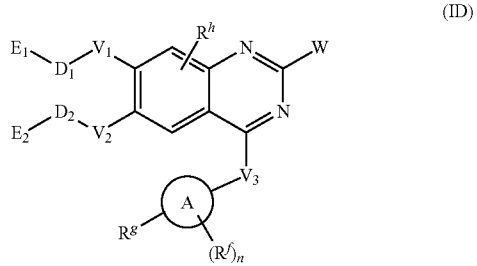

or a pharmaceutically acceptable salt thereof;
wherein W is a 7-membered carbocycle or 7-membered heterocycle containing up to 2 heteroatoms and having the formula (IID)

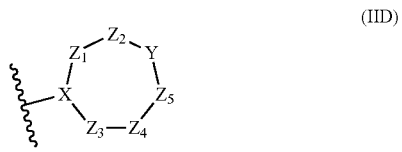

wherein
X is N or CR$^b$;
Y is NR$^b$, NC(O)R$^a$, CR$^a$R$^b$, O, C(O), CR$^a$NR$^b$R$^b$ or CR$^b$C(O)R$^a$
each of Z₁, Z₂, Z₃, Z₄ and Z₅ is independently selected from the group consisting of O, S, NR$^b$, and CR$^b$R$^b$
with the proviso that two neighbouring ring atoms in W are not both heteroatoms;

R$^a$ is selected from the group consisting of hydrogen, halogen, C₁₋₈ alkyl optionally substituted with up to three halogens or OC₁₋₈ alkyl, C₂₋₈ alkenyl optionally substituted with up to three halogens, C₂₋₈ alkynyl optionally substituted with up to three halogens, optionally substituted 3 to 10-membered carbocyclyl, optionally substituted 3 to 10-membered heterocyclyl, optionally substituted 3 to 10-membered carbocyclyl-C₁₋₆ alkyl and optionally substituted 3 to 10-membered heterocyclyl-C₁₋₆ alkyl, said carbocyclyl or heterocyclyl being optionally substituted with up to 3 substituents each independently selected from the group consisting of OR¹, N(R²)₂, SR³, —C(O)C₁₋₄alkyl, —C(O)C₁₋₄trihaloalkyl, —C(O)OC₁₋₄alkyl, —C(O)OC₁₋₄trihaloalkyl, —C(O)NH₂, —C(O)NHC₁₋₄alkyl, —C(O)N(C₁₋₄alkyl)₂, —S(O)C₁₋₄alkyl, —S(O)₂C₁₋₄alkyl, —S(O)₂NH₂, —S(O)₂NHC₁₋₄alkyl, —S(O)₂N(C₁₋₄alkyl)₂, halogen, nitro, cyano, C₁₋₄ alkyl optionally substituted with up to 3 halogens, C₂₋₄-alkenyl optionally substituted with up to 3 halogens, and C₂₋₄alkynyl optionally substituted with up to 3 halogens;

each R$^b$ is independently selected from the group consisting of hydrogen, C₁₋₈ alkyl optionally substituted with up to three halogens, C₂₋₈ alkenyl optionally substituted with up to three halogens, C₂₋₈ alkynyl optionally substituted with up to three halogens, optionally substituted 5 to 10-membered carbocyclyl, optionally substituted 5 to 10-membered heterocyclyl, optionally substituted 5 to 10-membered carbocyclyl-C₁₋₆ alkyl and optionally substituted 5 to 10-membered heterocyclyl-C₁₋₆ alkyl, said carbocyclyl or heterocyclyl being optionally substituted with up to 3 substituents each independently selected from the group consisting of OR¹, N(R²)₂, SR³, —C(O)C₁₋₄alkyl, —C(O)C₁₋₄trihaloalkyl, —C(O)OC₁₋₄alkyl, —C(O)OC₁₋₄trihaloalkyl, —C(O)NH₂, —C(O)NHC₁₋₄alkyl, —C(O)N(C₁₋₄alkyl)₂, —S(O)C₁₋₄alkyl, —S(O)₂C₁₋₄alkyl, —S(O)₂NH₂, —S(O)₂NHC₁₋₄alkyl, —S(O)₂N(C₁₋₄alkyl)₂, halogen, nitro, cyano, C₁₋₄ alkyl optionally substituted with up to 3 halogens, C₂₋₄-alkenyl optionally substituted with up to 3 halogens, and C₂₋₄alkynyl optionally substituted with up to 3 halogens;

each R¹ is independently selected from the group consisting of hydrogen, C₁₋₄alkyl, C₁₋₄-trifluoroalkyl, —C(O)C₁₋₄alkyl, and —C(O)C₁₋₄trihaloalkyl;

each R² is independently selected from the group consisting of hydrogen, C₁₋₄alkyl, C₁₋₄trifluoroalkyl, —C(O)C₁₋₄alkyl, —C(O)C₁₋₄trihaloalkyl, —S(O)₂C₁₋₄alkyl, and —S(O)₂C₁₋₄trihaloalkyl;

each R³ is independently selected from the group consisting of hydrogen, C₁₋₄alkyl, C₁₋₄trifluoroalkyl, —C(O)C₁₋₄alkyl, and —C(O)C₁₋₄trihaloalkyl;

and wherein up to 3 of said R$^a$ groups, said R$^b$ groups, or a combination of said R$^a$ and R$^b$ groups, may be other than hydrogen;

V₁ and D₁ are both absent and E₁ is hydrogen or halogen; or V₁ is selected from the group consisting of NR$^c$, O or S;
D₁ is absent or selected from the group consisting of optionally substituted C₁₋₈ alkylene, optionally substituted C₂₋₈ alkenylene and optionally substituted C₂₋₈ alkynylene, said C₁₋₈ alkylene, C₂₋₈ alkenylene or C₂₋₈ alkynylene being optionally substituted with up to 3 substituents each independently selected from the group consisting of OR¹, N(R²)₂, SR³, —C(O)C₁₋₄alkyl, —C(O)C₁₋₄trihaloalkyl, —C(O)OC₁₋₄alkyl, —C(O)OC₁₋₄trihaloalkyl, —C(O)NH₂, —C(O)NHC₁₋₄alkyl, —C(O)N(C₁₋₄alkyl)₂, —S(O)C₁₋₄alkyl, —S(O)₂C₁₋₄alkyl, —S(O)₂NH₂, —S(O)₂NHC₁₋₄alkyl, —S(O)₂N(C₁₋₄alkyl)₂, halogen, nitro and cyano;

E₁ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of OR¹, N(R²)₂, SR³, —C(O)C₁₋₄alkyl, —C(O)C₁₋₄trihaloalkyl, —C(O)OC₁₋₄ alkyl, —C(O)OC₁₋₄trihaloalkyl, —C(O)NH₂, —C(O)NHC₁₋₄alkyl, —C(O)N(C₁₋₄alkyl)₂, —S(O)C₁₋₄alkyl, —S(O)₂C₁₋₄alkyl, —S(O)₂NH₂, —S(O)₂NHC₁₋₄alkyl, —S(O)₂N(C₁₋₄alkyl)₂, halogen, nitro, cyano, C₁₋₄ alkyl optionally substituted with up to 3 halogens, C₂₋₄-alkenyl optionally substituted with up to 3 halogens, and C₂₋₄alkynyl optionally substituted with up to 3 halogens;

V₂ and D₂ are both absent and E₂ is hydrogen or halogen; or V₂ is selected from the group consisting of NR$^c$, O or S;
D₂ is absent or selected from the group consisting of optionally substituted C₁₋₈ alkylene, optionally substituted C$_{2-8}$ alkenylene and optionally substituted C$_{2-8}$ alkynylene, said C$_{1-8}$ alkylene, C$_{2-8}$ alkenylene or C$_{2-8}$ alkynylene being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro and cyano;

E$_2$ is selected from the group consisting of hydrogen, optionally substituted 5 to 10-membered carbocyclyl and optionally substituted 5 to 10-membered heterocyclyl, said carbocyclyl or heterocyclyl being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens;

each R$^c$ is independently selected from the group consisting of hydrogen and C$_{1-6}$ alkyl;

or wherein V$_1$ and V$_2$ are each independently selected from the group consisting of NR$^c$, O or S, E$_1$ and E$_2$ are both absent, and D$_1$ and D$_2$ together form a linker group between V$_1$ and V$_2$, said linker comprising optionally substituted C$_{1-4}$ alkylene, and said alkylene being optionally substituted with 1 or 2 substituents each independently selected from the group consisting of halogen, cyano and OR$^1$;

V$_3$ is NR$^e$;

R$^e$ is hydrogen;

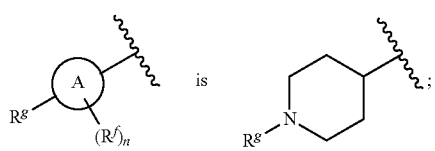 is

R$^g$ is selected from the group consisting of optionally substituted 6 to 10-membered aryl; optionally substituted 5 to 10-membered heteroaryl, optionally substituted 6 to 10-membered aryl-C$_{1-6}$ alkyl and optionally substituted 5 to 10-membered heteroaryl-C$_{1-6}$ alkyl, said aryl or heteroaryl being optionally substituted with up to 3 substituents each independently selected from the group consisting of OR$^1$, N(R$^2$)$_2$, SR$^3$, —C(O)C$_{1-4}$alkyl, —C(O)phenyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens; and R$^h$ is absent or selected from the group consisting of halogen, cyano, C$_{1-6}$ alkyl optionally substituted with up to 3 halogens, and C$_{1-6}$ alkoxy;

wherein the compound is not a compound of formula (V):

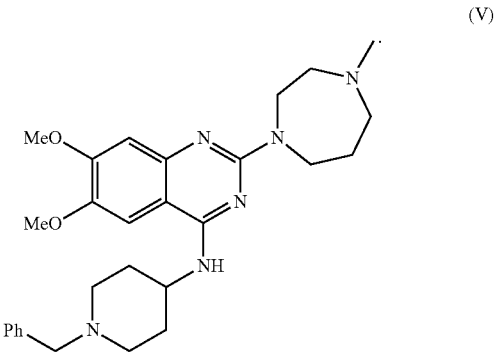 [SMILES: COc1cc2nc(N3CCCN(C)CC3)nc(NC3CCN(Cc4ccccc4)CC3)c2cc1OC]

(V)

Compounds of formula (IA), (IB), (IC) and (ID) have surprisingly been found to have activity as EZH2 inhibitors, and may thus be useful in the treatment or prophylaxis of conditions associated with EZH2 activity. This is particularly surprising in view of BIX-01294. There is no suggestion that compounds such as BIX-01294 would have activity against other targets, such as EZH2. Indeed, BIX-01294 analogues have been reported as being more than 1000-fold selective for G9a over all other HKMTases tested (21, 25, 26). BIX-01294 has also reported as having poor separation of functional potency and cell toxicity.

Compounds of the invention may also demonstrate good cell permeability properties, and/or may also have fewer off-target toxic effects (toxic effects against cancer cells are desirable whereas general cell toxicity is not).

The invention also provides a compound of the invention for use as a medicament. The invention also provides a compound of the invention for use in the treatment or prophylaxis of a condition in which inhibition of EZH2 provides a therapeutic or prophylactic effect. The invention also provides a compound of the invention for use in the treatment or prophylaxis of a cancer, wherein the compound provides a therapeutic or prophylactic effect by inhibition of EZH2.

The invention also provides a composition comprising a compound according to the invention and a pharmaceutically acceptable excipient.

The invention also provides a compound of the invention together with a further therapeutic agent, for simultaneous, sequential or separate administration.

The invention also provides a method of treatment or prophylaxis of a condition in a patient in which inhibition of EZH2 provides a therapeutic or prophylactic effect comprising administering to said patient having said condition a therapeutically effective amount of a compound of the invention.

The invention also provides a compound of the invention for the manufacture of a medicament for the treatment or prophylaxis of a condition in which inhibition of EZH2 provides a therapeutic prophylactic effect.

BRIEF DESCRIPTION OF THE DRAWINGS

FIG. 3 shows breast cancer cell line viability following administration of three representative compounds of the invention.

FIG. 3b) Western blot analysis on untreated breast cancer cell lines for endogenous EZH2 as well as H3K27me3 protein levels.

FIG. 4 shows a table (Table 1) showing effects on gene expression of selected compounds of the invention in a cell-based screen. Average qRT-PCR data for single concentration (10 µM) dose treated in triplicate. RNA levels for target genes are normalised against the housekeeping gene GAPDH and shown is the fold increase compared to the mock treated sample.

FIG. 5 shows a table (Table 2) showing numbers of genes significantly changing in gene expression following treatment with a representative compound. Numbers of significantly up-regulated and down-regulated genes upon drug treatment at time point shown and number of EZH2 target genes as defined by siRNA knock-down (from Lee et al 2011).

FIG. 6 shows a table (Supplementary table 1) providing details of primers for quantitative PCR.

FIG. 7 shows a table (Supplementary table 2) providing details of primers for chromatin immunoprecipitation (ChIP).

FIG. 8 shows a table (Supplementary table 3) providing details of siRNA sequences.

DETAILED DESCRIPTION OF THE INVENTION

Figure 1:
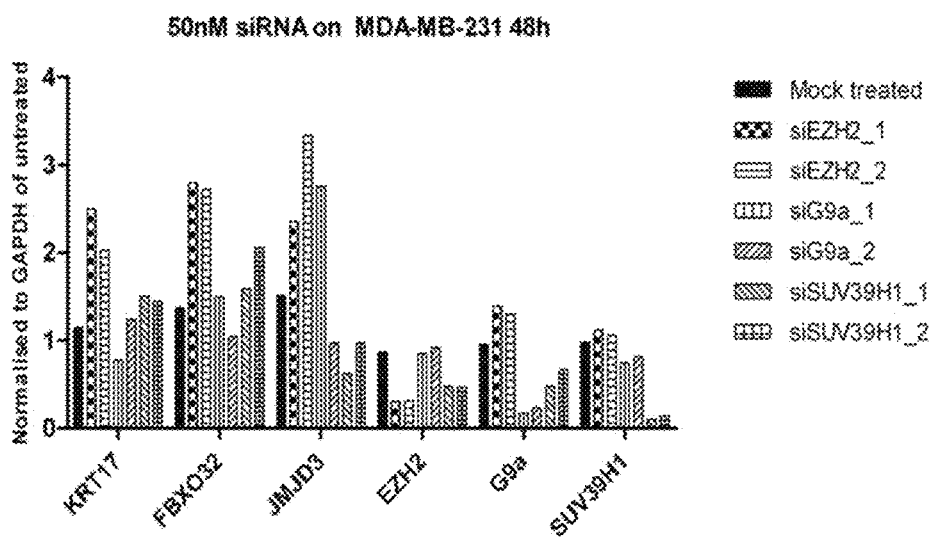
FIG. 1 shows the effects of compounds of the invention, and comparative examples, on RNA levels.

The present invention provides compounds that are EZH2 inhibitors. The term "EZH2 inhibitor" as used herein is intended to cover any moiety that inhibits the function of EZH2.

Definitions

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, sec-butyl, pentyl and hexyl groups. Among unbranched alkyl groups, there are preferred methyl, ethyl, n-propyl, iso-propyl, n-butyl groups. Among branched alkyl groups, there may be mentioned t-butyl, i-butyl, 1-ethylpropyl and 1-ethylbutyl groups.

As used herein, the term "alkylene" means both straight and branched chain divalent hydrocarbon radical. Examples of alkylene groups include methylene, ethylene, n-propylene, iso-propylene, n-butylene, t-butylene, i-butylene, sec-butylene, pentylene and hexylene groups. Among unbranched alkylene groups, there are preferred methylene, ethylene, n-propylene, iso-propylene, n-butylene groups. Among branched alkylene groups, there may be mentioned t-butylene, i-butylene, 1-ethylpropylene and 1-ethylbutylene groups.

As used herein, the term "alkenyl" means both straight and branched chain unsaturated hydrocarbon groups with at least one carbon carbon double bond. Examples of alkenyl groups include ethenyl, propenyl, butenyl, pentenyl and hexenyl. Preferred alkenyl groups include ethenyl, 1-propenyl, 2-propenyl and but-2-enyl.

As used herein, the term "alkenylene" refers to a straight or branched chain divalent hydrocarbon radical with at least one carbon carbon double bond. Examples of alkenylenes groups include ethenylene, 1-propenylene, 2-propenylene and but-2-enylene.

As used herein, the term "alkynyl" means both straight and branched chain unsaturated hydrocarbon groups with at least one carbon carbon triple bond. Examples of alkynyl groups include ethynyl, propynyl, butynyl, pentynyl and hexynyl. Preferred alkynyl groups include ethynyl, 1-propynyl and 2-propynyl.

As used herein, the term "alkynylene" means both straight and branched chain divalent hydrocarbon radical with at least one carbon carbon triple bond. Examples of alkynylene groups include ethynylene, 1-propynylene, 2-propynylene, butynylene, pentynylene and hexynylene.

As used herein, "carbocyclyl" (or carbocycle) is intended to mean any 5- to 10-membered carbon ring system, which may be saturated, partially unsaturated, or aromatic. The carbon ring system may be monocyclic or contain more than one ring (e.g. the ring system may be bicyclic). Examples of monocyclic saturated carbocycles include cyclopropyl, cyclobutyl, cyclopentyl, cyclohexyl, cycloheptyl, cyclooctyl. Examples of bicyclic saturated carbocycles include bicyclooctane, bicyclononane, bicyclodecane (decalin) and bicyclooctane. A further example of a saturated carbocycle is adamantane. Examples of monocyclic non-saturated carbocycles include cyclobutene, cyclopentene, cyclopentadiene, cyclohexene. Examples of aromatic carbocycles include phenyl and naphthyl. Further examples of carbocycles include tetrahydronaphthyl (tetralin) and indane As used herein, the term "cycloalkyl" means a saturated group in a ring system. A cycloalkyl group can be monocyclic or bicyclic. A bicyclic group may, for example, be fused or bridged. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bicyclic cycloalkyl groups include bicyclo[2.2.1]hept-2-yl. Preferably, the cycloalkyl group is monocyclic.

As used herein, the term "cycloalkylene" means a non-aromatic alicyclic divalent hydrocarbon radical, Examples of cycloalkylene include cyclopropylene, cyclobutylene and cyclopentylene. Other examples of monocyclic cycloalkyl groups are cyclohexylene and cycloheptylene. Preferably, the cycloalkylene group is monocyclic.

As used herein, the term "halogen" or "halo" means fluorine, chlorine, bromine or iodine. Fluorine, chlorine and bromine are particularly preferred.

As used herein, the term "haloalkyl" means an alkyl group having a halogen substituent, the terms "alkyl" and "halogen" being understood to have the meanings outlined above. Similarly, the term "dihaloalkyl" means an alkyl group having two halogen substituents and the term "trihaloalkyl" means an alkyl group having three halogen substituents. Examples of haloalkyl groups include fluoromethyl, chloromethyl, bromomethyl, fluoroethyl, fluoropropyl and fluorobutyl groups; examples of dihaloalkyl groups include difluoromethyl and difluoroethyl groups; examples of trihaloalkyl groups include trifluoromethyl and trifluoroethyl groups.

As used herein, the term "heterocyclyl" (or heterocycle) means an aromatic or a non-aromatic cyclic group of carbon atoms wherein from one to three of the carbon atoms is/are replaced by one or more heteroatoms independently selected from nitrogen, oxygen or sulfur. A heterocyclyl (or heterocycle) group may, for example, be monocyclic or bicyclic. In a bicyclic heterocyclyl (or heterocycle) group there may be one or more heteroatoms in each ring, or only in one of the rings. A heteroatom may be S, O or N, and is preferably O or N. Heterocyclyl groups containing a suitable nitrogen atom include the corresponding N-oxides.

Examples of monocyclic non-aromatic heterocyclyl (or heterocycle) include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl and azepanyl.

Examples of bicyclic heterocyclyl groups in which one of the rings is non-aromatic include dihydrobenzofuranyl, indanyl, indolinyl, isoindolinyl, tetrahydroisoquinolinyl, tetrahydroquinolyl and benzoazepanyl.

Examples of monocyclic aromatic heterocyclyl (or heterocycle) groups include furanyl, thienyl, pyrrolyl, oxazolyl, thiazolyl, imidazolyl, oxadiazolyl, thiadiazolyl, pyridyl, triazolyl, triazinyl, tetrazolyl, pyridazyl, isothiazolyl, isoxazolyl, pyrazinyl, pyrazolyl and pyrimidinyl.

Examples of bicyclic aromatic heterocyclyl groups (or heterocycle) include quinoxalinyl, quinazolinyl, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridiyl, pyridopyrimidinyl, isoquinolinyl and benzodroxazole.

The compounds of the invention may contain chiral (asymmetric) centers or the molecule as a whole may be chiral. The individual stereoisomers (enantiomers and diastereoisomers) and mixtures of these are within the scope of the present invention.

For the avoidance of doubt, an embodiment or preferred aspect of any one feature of the compounds of the invention may be combined with any embodiment or preferred aspect of another feature of the compounds of the invention to create a further embodiment.

In the compound of formula (IA), $R^a$ is preferably selected from the group consisting of hydrogen, $C_{1-6}$ alkyl optionally substituted with up to three halogens, optionally substituted 6 to 10-membered aryl, optionally substituted 5 to 10-membered heteroaryl, optionally substituted 6 to 10-membered aryl-$C_{1-2}$alkyl and optionally substituted 5 to 10-membered heteroaryl-$C_{1-2}$alkyl, said aryl or heteroaryl being optionally substituted with up to 3 substituents each independently selected from the group consisting of $OR^1$, $N(R^2)_2$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens; each $R^1$ is independently selected from the group consisting of hydrogen and $C_{1-4}$alkyl; each $R^2$ is independently selected from the group consisting of hydrogen, $C_{1-4}$alkyl, —$C(O)C_{1-4}$alkyl and —$S(O)_2C_{1-4}$alkyl; and each $R^3$ is independently selected from the group consisting of hydrogen and $C_{1-4}$alkyl.

More preferably, in the compound of formula (IA), $R^a$ is selected from the group consisting of hydrogen, $C_{1-6}$ alkyl, optionally substituted 6 to 10-membered aryl and optionally substituted 5 to 10-membered heteroaryl, said aryl or heteroaryl being optionally substituted with up to 3 substituents each independently selected from the group consisting of $C_{1-4}$ alkyl optionally substituted with up to 3 halogens, $C_{1-4}$alkoxy, halogen and cyano. Still more preferably, $R^a$ is selected from the group consisting of hydrogen, $C_{1-4}$ alkyl, optionally substituted phenyl and optionally substituted pyridyl, said phenyl or pyridyl being optionally substituted with up to 3 substituents each independently selected from the group consisting of $C_{1-4}$ alkyl optionally substituted with up to 3 halogens, $C_{1-4}$alkoxy, halogen and cyano. In one preferred embodiment $R^a$ is methyl. In another preferred embodiment, $R^a$ is pyridyl, preferably 2-pyridyl. In another preferred embodiment, $R^a$ is hydrogen.

In the compound of formula (IB) or (IC), W is preferably a cyclohexyl, piperidyl or piperazinyl ring. In one preferred embodiment, W is

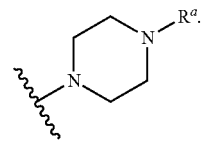

In another preferred embodiment, W is

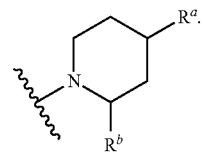

In the compound of formula (IB) or (IC), $R^a$ is preferably selected from the group consisting of hydrogen, $C_{1-6}$ alkyl optionally substituted with up to three halogens, optionally substituted 6 to 10-membered aryl and optionally substituted 5 to 10-membered heteroaryl, optionally substituted 6 to 10-membered aryl-$C_{1-2}$alkyl and optionally substituted 5 to 10-membered heteroaryl-$C_{1-2}$alkyl, said aryl or heteroaryl being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)OC$_{1-4}$alkyl, —C(O)OC$_{1-4}$trihaloalkyl, —C(O)NH$_2$, —C(O)NHC$_{1-4}$alkyl, —C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, nitro, cyano, C$_{1-4}$ alkyl optionally substituted with up to 3 halogens, C$_{2-4}$-alkenyl optionally substituted with up to 3 halogens, and C$_{2-4}$alkynyl optionally substituted with up to 3 halogens; each R$^1$ is independently selected from the group consisting of hydrogen and C$_{1-4}$alkyl; each R$^2$ is independently selected from the group consisting of hydrogen, C$_{1-4}$alkyl, —C(O)C$_{1-4}$alkyl and —S(O)$_2$C$_{1-4}$alkyl; and each R$^3$ is independently selected from the group consisting of hydrogen and C$_{1-4}$alkyl.

More preferably, in the compound of formula (IB) or (IC), R$^a$ is selected from the group consisting of hydrogen, C$_{1-6}$ alkyl, optionally substituted 6 to 10-membered aryl and optionally substituted 5 to 10-membered heteroaryl, said aryl or heteroaryl being optionally substituted with up to 3 substituents each independently selected from the group consisting of C$_{1-4}$ alkyl optionally substituted with up to 3 halogens, C$_{1-4}$alkoxy, halogen and cyano. Still more preferably, R$^a$ is selected from the group consisting of hydrogen, C$_{1-4}$ alkyl, optionally substituted phenyl and optionally substituted pyridyl, said phenyl or pyridyl being optionally substituted with up to 3 substituents each independently selected from the group consisting of C$_{1-4}$ alkyl optionally substituted with up to 3 halogens, C$_{1-4}$alkoxy, halogen and cyano. In one preferred embodiment R$^a$ is methyl. In another preferred embodiment, R$^a$ is pyridyl, preferably 2-pyridyl. In another preferred embodiment, R$^a$ is hydrogen.

In the compound of formula (IB) or (IC), preferably each R$^{ip}$ is independently selected from the group consisting of hydrogen, C$_{1-6}$ alkyl, optionally substituted 6 to 10-membered aryl and optionally substituted 5 to 10-membered heteroaryl, said aryl or heteroaryl being optionally substituted with up to 3 substituents each independently selected from the group consisting of C$_{1-4}$ alkyl optionally substituted with up to 3 halogens, C$_{1-4}$alkoxy, halogen and cyano. More preferably, each R$^b$ is independently selected from the group consisting of hydrogen and C$_{1-4}$ alkyl. In one preferred embodiment, one R$^b$ group is methyl and the other R$^b$ groups are hydrogen. In another preferred embodiment, each R$^b$ is hydrogen.

In one preferred embodiment of the compound of formula (IB) or (IC), W is

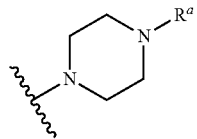

and R$^a$ is selected from the group consisting of hydrogen, C$_{1-4}$ alkyl, optionally substituted phenyl and optionally substituted pyridyl, said phenyl or pyridyl being optionally substituted with up to 3 substituents each independently selected from the group consisting of C$_{1-4}$ alkyl optionally substituted with up to 3 halogens, C$_{1-4}$alkoxy, halogen and cyano; In one preferred embodiment R$^a$ is methyl. In another preferred embodiment, R$^a$ is pyridyl, preferably 2-pyridyl. In another preferred embodiment, R$^a$ is hydrogen.

In another preferred embodiment of the compound of formula (IB) or (IC), W is

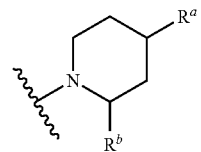

R$^a$ is hydrogen or C$_{1-4}$ alkyl, and R$^b$ is hydrogen or C$_{1-4}$ alkyl. In one preferred embodiment R$^a$ is hydrogen and R$^b$ is hydrogen. In another preferred embodiment, R$^a$ is hydrogen and R$^b$ is C$_{1-4}$alkyl (e.g. methyl).

In the compound of formula (IB), preferably V$_1$ is O; D$_1$ is optionally substituted C$_{1-6}$ alkylene, said C$_{1-6}$alkylene being optionally substituted with up to 3 substituents each independently selected from the group consisting of OR$^1$ and cyano; and E$_1$ is hydrogen or optionally substituted 6 to 10-membered aryl, said aryl being optionally substituted with up to 3 substituents each independently selected from the group consisting of C$_{1-4}$ alkyl optionally substituted with up to 3 halogens, C$_{1-4}$alkoxy, halogen, hydroxy and cyano. Most preferably, V$_1$ is O; D$_1$ is C$_{1-2}$ alkylene; and E$_1$ is hydrogen. In one preferred embodiment, V$_1$ is O; D$_1$ is methylene; and E$_1$ is hydrogen.

In the compound of formula (IA) or (IC), preferably V$_1$ is O; D$_1$ is optionally substituted C$_{1-6}$ alkylene, said C$_{1-6}$alkylene being optionally substituted with up to 3 substituents each independently selected from the group consisting of OR$^1$ and cyano; and E$_1$ is hydrogen or optionally substituted 6 to 10-membered aryl, said aryl being optionally substituted with up to 3 substituents each independently selected from the group consisting of C$_{1-4}$ alkyl optionally substituted with up to 3 halogens, C$_{1-4}$alkoxy, halogen, hydroxy and cyano. Most preferably, V$_1$ is O; D$_1$ is C$_{1-2}$ alkylene; and E$_1$ is hydrogen. In one preferred embodiment, V$_1$ is O; D$_1$ is methylene; and E$_1$ is hydrogen.

In the compound of formula (IC), preferably R$^g$ is selected from the group consisting of optionally substituted 6 to 10-membered aryl and optionally substituted 6 to 10-membered aryl-C$_{1-2}$ alkyl, said aryl being optionally substituted with up to 3 substituents each independently selected from the group consisting of OR$^1$, N(R$^2$)$_2$, SR$^3$, —C(O)C$_{1-4}$alkyl, —C(O)C$_{1-4}$trihaloalkyl, —C(O)NH$_2$, —C(O)NHC$_{1-4}$alkyl, C(O)N(C$_{1-4}$alkyl)$_2$, —S(O)C$_{1-4}$alkyl, —S(O)$_2$C$_{1-4}$alkyl, —S(O)$_2$NH$_2$, —S(O)$_2$NHC$_{1-4}$alkyl, —S(O)$_2$N(C$_{1-4}$alkyl)$_2$, halogen, cyano and C$_{1-4}$ alkyl optionally substituted with up to 3 halogens. More preferably, R$^g$ is optionally substituted 6 to 10-membered aryl-C$_{1-2}$ alkyl, said aryl being optionally substituted with up to 3 substituents each independently selected from the group consisting of hydroxyl, C$_{1-4}$ alkoxy, halogen, cyano and C$_{1-4}$ alkyl optionally substituted by up to three halogens.

In the compounds of formula (IA) or (IB), preferably V$_3$ is NR$^e$;

R$^e$ is hydrogen;

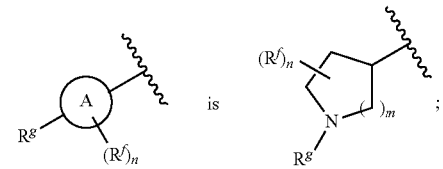

m is an integer of from 0 to 2;
n is an integer of from 0 to 2;

$R^f$ is optionally substituted $C_{1-6}$ alkyl, said alkyl being optionally substituted with up to 3 substituents each independently selected from the group consisting of $OR^1$, halogen and cyano; and $R^g$ is selected from the group consisting of hydrogen, optionally substituted $C_{1-8}$ alkyl, optionally substituted 5 to 10-membered carbocyclyl, optionally substituted 5 to 10-membered heterocyclyl, optionally substituted 5 to 10-membered carbocyclyl-$C_{1-6}$ alkyl and optionally substituted 5 to 10-membered heterocyclyl-$C_{1-6}$ alkyl, said alkyl being optionally substituted with up to 3 substituents each independently selected from the group consisting of $OR^1$, $N(R^2)_2$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro and cyano, and said carbocyclyl or heterocyclyl being optionally substituted with up to 3 substituents each independently selected from the group consisting of $OR^1$, $N(R^2)_2$, $SR^3$, —$C(O)C_{1-4}$alkyl, —$C(O)$phenyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens.

More preferably, in the compounds of formula (IA) or (IB), $V_3$ is $NR^e$; $R^e$ is hydrogen;

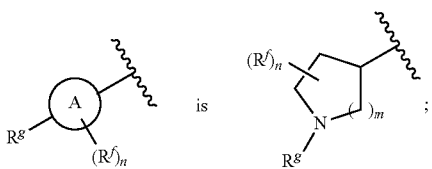

$R^g$ is selected from the group consisting of optionally substituted 6 to 10-membered aryl; optionally substituted 5 to 10-membered heteroaryl, optionally substituted 6 to 10-membered aryl-$C_{1-6}$ alkyl and optionally substituted 5 to 10-membered heteroaryl-$C_{1-6}$ alkyl, said aryl or heteroaryl being optionally substituted with up to 3 substituents each independently selected from the group consisting of $OR^1$, $N(R^2)_2$, $SR^3$, —$C(O)C_{1-4}$alkyl, —$C(O)$phenyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens. Still more preferably, $R^g$ is selected from the group consisting of optionally substituted 6 to 10-membered aryl and optionally substituted 6 to 10-membered aryl-$C_{1-2}$ alkyl, said aryl being optionally substituted with up to 3 substituents each independently selected from the group consisting of $OR^1$, $N(R^2)_2$, $SR^3$, —$C(O)C_{1-4}$alkyl, —$C(O)C_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, cyano and $C_{1-4}$ alkyl optionally substituted with up to 3 halogens. Yet more preferably, $R^g$ is optionally substituted 6 to 10-membered aryl-$C_{1-2}$ alkyl, said aryl being optionally substituted with up to 3 substituents each independently selected from the group consisting of hydroxyl, $C_{1-4}$ alkoxy, halogen, cyano and $C_{1-4}$ alkyl optionally substituted by up to three halogens.

In an alternative, but still preferred embodiment of the compounds of formula (IA) or (IB),

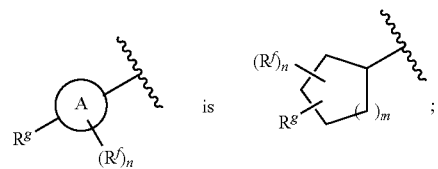

m is an integer of from 0 to 2;

n is an integer of from 0 to 2;

$R^f$ is optionally substituted $C_{1-6}$ alkyl, said alkyl being optionally substituted with up to 3 substituents each independently selected from the group consisting of $OR^1$, halogen and cyano; and $R^g$ is selected from the group consisting of hydrogen, optionally substituted $C_{1-8}$ alkyl, optionally substituted 5 to 10-membered carbocyclyl, optionally substituted 5 to 10-membered heterocyclyl, optionally substituted 5 to 10-membered carbocyclyl-$C_{1-6}$ alkyl and optionally substituted 5 to 10-membered heterocyclyl-$C_{1-6}$ alkyl, said alkyl being optionally substituted with up to 3 substituents each independently selected from the group consisting of $OR^1$, $N(R^2)_2$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro and cyano, and said carbocyclyl or heterocyclyl being optionally substituted with up to 3 substituents each independently selected from the group consisting of $OR^1$, $N(R^2)_2$, $SR^3$, —$C(O)C_{1-4}$alkyl, —$C(O)$phenyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens.

In the compounds of formula (IA), (IB) or (IC), preferably $V_2$ is O; $D_2$ is optionally substituted $C_{1-6}$ alkylene, said $C_{1-6}$alkylene being optionally substituted with up to 3 substituents each independently selected from the group consisting of $OR^1$ and cyano; and $E_2$ is hydrogen or optionally substituted 6 to 10-membered aryl, said aryl being optionally substituted with up to 3 substituents each independently selected from the group consisting of $C_{1-4}$ alkyl optionally substituted with up to 3 halogens, $C_{1-4}$alkoxy, halogen, hydroxy and cyano. Most preferably, $V_2$ is O; $D_2$ is $C_{1-6}$ alkylene; and $E_2$ is hydrogen. Most preferably, $V_2$ is O; $D_2$ is $C_{1-2}$ alkylene; and $E_2$ is hydrogen. In one preferred embodiment, $V_2$ is O; $D_2$ is methylene; and $E_2$ is hydrogen.

In the compounds of formula (IA), (IB) or (IC), preferably $R^h$ is absent.

In one preferred embodiment, W is

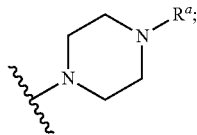

$R^a$ is selected from the group consisting of hydrogen, $C_{1-8}$ alkyl optionally substituted with up to three halogens, $C_{2-8}$ alkenyl, alkynyl, optionally substituted 5 to 10-membered carbocyclyl, optionally substituted 5 to 10-membered heterocyclyl, optionally substituted 5 to 10-membered carbocyclyl-$C_{1-6}$ alkyl and optionally substituted 5 to 10-membered heterocyclyl-$C_{1-6}$ alkyl, said carbocyclyl or heterocyclyl being optionally substituted with up to 3 substituents each independently selected from the group consisting of $OR^1$, $N(R^2)_2$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

each $R^1$ is independently selected from the group consisting of hydrogen, $C_{1-4}$alkyl, $C_{1-4}$trifluoroalkyl, —$C(O)C_{1-4}$alkyl, and —$C(O)C_{1-4}$trihaloalkyl;

each $R^2$ is independently selected from the group consisting of hydrogen, $C_{1-4}$alkyl, $C_{1-4}$trifluoroalkyl, —$C(O)C_{1-4}$alkyl, —$C(O)C_{1-4}$trihaloalkyl, —$S(O)_2C_{1-4}$alkyl, and —$S(O)_2C_{1-4}$trihaloalkyl;

each $R^3$ is independently selected from the group consisting of hydrogen, $C_{1-4}$alkyl, $C_{1-4}$trifluoroalkyl, —$C(O)C_{1-4}$alkyl, and —$C(O)C_{1-4}$trihaloalkyl;

either $V_1$ and $D_1$ are both absent and $E_1$ is hydrogen or halogen; or $V_1$ is selected from the group consisting of $NR^c$, O or S;

$D_1$ is absent or selected from the group consisting of optionally substituted $C_{1-8}$ alkylene, optionally substituted $C_{2-8}$ alkenylene and optionally substituted $C_{2-8}$ alkynylene, said $C_{1-8}$ alkylene, $C_{2-8}$ alkenylene or $C_{2-8}$ alkynylene being optionally substituted with up to 3 substituents each independently selected from the group consisting of $OR^1$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro and cyano;

$E_1$ is selected from the group consisting of hydrogen and optionally substituted 5 to 10-membered carbocyclyl, said carbocyclyl being optionally substituted with up to 3 substituents each independently selected from the group consisting of $OR^1$, $SR^3$, —$C(O)C_{1-4}$alkyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;

$V_3$ is $NR^e$;

$R^e$ is hydrogen;

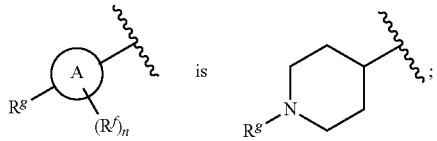

and $R^g$ is selected from the group consisting of optionally substituted 6 to 10-membered aryl, optionally substituted 5 to 10-membered heteroaryl, optionally substituted 6 to 10-membered aryl-$C_{1-6}$ alkyl and optionally substituted 5 to 10-membered heteroaryl-$C_{1-6}$ alkyl, said aryl or heteroaryl being optionally substituted with up to 3 substituents each independently selected from the group consisting of $OR^1$, $N(R^2)_2$, $SR^3$, —$C(O)C_{1-4}$alkyl, —$C(O)$phenyl, —$C(O)C_{1-4}$trihaloalkyl, —$C(O)OC_{1-4}$alkyl, —$C(O)OC_{1-4}$trihaloalkyl, —$C(O)NH_2$, —$C(O)NHC_{1-4}$alkyl, —$C(O)N(C_{1-4}$alkyl$)_2$, —$S(O)C_{1-4}$alkyl, —$S(O)_2C_{1-4}$alkyl, —$S(O)_2NH_2$, —$S(O)_2NHC_{1-4}$alkyl, —$S(O)_2N(C_{1-4}$alkyl$)_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens.

In another preferred embodiment,
W is

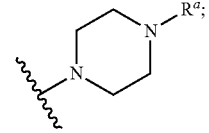

$R^a$ is selected from the group consisting of $C_{1-6}$ alkyl, optionally substituted 6 to 10-membered aryl and optionally substituted 5 to 10-membered heteroaryl, said aryl or heteroaryl being optionally substituted with up to 3 substituents each independently selected from the group consisting of $C_{1-4}$ alkyl optionally substituted with up to 3 halogens, $C_{1-4}$alkoxy, halogen and cyano;

either $V_1$ and $D_1$ are both absent and $E_1$ is hydrogen or halogen; or $V_1$ is O; $D_1$ is $C_{1-6}$ alkylene, said $C_{1-6}$alkylene being optionally substituted with up to 3 substituents each independently selected from the group consisting of $OR^1$ and cyano; and $E_1$ is hydrogen or optionally substituted 6 to 10-membered aryl, said aryl being optionally substituted with up to 3 substituents each independently selected from the group consisting of $C_{1-4}$ alkyl optionally substituted with up to 3 halogens, $C_{1-4}$ alkoxy, halogen, hydroxy and cyano;

$V_3$ is $NR^e$;

$R^e$ is hydrogen;

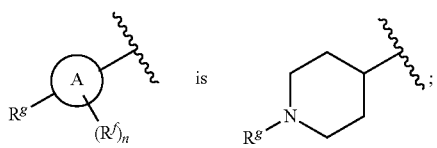

and $R^g$ is optionally substituted 6 to 10-membered aryl-$C_{1-2}$ alkyl, said aryl being optionally substituted with up to 3 substituents each independently selected from the group consisting of $C_{1-4}$ alkyl optionally substituted by up to three halogens, hydroxyl, $C_{1-4}$ alkoxy, halogen and cyano;
$V_2$ is O; $D_2$ is $C_{1-6}$ alkylene; $E_2$ is hydrogen; and $R^h$ is absent.

In another preferred embodiment, W is

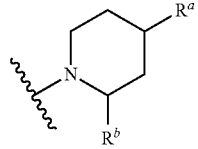

$R^a$ is hydrogen or $C_{1-4}$ alkyl; $R^b$ is hydrogen or $C_{1-4}$ alkyl; either $V_1$ and $D_1$ are both absent and $E_1$ is hydrogen or halogen; or
$V_1$ is selected from the group consisting of $NR^c$, O or S; $D_1$ is absent or selected from the group consisting of optionally substituted $C_{1-8}$ alkylene, optionally substituted $C_{2-8}$ alkenylene and optionally substituted $C_{2-8}$ alkynylene, said $C_{1-8}$ alkylene, $C_{2-8}$ alkenylene or $C_{2-8}$ alkynylene being optionally substituted with up to 3 substituents each independently selected from the group consisting of $OR^1$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2$$C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro and cyano;
$E_1$ is selected from the group consisting of hydrogen and optionally substituted 5 to 10-membered carbocyclyl, said carbocyclyl being optionally substituted with up to 3 substituents each independently selected from the group consisting of $OR^1$, $SR^3$, —C(O)$C_{1-4}$alkyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2$$C_{1-4}$alkyl, —S(O)$_2$NH$_2$, —S(O)$_2$NH$C_{1-4}$alkyl, —S(O)$_2$N($C_{1-4}$alkyl)$_2$, halogen, nitro, cyano, $C_{1-4}$ alkyl optionally substituted with up to 3 halogens, $C_{2-4}$-alkenyl optionally substituted with up to 3 halogens, and $C_{2-4}$alkynyl optionally substituted with up to 3 halogens;
$V_3$ is $NR^e$;
$R^e$ is hydrogen;

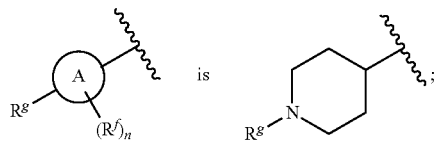

and
$R^g$ is selected from the group consisting of optionally substituted 6 to 10-membered aryl; optionally substituted 5 to 10-membered heteroaryl, optionally substituted 6 to 10-membered aryl-$C_{1-6}$ alkyl and optionally substituted 5 to 10-membered heteroaryl-$C_{1-6}$ alkyl, said aryl or heteroaryl being optionally substituted with up to 3 substituents each independently selected from the group consisting of $OR^1$, $N(R^2)_2$, $SR^3$, —C(O)$C_{1-4}$alkyl, —C(O)phenyl, —C(O)$C_{1-4}$trihaloalkyl, —C(O)O$C_{1-4}$alkyl, —C(O)O$C_{1-4}$trihaloalkyl, —C(O)NH$_2$, —C(O)NH$C_{1-4}$alkyl, —C(O)N($C_{1-4}$alkyl)$_2$, —S(O)$C_{1-4}$alkyl, —S(O)$_2$$C_{1-4}$alkyl, —S(O)$_2$NH$_2$, —S(O)$_2$NH$C_{1-4}$ alkyl, —S(O)$_2$N($C_{1-4}$alkyl)$_2$, halogen, nitro, cyano, $C_{1-4}$ alkyl optionally substituted with up to 3 halogens, $C_{2-4}$alkenyl optionally substituted with up to 3 halogens, and $C_{2-4}$alkynyl optionally substituted with up to 3 halogens.

In another preferred embodiment, W is

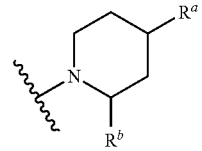

$R^a$ is hydrogen or $C_{1-4}$ alkyl; $R^b$ is hydrogen or $C_{1-4}$ alkyl; either $V_1$ and $D_1$ are both absent and $E_1$ is hydrogen or halogen; or
$V_1$ is O; $D_1$ is $C_{1-6}$ alkylene, said $C_{1-6}$alkylene being optionally substituted with up to 3 substituents each independently selected from the group consisting of $OR^1$ and cyano; and $E_1$ is hydrogen or optionally substituted 6 to 10-membered aryl, said aryl being optionally substituted with up to 3 substituents each independently selected from the group consisting of $C_{1-4}$ alkyl optionally substituted with up to 3 halogens, $C_{1-4}$alkoxy, halogen, hydroxy and cyano;
$V_3$ is $NR^e$;
$R^e$ is hydrogen;

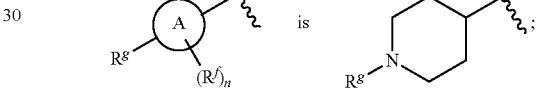

and
$R^g$ is optionally substituted 6 to 10-membered aryl-$C_{1-2}$ alkyl, said aryl being optionally substituted with up to 3 substituents each independently selected from the group consisting of $C_{1-4}$ alkyl optionally substituted by up to three halogens, hydroxyl, $C_{1-4}$ alkoxy, halogen and cyano;
$V_2$ is O; $D_2$ is $C_{1-6}$ alkylene; $E_2$ is hydrogen; and $R^h$ is absent.

Preferred compounds of the invention include the following compounds, and their salts, especially their pharmaceutically acceptable salts:

N-(1-Benzylpiperidin-4-yl)-6,7-dimethoxy-2-(piperidin-1-yl)quinazolin-4-amine

N-(1-benzylpiperidin-4-yl)-6,7-dimethoxy-2-(4-methylpiperazin-1-yl)quinazolin-4-amine N-(1-benzylpiperidin-4-yl)-6,7-dimethoxy-2-(2-methylpiperidin-1-yl)quinazolin-4-amine N-(1-benzylpiperidin-4-yl)-6,7-dimethoxy-2-[4-(pyridin-2-yl)piperazin-1-yl]quinazolin-4-amine In another aspect, the invention provides the compound (ID)

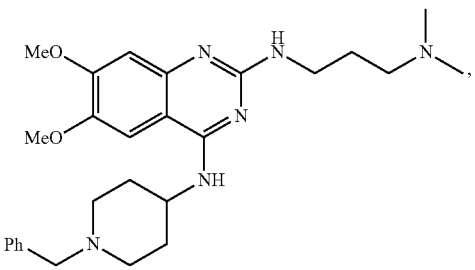 [SMILES: COc1cc2nc(NCCCN(C)C)nc(NC3CCN(Cc4ccccc4)CC3)c2cc1OC]

or a pharmaceutically acceptable salt thereof. Although less preferred, compound (ID) may still have activity so as to be useful in cancer therapy.

Preferred compounds of the invention include the compounds of formula (IA), (IB), (IC) and (ID) specifically mentioned in the Examples herein, and their salts, especially their pharmaceutically acceptable salts.

As mentioned above, the compounds of the invention have activity as EZH2 inhibitors, and may thus be used in diseases or disorders associated with EZH2 activity. Accordingly, there is provided a compound of formula (IA), (IB), (IC) or (ID) for use as a medicament. The invention also provides a compound of formula (IIIB) or (IVB)

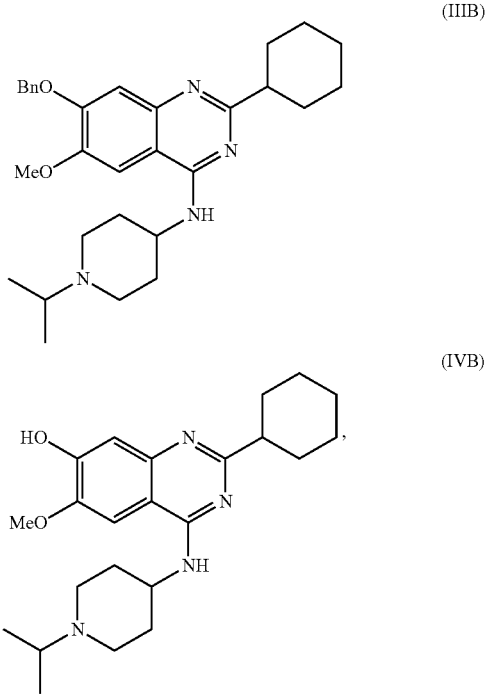

or a pharmaceutically acceptable salt thereof, for use as a medicament. There is also provided a compound of the invention for use in the treatment or prophylaxis of a condition in which inhibition of EZH2 provides a therapeutic or prophylactic effect. In a preferred embodiment, the condition is a cancer, and the compound provides a therapeutic or prophylactic effect by inhibition of EZH2.

Because of the selectivity of the compounds of the invention to EZH2, it is expected that they may be used for treatment of conditions (diseases/disorders) with fewer side-effects than less selective compounds. For example, use of the compounds of the invention may avoid or at least reduce side effects associated with therapies targeting G9a. It is also expected that the compounds of the invention will find particular utility in targeting conditions (diseases/disorders) in particular patient populations, e.g. where EZH2-mediated activation of H3K27me3 is a critical or at least significant component of disease progression.

Accordingly, compounds of the invention preferably find use in the treatment of a cancer in a patient population which expresses a level of EZH2 and/or H3K27me3 associated with having said cancer. Whether a patient expresses a level of EZH2 and/or H3K27me3 associated with having a cancer may be assessed by standard methods, for example PCR or other gene expression assay, or by direct detection of EZH2 or H3K27me3, for example an antibody detection assay such as an ELISA.

In one embodiment, the invention provides a method of treating cancer in a patient having said cancer comprising a) assessing if said patient expresses a level of EZH2 and/or H3K27me3 associated with having said cancer; and b) administering to a patient found to express said level of EZH2 and/or H3K27me3 associated with having said cancer a therapeutically effective amount of a compound of the invention.

Other methods that may be used to identify patient populations particularly responsive to the compounds of the invention include monitoring global levels of histone modification (i.e. patient populations having a cancer who are responsive to therapies targeting EZH2 may express different global levels of histone modification). Gene expression profiling focused on EZH2 target genes may also be used to identify patient populations that may be particular suitable for treatment with compounds of the invention (e.g. using gene microarray expression techniques). Thus, compounds of the invention preferably find use in the treatment of a cancer in a patient population which expresses a level of EZH2 target genes associated with having said cancer.

Preferably, compounds of the invention find use in the treatment of a cancer in a patient population in which G9a and/or H3K9me2 levels are not associated with having said cancer. Preferably, compounds of the invention find use in the treatment of a cancer in a patient population which is non-responsive or does not respond completely to treatment with an inhibitor of G9a.

The invention also provides a method of treatment or prophylaxis of a condition in a patient in which inhibition of EZH2 provides a therapeutic or prophylactic effect comprising administering to the patient having said condition a therapeutically effective amount of a compound according to the invention.

The invention also provides the use of a compound according to the invention for the manufacture of a medicament for the treatment or prophylaxis of a condition in which inhibition of EZH2 provides a therapeutic prophylactic effect.

Clinical conditions (i.e. diseases/disorders) in which inhibition of EZH2 may provide a therapeutic or prophylactic effect include cancers, preferably a cancer selected from the group consisting of ovarian cancer, breast cancer, prostate cancer, liver cancer, skin cancer, bladder cancer, head and neck cancer, glioblastoma, renal cancer, esophageal cancer, colon cancer, non-small cell lung cancer, small cell lung cancer, myelodisplastic syndrome, multiple myeloma, acute myeloid leukemia, chronic myeloid leukaemia. Compounds of the invention may also be useful in treating or preventing neurodegenerative diseases, such as Huntington's disease. Compounds of the invention may also be useful in treating viral conditions, such as HIV.

Depending upon the substituents present in compounds of the invention, the compounds may form esters, amides, carbamates and/or salts. Salts of compounds of the invention which are suitable for use in medicine are those wherein a counterion is pharmaceutically acceptable. However, salts having non-pharmaceutically acceptable counterions are within the scope of the present invention, for example, for use as intermediates in the preparation of the compounds of the invention and their pharmaceutically acceptable salts, and physiologically functional derivatives. By the term "physiologically functional derivative" is meant a chemical derivative of a compound of the invention having the same physiological function as the free compound of the invention, for example, by being convertible in the body thereto. Esters, amides and carbamates are examples of physiologically functional derivatives.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

Compounds of the invention may have an appropriate group converted to an ester, an amide or a carbamate. Typical ester and amide and carbamate groups formed from a hydroxyl or amine group in the compound of the formula I include —OC(O)$C_{1-6}$alkyl, —NHC(O)$C_{1-6}$alkyl, —NHC(O)O$C_{1-6}$alkyl —OS(O)$_2$$C_{1-6}$alkyl, and NHS(O)$_2$$C_{1-6}$alkyl Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al., *Pharmaceutical Research*, 1995. 12(7): p. 954-954, and Water-Insoluble Drug Formulation, $2^{nd}$ ed. R. Liu, CRC Press, page 553, which are incorporated herein by reference. Accordingly, it will be understood by the skilled person that the compounds of the invention, as well as esters, amides, carbamates and/or salts thereof may therefore be present in the form of solvates. Solvates of compounds of the invention which are suitable for use in medicine are those wherein the associated solvent is pharmaceutically acceptable. For example, a hydrate is an example of a pharmaceutically acceptable solvate. However, solvates having non-pharmaceutically acceptable associated solvents may find use as intermediates in the preparation of the compounds of the invention and their pharmaceutically acceptable esters, amides, carbamates and/or salts thereof.

A compound which, upon administration to the recipient, is capable of being converted into a compound of the invention as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 50 mg per kg of body weight per day (mg/kg/day), more preferably 0.1 mg per kg of body weight per day (mg.kg/day) to 30 mg per kg of body weight per day (mg/kg/day), still more preferably, 0.1 mg per kg of body weight per day (mg/kg/day) to 20 mg per kg of body weight per day (mg/kg/day), yet more preferably 0.1 mg per kg of body weight per day (mg/kg/day) to 10 mg per kg of body weight per day (mg/kg/day), and most preferably 0.1 mg per kg of body weight per day (mg/kg/day) to 5.0 mg per kg of body weight per day (mg/kg/day), for adult humans. In one embodiment, the oral dosage is from 5 to 30 mg/kg/day for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, 500, 1000 or 2000 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion.

Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

While it is possible for the active ingredient to be administered alone, it is preferable for it to be present in a pharmaceutical formulation or composition. Accordingly, the invention provides a pharmaceutical formulation or composition comprising a compound according to the invention, and a pharmaceutically acceptable diluent, excipient or carrier (collectively referred to herein as "carrier" materials). Pharmaceutical compositions of the invention may take the form of a pharmaceutical formulation as described below.

The pharmaceutical formulations according to the invention include those suitable for oral, parenteral (including subcutaneous, intradermal, intramuscular, intravenous [bolus or infusion], and intraarticular), inhalation (including fine particle dusts or mists which may be generated by means of various types of metered dose pressurized aerosols), nebulizers or insufflators, rectal, intraperitoneal and topical (including dermal, buccal, sublingual, and intraocular) administration, although the most suitable route may depend upon, for example, the condition and disorder of the recipient. Preferably, the pharmaceutical formulations according to the invention are those suitable for intravenous, intraperitoneal, oral or subcutaneous administration. Those administration routes are preferred.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of the invention can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like. The compounds of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient in a medicament, it is also possible for the compound to be used in combination with one or more further active agents. Accordingly there is provided a compound of the invention, together with a further therapeutic agent, for simultaneous, sequential or separate administration. Such further active agents may be further compounds according to the invention, or they may be different therapeutic agents. Preferably, the further active agent is an agent that is useful for treating cancer (e.g. ovarian cancer, breast cancer, prostate cancer, liver cancer, skin cancer, bladder cancer and/or head and neck cancer). The further active agent may, for example, be an HDAC (histone deacetylase) inhibitor, a cytotoxic agent useful in chemotherapy (such as carboplatin, caelyx or gemcitabine), a TK (tyrosine kinase) inhibitor or a VEGF (vascular endothelial growth factor) inhibitor.

The compounds of the present invention can be used in combination with other agents useful for the treatment or prophylaxis of a condition (e.g. disease or disorder) in which inhibition of EZH2 provides a therapeutic or prophylactic effect. The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of the compounds of this invention with other agents useful for treating or prophylaxis of a condition in which inhibition of EZH2 provides a therapeutic or prophylactic effect includes in principle any combination with any pharmaceutical composition useful for treating or prophylaxis of a condition in which inhibition of EZH2 provides a therapeutic or prophylactic effect.

The above other therapeutic agents, when employed in combination with the compounds of the present invention, may be used, for example, in those amounts indicated in the Physicians' Desk Reference (PDR) or as otherwise determined by one of ordinary skill in the art.

Where the compounds of the invention are utilized in combination with one or more other therapeutic agent(s), either concurrently or sequentially, the following combination ratios and dosage ranges are preferred:

When combined with a second of further therapeutic agent, the compounds of formula (I) may be employed in a weight ratio to the additional agent within the range from about 10:1 to about 1:10.

The compounds of the invention as described above also find use, optionally in labelled form, as a diagnostic agent for the diagnosis of a condition in which inhibition of EZH2 provides a therapeutic or prophylactic effect. For example, such a compound may be radioactively labelled. Alternatively, such a compound may be fluorescently labelled.

The compounds of the invention as described above, optionally in labelled form, also find use as a reference compound in methods of discovering other inhibitors of EZH2. Thus, the invention provides a method of discovering a inhibitor of EZH2 which comprises use of a compound of the invention or a compound of the invention in labelled form, as a reference compound.

Numerous synthetic routes to the compounds of the present invention can be devised by any person skilled in the art and the exemplified synthetic routes described below do not limit the invention. Many methods exist in the literature for the synthesis of nitrogen-containing heterocycles, for example: *Heterocyclic Chemistry*, Joule, J. A.; Mills, K. 2000. A number of possible synthetic routes are exemplified below. Where appropriate, any initially produced compound according to the invention can be converted into another compound according to the invention by known methods.

General Method I

The following general method can be used to prepare compounds of formula (IA) wherein W is

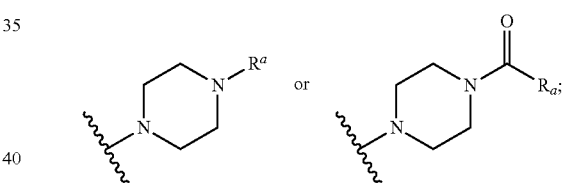

and $V_3$ is NH;
compounds of formula (IB) wherein X is N and $V_3$ is NH;
compounds of formula (IC) wherein X is N and $V_3$ is NH;
and compounds of formula (ID) wherein X is N and $V_3$ is NH.

In particular, the following general method can be used to prepare compounds of formula (IA), (IB) or (IC) wherein either W is

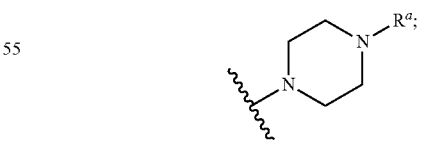

and $R^a$ is selected from the group consisting of $C_{1-6}$ alkyl, optionally substituted 6 to 10-membered aryl and optionally substituted 5 to 10-membered heteroaryl, said aryl or heteroaryl being optionally substituted with up to 3 substituents each independently selected from the group consisting of $C_{1-4}$ alkyl optionally substituted with up to 3 halogens, $C_{1-4}$alkoxy, halogen and cyano;

or W is

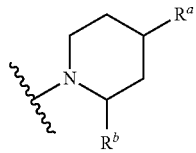

$R^a$ is hydrogen or $C_{1-4}$ alkyl; and $R^b$ is hydrogen or $C_{1-4}$ alkyl;
either $V_1$ and $D_1$ are both absent and $E_1$ is hydrogen or halogen; or
$V_1$ is O; $D_1$ is $C_{1-6}$ alkylene, said $C_{1-6}$alkylene being optionally substituted with up to 3 substituents each independently selected from the group consisting of $OR^1$ and cyano; and $E_1$ is hydrogen or optionally substituted 6 to 10-membered aryl, said aryl being optionally substituted with up to 3 substituents each independently selected from the group consisting of $C_{1-4}$ alkyl optionally substituted with up to 3 halogens, $C_{1-4}$alkoxy, halogen, hydroxy and cyano;
$V_3$ is $NR^e$;
$R^e$ is hydrogen;

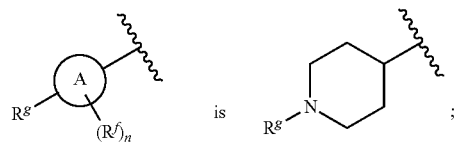

and
$R^g$ is optionally substituted 6 to 10-membered aryl-$C_{1-2}$ alkyl, said aryl being optionally substituted with up to 3 substituents each independently selected from the group consisting of $C_{1-4}$ alkyl optionally substituted by up to three halogens, hydroxyl, $C_{1-4}$ alkoxy, halogen and cyano; $V_2$ is O; $D_2$ is $C_{1-6}$ alkylene; $E_2$ is hydrogen; and $R^h$ is absent.

General Procedure for the First Displacement Reaction

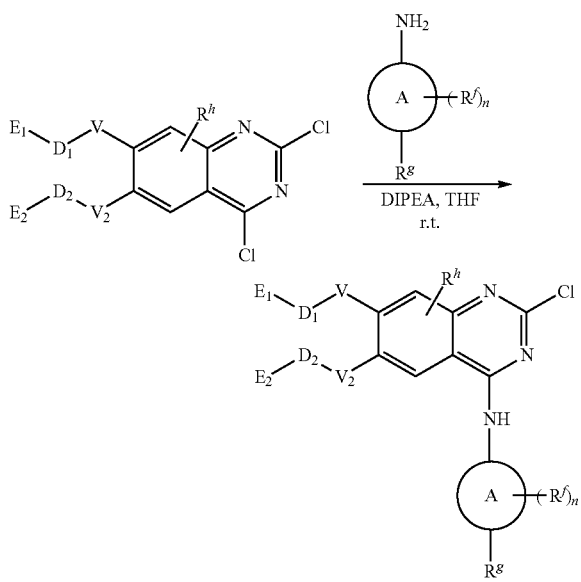

Method 1:
A mixture of the appropriate 2,4-dichloroquinazoline (1 eq.), primary amine (1.5 eq.) and DIPEA (3 eq.) in dry THF was stirred overnight at room temperature and then concentrated under reduced pressure. The crude product was purified by flash chromatography (DCM/MeOH 100:0 to 96:4) to afford the expected 4-substituted quinazoline.

General Procedure for the Second Displacement Reaction

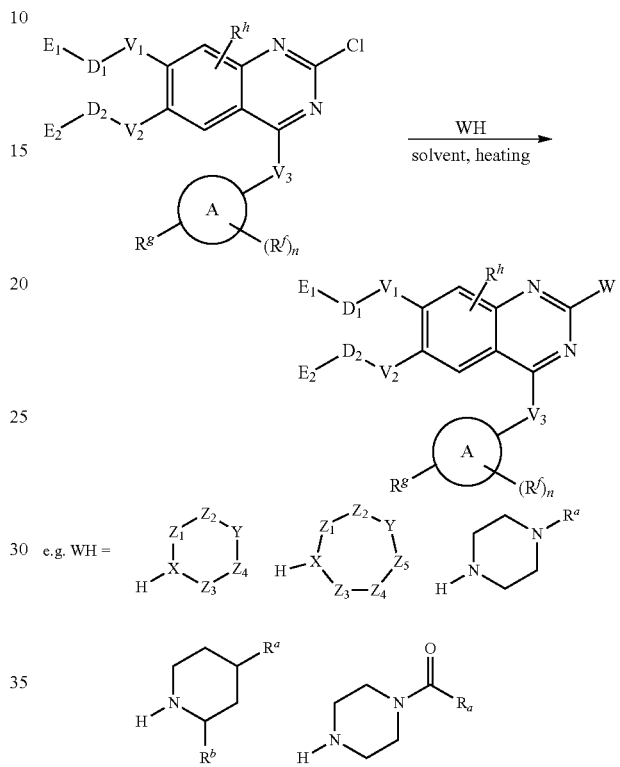

Method 2:
Secondary amine (10 equiv) was added to the 2-chloroquinazoline (1 equiv) in i-propanol. A catalytic amount of 4M HCl in dioxane was then added. The contents were refluxed at 130° C. for 16 hours. After completion of reaction (monitored by LCMS), contents were diluted with EtOAc and extracted with water. The organic layer was washed twice with saturated sodium bicarbonate solution, organic layer was concentrated under vacuum and the crude product obtained was purified by preparative HPLC or by flash chromatography (DCM/MeOH (7N $NH_3$) 99:1 to 95:5) to afford the expected substituted quinazoline.

Method 3:
Secondary amine (10 equiv) was added to the 2-chloroquinazoline (1 equiv) in t-butanol. The reaction mixture was refluxed at 130° C. for 16 h. After completion of reaction (monitored by LCMS), reaction mixture was diluted with EtOAc and extracted with water. The organic layer was washed twice with saturated bicarbonate solution and concentrated under vacuum. The crude product obtained was purified by preparative HPLC or by flash chromatography (DCM/MeOH (7N $NH_3$) 99:1 to 95:5) to afford the expected substituted quinazoline.

Method 4:
Secondary amine (10 equiv) was added to the 2-chloroquinazoline (1 equiv) in toluene and the mixture was heated overnight at 130° C. The reaction mixture was concentrated under reduced pressure and the residue was purified by flash chromatography (DCM/MeOH (7N NH₃) 99:1 to 95:5) to afford the expected substituted quinazoline.

Method 5:

Secondary amine (10 equiv) was added to the 2-chloroquinazoline (1 equiv) and the reaction mixture was heated at 185° C. in microwave for 30 minutes. The residue was purified by flash chromatography (DCM/MeOH (7N NH₃) 99:1 to 95:5) to afford the expected substituted quinazoline.

LCMS Method

Column: YMC ODS, 50×4.6 mm, 3 μm. Mobile phase: A. 0.05% TFA in water and B. 0.05% TFA in acetonitrile. Injection volume: 5.0 μL. Flow rate: 1.2 mL/min. Gradient program: 20% B to 100% B in 3.0 minutes.

HPLC Method

Column: YMC ODS, 150×4.6 mm, 5 μm. Mobile phase: A. 0.05% TFA in water and B. 0.05% TFA in acetonitrile. Injection volume: 10 μL. Flow rate: 1.4 mL/min. Gradient program: 5% B to 95% B in 8.0 minutes.

TABLE 1

Preparation of intermediate compounds.

| Intermediate | Starting material | Method | Calculated Mass | Found Mass |
|---|---|---|---|---|
| | | 1 | 413.1744 | 413.1745 |
| | | 1 | 455.2214 | 455.2224 |
| | | 1 | 397.1429 | 397.1431 |
| | | 1 | 489.2057 | 489.2047 |

TABLE 1-continued

Preparation of intermediate compounds.

| Intermediate | Starting material | Method | Calculated Mass | Found Mass |
|---|---|---|---|---|
| (dibenzyloxy quinazoline with benzylpiperidinyl-NH substituent) | (dibenzyloxy-2,4-dichloroquinazoline) | 1 | 565.2358 | 565.2370 |
| (methylenedioxy quinazoline with benzylpiperidinyl-NH substituent) | (methylenedioxy-2,4-dichloroquinazoline) | 1 | 397.1429 | 397.1431 |

4-((1-benzylpiperidin-4-yl)oxy)-2-chloro-6,7-dimethoxyquinazoline

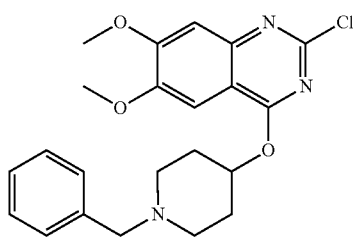 [SMILES: COc1cc2nc(Cl)nc(OC3CCN(Cc4ccccc4)CC3)c2cc1OC]

To a mixture of 2,4-dichloro-6,7-dimethoxyquinazoline (515 mg, 2.0 mmol, provided by Sigma-Aldrich) and 1-benzylpiperidin-4-ol (430 mg, 2.25 mmol, provided by Sigma-Aldrich) in dry DMSO (7.5 mL) was added slowly at room temperature KOt-Bu (335 mg, 3.0 mmol). The reaction mixture was stirred at room temperature for 2 hours. Water (20 mL) was added and the aqueous layer was extracted with DCM (3×30 mL). The combined organic extracts were washed with brine (30 mL), dried over anhydrous MgSO$_4$ and then concentrated under reduced pressure. The crude product was purified by flash chromatography (EtOAc/Pet. Ether 1:1) to furnish 4-((1-benzylpiperidin-4-yl)oxy)-2-chloro-6,7-dimethoxyquinazoline (550 mg, 67%) as a pale yellow solid.

$^1$H NMR (400 MHz, CDCl$_3$, δ): 7.36-7.29 (m, 4H), 7.28-7.22 (m, 2H), 7.17 (s, 1H), 5.41 (tt, J$_1$=8.2 Hz, J$_2$=4.0 Hz, 1H), 3.99 (s, 3H), 3.98 (s, 3H), 3.57 (s, 2H), 2.85-2.75 (m, 2H), 2.40 (br t, J=9.1 Hz, 2H), 2.18-2.09 (m, 2H), 2.00-1.90 (m, 2H). $^{13}$C NMR (100 MHz, CDCl$_3$, δ): 166.0, 156.1, 154.5, 149.8, 138.3, 129.2 (2C), 128.3 (2C), 127.2, 109.4, 106.3, 101.5, 73.6, 63.0, 56.4, 56.3, 50.8 (2C), 30.9 (2C).

N-(1-benzylpiperidin-4-yl)-2-chloro-6,7-dimethoxy-N-methylquinazolin-4-amine

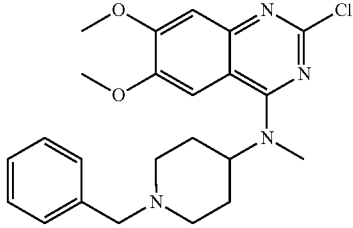 [SMILES: COc1cc2nc(Cl)nc(N(C)C3CCN(Cc4ccccc4)CC3)c2cc1OC]

To a solution of 1-benzylpiperidin-4-amine (1 mL, 933 mg, 4.9 mmol) in dry DCM (20 mL) were added Et$_3$N (1 mL, 725 mg, 7.2 mmol) and di-tert-butyl dicarbonate (1.23 g, 5.6 mmol). The reaction mixture was stirred overnight at room temperature and then diluted with DCM (20 mL). The organic layer was washed with aqueous NaHCO$_3$ solution (10 mL) and brine (10 mL), dried over anhydrous MgSO$_4$ and concentrated in vacuo to give tert-butyl (1-benzylpiperidin-4-yl)carbamate (1.42 g, quant.) as a white solid.

To a suspension of LiAlH$_4$ (1.0 g, 26.35 mmol) in dry THF (10 mL), was added dropwise at 0° C. a solution of tert-butyl (1-benzylpiperidin-4-yl)carbamate (1.4 g, 4.82 mmol) in dry THF (10 mL). The reaction mixture was refluxed for 72 hours, cooled to 0° C. and diluted with THF (50 mL). EtOAc was added to quench the excess of LiAlH$_4$ and 3N aqueous NaOH solution was added to form a white precipitate. The mixture was filtrated over a celite cake and the filtrate was concentrated under reduced pressure to furnish 1-benzyl-N-methylpiperidin-4-amine (980 mg, quant.) as a pale yellow oil.

To a mixture of 2,4-dichloro-6,7-dimethoxyquinazoline (650 mg, 2.51 mmol) and 1-benzyl-N-methylpiperidin-4-amine (680 mg, 3.34 mmol) in dry THF (16 mL) was added Et$_3$N (1.4 mL, 1.02 g, 10.0 mmol). The reaction mixture was stirred overnight at room temperature and then concentrated under reduced pressure. The residue was purified by flash chromatography (DCM/MeOH 100:0 to 98:2) to furnish N-(1-benzylpiperidin-4-yl)-2-chloro-6,7-dimethoxy-N-methylquinazolin-4-amine (500 mg, 47%) as a white solid.

$^1$H NMR (400 MHz, CDCl$_3$, δ): 7.35-7.30 (m, 4H), 7.28-7.24 (m, 1H), 7.14 (s, 1H), 7.12 (s, 1H), 4.29 (tt, $J_1$=10.8 Hz, $J_2$=3.7 Hz, 1H), 3.98 (s, 3H), 3.93 (s, 3H), 3.53 (s, 2H), 3.17 (s, 3H), 3.03 (d, J=10.8 Hz), 2.15-1.97 (m, 4H), 1.90-1.83 (m, 2H). $^{13}$C NMR (100 MHz, CDCl$_3$, δ): 164.5, 155.2, 154.7, 151.0, 147.6, 138.3, 129.2 (2C), 128.4 (2C), 127.3, 108.9, 107.2, 104.3, 63.1, 58.7, 56.3, 56.1, 53.1 (2C), 33.9, 29.4 (2C).

2-chloro-6,7-dimethoxy-4-(piperidin-4-ylthio)quinazoline trihydrochloride

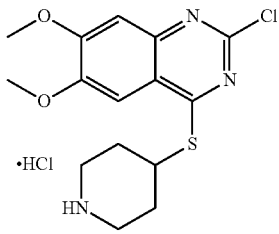 [SMILES: COc1cc2nc(Cl)nc(SC3CCNCC3)c2cc1OC ; Cl]

To a suspension of sodium hydride (60% in mineral oil, 70 mg, 1.75 mmol) in dry THF (4 mL) was added dropwise at 0° C. a solution of tert-butyl 4-mercaptopiperidine-1-carboxylate (350 mg, 1.61 mmol, prepared following the procedure described in PCT Int. Appl., 2008077552) in dry THF (4 mL). Reaction mixture was stirred at 0° C. for 20 minutes and a solution of 2,4-dichloro-6,7-dimethoxyquinazoline (415 mg, 1.60 mmol) in dry THF (4 mL) was added dropwise. The mixture was stirred for 1 hour at 0° C. and then overnight at room temperature. An aqueous ammonium chloride solution (20 mL) was added and the aqueous phase was extracted with diethyl ether (2×50 mL). The combined organic extracts were washed with brine (40 mL), dried over anhydrous MgSO$_4$ and concentrated under reduced pressure. The crude product was purified by flash chromatography (Pet. Ether/Et$_2$O 2:1 to 1:1) to furnish tert-butyl 4-((2-chloro-6,7-dimethoxyquinazolin-4-yl)thio)piperidine-1-carboxylate (560 mg, 80%) as a colourless solid.

Tert-butyl 4-((2-chloro-6,7-dimethoxyquinazolin-4-yl)thio)piperidine-1-carboxylate (170 mg, 0.39 mmol) was solubilised in 4N HCl solution in dioxane (5 mL, 20 mmol). The reaction mixture was stirred overnight at room temperature and then concentrated under reduced pressure to give 2-chloro-6,7-dimethoxy-4-(piperidin-4-ylthio)quinazoline trihydrochloride (98%) as a light brown solid.

$^1$H NMR (400 MHz, d$_6$-DMSO, δ): 9.38 (br s, 1H), 9.17 (broad s, 1H), 7.67 (broad s, 2H), 7.31 (s, 1H), 7.16 (s, 1H), 4.26 (td, $J_1$=10.4 Hz, $J_2$=5.1 Hz, 1H), 3.96 (s, 3H), 3.94 (s, 3H), 3.30 (br d, J=12.8 Hz, 2H), 3.13 (br q, J=12.8 Hz, 2H), 2.30 (dd, $J_1$=12.8 Hz, $J_2$=3.2 Hz, 2H), 2.00 (qd, $J_j$=12.8 Hz, $J_2$=3.2 Hz, 2H). $^{13}$C NMR (125 MHz, d$_6$-DMSO, δ): 168.7, 156.7, 153.3, 150.3, 147.1, 116.5, 106.5, 101.2, 56.5, 56.1, 42.5 (2C), 38.1, 28.0 (2C). HRMS (+ESI-ToF) m/z: [M+H]$^+$ calcd for C$_{15}$H$_{18}$ClN$_3$O$_2$S: 340.0887, found, 340.0882.

4-((1-benzylpiperidin-4-yl)thio)-2-chloro-6,7-dimethoxyquinazoline

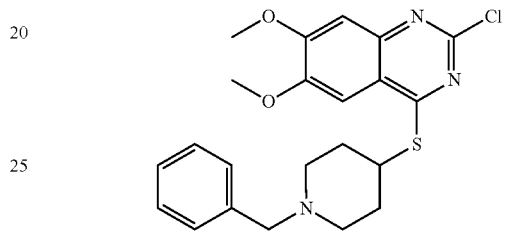

To a solution of 2-chloro-6,7-dimethoxy-4-(piperidin-4-ylthio)quinazoline trihydrochloride (170 mg, 0.38 mmol) in an ethanol/methylene chloride mixture (10/5 mL) were added triethylamine (0.16 mL, 1.19 mmol), acetic acid (0.07 mL, 1.22 mmol) and then benzaldehyde (0.06 mL, 0.59 mmol). The reaction mixture was stirred for 5 minutes and sodium triacetoxyborohydride (130 mg, 0.60 mmol) was added. The reaction mixture was stirred overnight at room temperature and then concentrated under reduced pressure. The crude residue was purified by flash chromatography (DCM/MeOH 100:0 to 98:2) to give 4-((1-benzylpiperidin-4-yl)thio)-2-chloro-6,7-dimethoxyquinazoline (110 mg, 67%) as a yellow oil.

$^1$H NMR (400 MHz, CD$_3$OD, δ): 7.39-7.24 (m, 5H), 7.17 (s, 1H), 7.12 (s, 1H), 4.14 (m, 1H), 4.00 (s, 3H), 3.97 (s, 3H), 3.59 (s, 2H), 2.91 (br d, J=11.5 Hz, 2H), 2.37 (br t, J=11.5 Hz, 2H), 2.22 (dd, $J_1$=11.5 Hz, $J_2$=3.6 Hz, 2H), 1.85 (qd, $J_1$=11.5 Hz, $J_2$=3.6 Hz, 2H). $^{13}$C NMR (125 MHz, CD$_3$OD, δ): 171.8, 158.5, 155.4, 152.0, 148.4, 138.4, 130.8 (2C), 129.4 (2C), 128.5, 118.3, 106.8, 102.6, 64.1, 56.9, 56.7, 54.0 (2C), 42.1, 32.7 (2C). FIRMS (+ESI-ToF) m/z: [M+H]$^+$ calcd for C$_{22}$H$_{24}$ClN$_3$O$_2$S: 430.1356, found, 430.1345.

TABLE 2

Preparation of HKMTi compounds.

| Name | Structure | Intermediate | Method | Calculated Mass | Found Mass |
|---|---|---|---|---|---|
| HKMTi-1-005 | 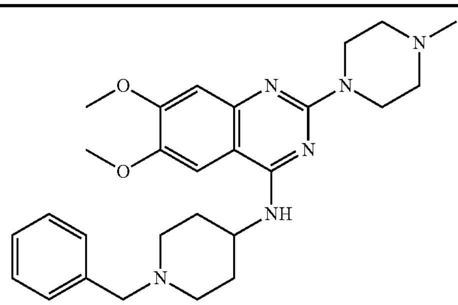 | | 5 | 477.2978 | 477.2970 |

TABLE 2-continued

Preparation of HKMTi compounds.

| Name | Structure | Intermediate | Method | Calculated Mass | Found Mass |
|---|---|---|---|---|---|
| HKMTi-1-022 | 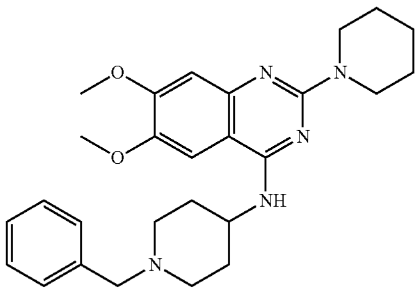 [SMILES: COc1cc2nc(N3CCCCC3)nc(NC3CCN(Cc4ccccc4)CC3)c2cc1OC] | | 5 | 462.2868 | 462.2855 |
| HKMTi-1-011 | 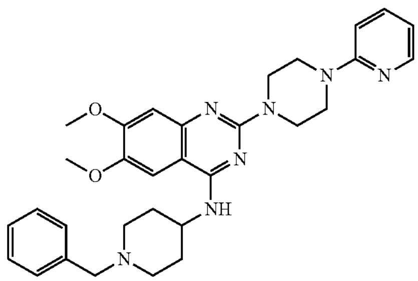 [SMILES: COc1cc2nc(N3CCN(c4ccccn4)CC3)nc(NC3CCN(Cc4ccccc4)CC3)c2cc1OC] | | 5 | 540.3087 | 540.3077 |
| HKMTi-1-169 | 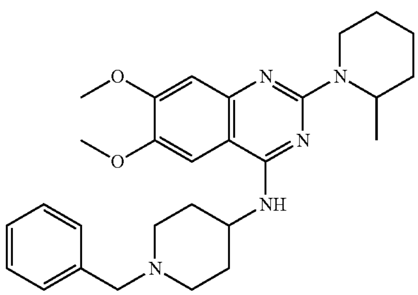 [SMILES: COc1cc2nc(N3CCCCC3C)nc(NC3CCN(Cc4ccccc4)CC3)c2cc1OC] | | 5 | 476 | 476 |
| HKMTi-1-064 | 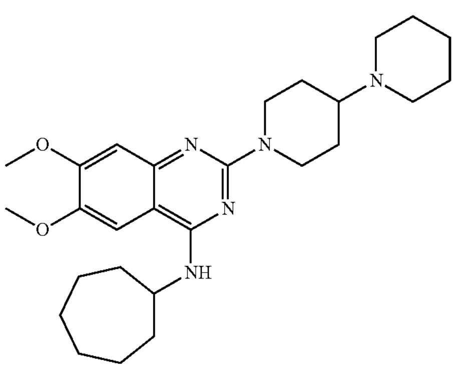 [SMILES: COc1cc2nc(N3CCC(N4CCCCC4)CC3)nc(NC3CCCCCC3)c2cc1OC] | | 4 | 468.3339 | 468.3325 |
| HKMTi-1-065 | 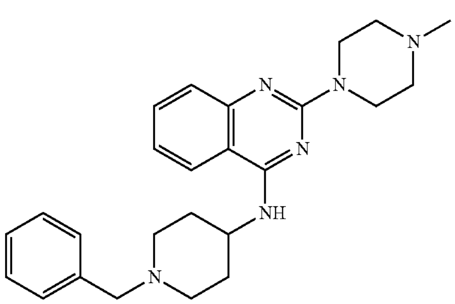 [SMILES: CN1CCN(c2nc(NC3CCN(Cc4ccccc4)CC3)c3ccccc3n2)CC1] | | 5 | 417.2767 | 417.2756 |

TABLE 2-continued

Preparation of HKMTi compounds.

| Name | Structure | Intermediate | Method | Calculated Mass | Found Mass |
|---|---|---|---|---|---|
| HKMTi-1-066 | 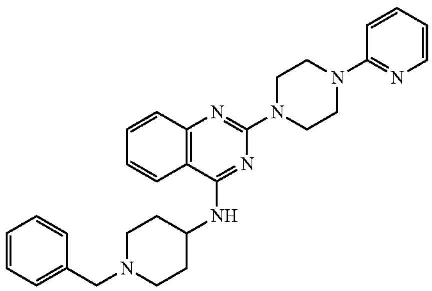 [SMILES: c1ccc(CN2CCC(Nc3nc(N4CCN(c5ccccn5)CC4)nc4ccccc34)CC2)cc1] | | 5 | 480.4 | 480.4 |
| HKMTi-1-067 | 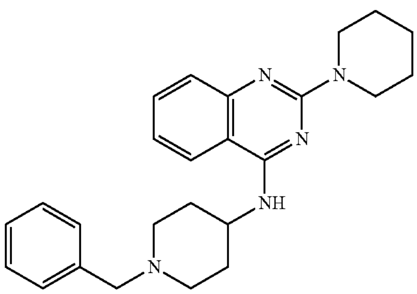 [SMILES: c1ccc(CN2CCC(Nc3nc(N4CCCCC4)nc4ccccc34)CC2)cc1] | | 5 | 402.3 | 402.3 |
| HKMTi-1-068 | 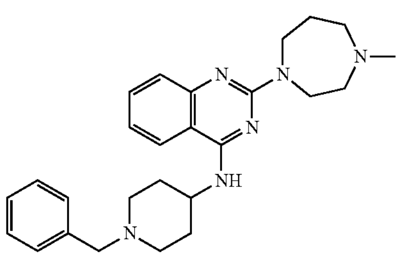 [SMILES: CN1CCCN(c2nc(NC3CCN(Cc4ccccc4)CC3)c3ccccc3n2)CC1] | | 5 | 431.2923 | 431.2903 |
| HKMTi-1-069 | 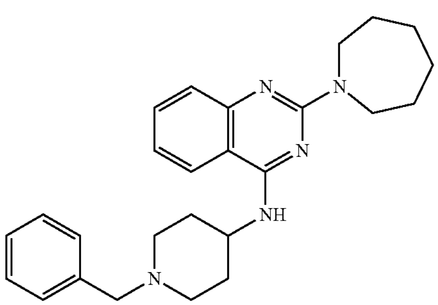 [SMILES: c1ccc(CN2CCC(Nc3nc(N4CCCCCC4)nc4ccccc34)CC2)cc1] | | 5 | 416.2814 | 416.2814 |
| HKMTi-1-070 | 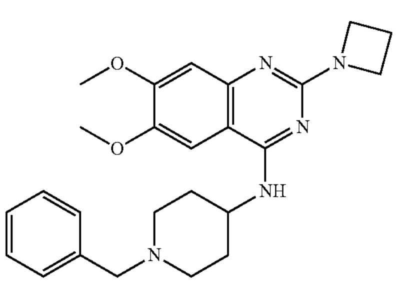 [SMILES: COc1cc2nc(N3CCC3)nc(NC3CCN(Cc4ccccc4)CC3)c2cc1OC] | | 4 | 434.2535 | 434.2556 |

TABLE 2-continued

Preparation of HKMTi compounds.

| Name | Structure | Intermediate | Method | Calculated Mass | Found Mass |
|---|---|---|---|---|---|
| HKMTi-1-071 | 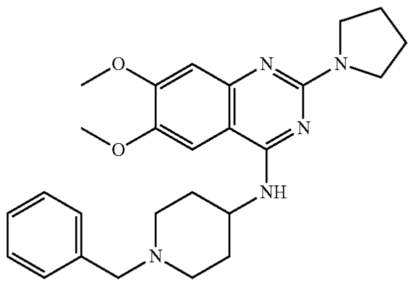 [SMILES: COc1cc2nc(N3CCCC3)nc(NC3CCN(Cc4ccccc4)CC3)c2cc1OC] | | 4 | 448.3 | 448.3 |
| HKMTi-1-072 | 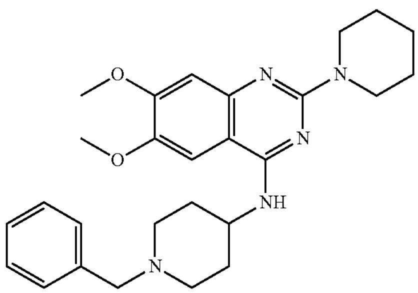 [SMILES: COc1cc2nc(N3CCCCC3)nc(NC3CCN(Cc4ccccc4)CC3)c2cc1OC] | | 4 | 463.2709 | 463.2703 |
| HKMTi-1-073 | 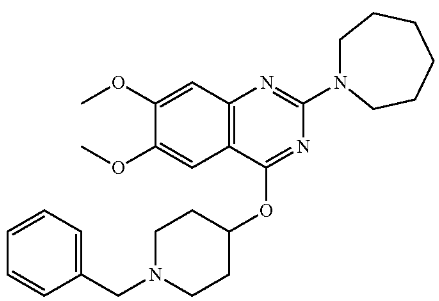 [SMILES: COc1cc2nc(N3CCCCCC3)nc(OC3CCN(Cc4ccccc4)CC3)c2cc1OC] | | 4 | 477.2866 | 477.2858 |
| HKMTi-1-074 | 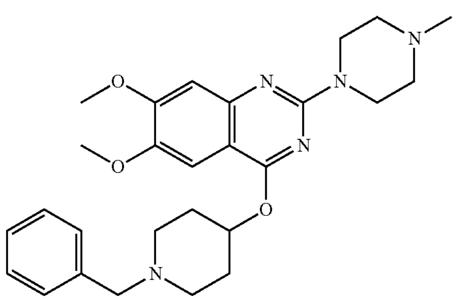 [SMILES: COc1cc2nc(N3CCN(C)CC3)nc(OC3CCN(Cc4ccccc4)CC3)c2cc1OC] | | 4 | 478.2818 | 478.2795 |
| HKMTi-1-075 | 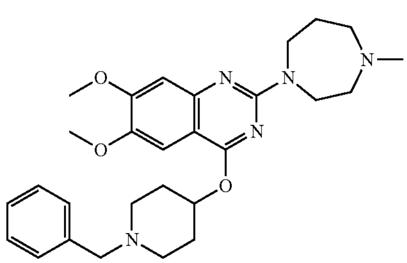 [SMILES: COc1cc2nc(N3CCCN(C)CC3)nc(OC3CCN(Cc4ccccc4)CC3)c2cc1OC] | | 4 | 492.2975 | 492.2965 |

TABLE 2-continued

Preparation of HKMTi compounds.

| Name | Structure | Intermediate | Method | Calculated Mass | Found Mass |
|---|---|---|---|---|---|
| HKMTi-1-076 | 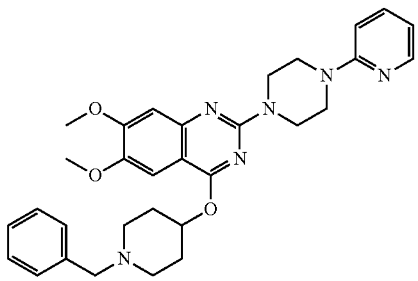 [SMILES: COc1cc2nc(N3CCN(c4ccccn4)CC3)nc(OC3CCN(Cc4ccccc4)CC3)c2cc1OC] | | 4 | 541.2927 | 541.2936 |
| HKMTi-1-077 | 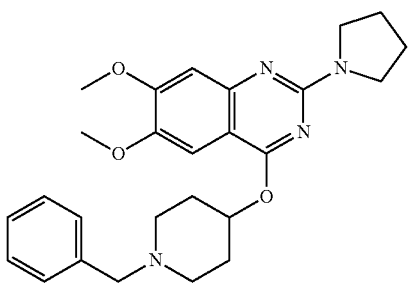 [SMILES: COc1cc2nc(N3CCCC3)nc(OC3CCN(Cc4ccccc4)CC3)c2cc1OC] | | 4 | 449.2553 | 449.2548 |
| HKMTi-1-078 | 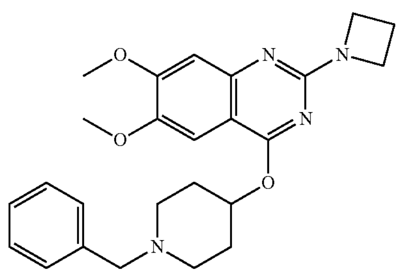 | | 4 | 435.2396 | 435.2377 |
| HKMTi-1-079 | 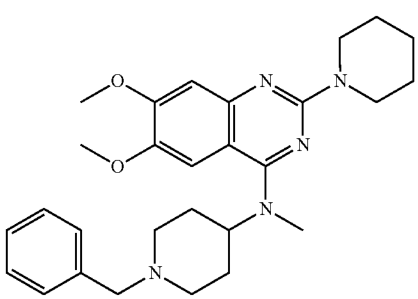 [SMILES: COc1cc2nc(N3CCCCC3)nc(N(C)C3CCN(Cc4ccccc4)CC3)c2cc1OC] | | 4 | 476.3026 | 476.3028 |
| HKMTi-1-080 | 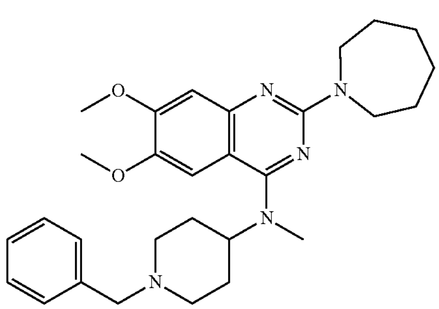 [SMILES: COc1cc2nc(N3CCCCCC3)nc(N(C)C3CCN(Cc4ccccc4)CC3)c2cc1OC] | | 4 | 490.3182 | 490.3167 |

TABLE 2-continued

Preparation of HKMTi compounds.

| Name | Structure | Intermediate | Method | Calculated Mass | Found Mass |
|---|---|---|---|---|---|
| HKMTi-1-081 | 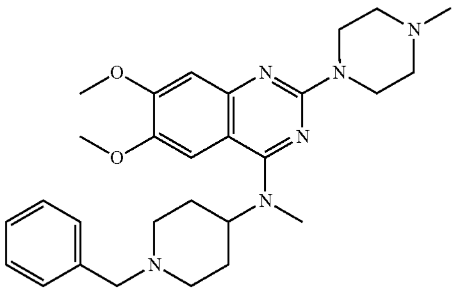 [SMILES: COc1cc2nc(N3CCN(C)CC3)nc(N(C)C3CCN(Cc4ccccc4)CC3)c2cc1OC] | | 4 | 491.3134 | 491.3127 |
| HKMTi-1-082 | 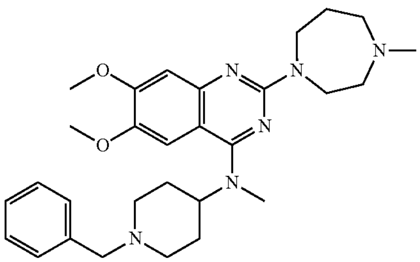 [SMILES: COc1cc2nc(N3CCCN(C)CC3)nc(N(C)C3CCN(Cc4ccccc4)CC3)c2cc1OC] | | 4 | 505.3291 | 505.3277 |
| HKMTi-1-083 | 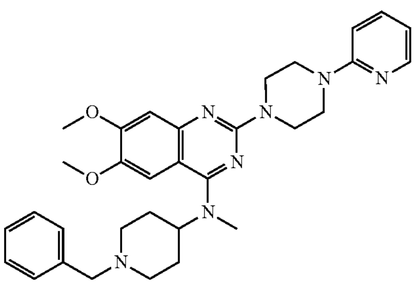 [SMILES: COc1cc2nc(N3CCN(c4ccccn4)CC3)nc(N(C)C3CCN(Cc4ccccc4)CC3)c2cc1OC] | | 4 | 554.3243 | 554.3237 |
| HKMTi-1-084 | 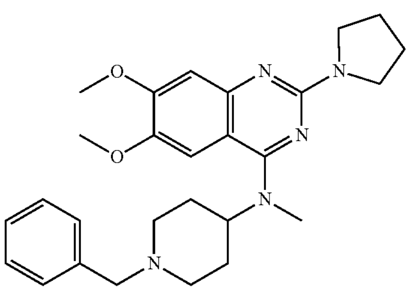 [SMILES: COc1cc2nc(N3CCCC3)nc(N(C)C3CCN(Cc4ccccc4)CC3)c2cc1OC] | | 4 | 462.2869 | 462.2860 |
| HKMTi-1-085 | 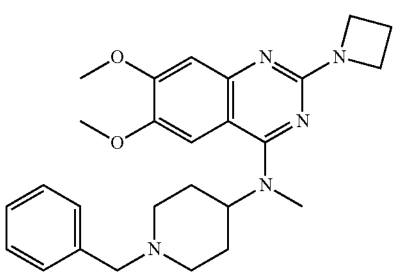 [SMILES: COc1cc2nc(N3CCC3)nc(N(C)C3CCN(Cc4ccccc4)CC3)c2cc1OC] | | 4 | 448.2713 | 448.2721 |

TABLE 2-continued

Preparation of HKMTi compounds.

| Name | Structure | Intermediate | Method | Calculated Mass | Found Mass |
|---|---|---|---|---|---|
| HKMTi-1-086 | 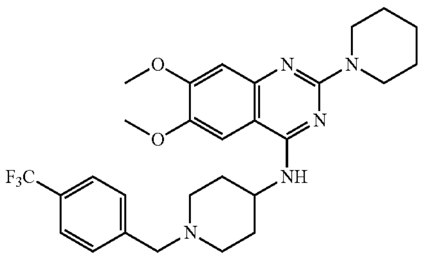 [SMILES: COc1cc2nc(N3CCCCC3)nc(NC3CCN(Cc4ccc(C(F)(F)F)cc4)CC3)c2cc1OC] | | 4 | 530.2743 | 530.2723 |
| HKMTi-1-087 | 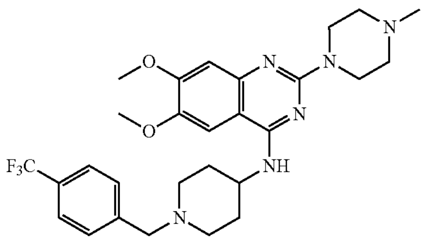 [SMILES: COc1cc2nc(N3CCN(C)CC3)nc(NC3CCN(Cc4ccc(C(F)(F)F)cc4)CC3)c2cc1OC] | | 4 | 545.2852 | 545.2822 |
| HKMTi-1-088 | 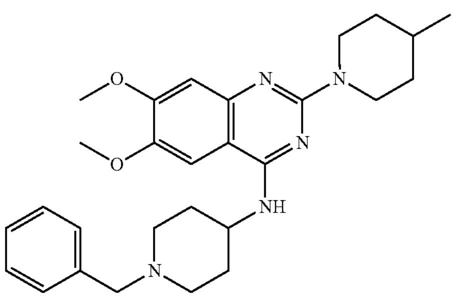 [SMILES: COc1cc2nc(N3CCC(C)CC3)nc(NC3CCN(Cc4ccccc4)CC3)c2cc1OC] | | 2 | 557.3 | 557.3 |
| HKMTi-1-089 | 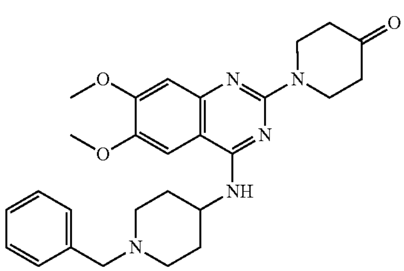 [SMILES: COc1cc2nc(N3CCC(=O)CC3)nc(NC3CCN(Cc4ccccc4)CC3)c2cc1OC] | | 3 | 486.4 | 476.4 |
| HKMTi-1-090 | 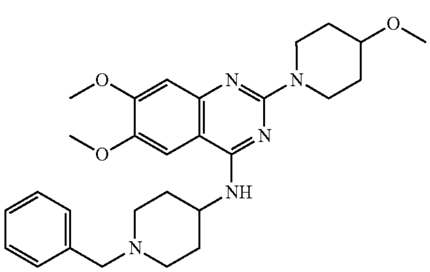 [SMILES: COc1cc2nc(N3CCC(OC)CC3)nc(NC3CCN(Cc4ccccc4)CC3)c2cc1OC] | | 3 | 492.2 | 492.2 |

TABLE 2-continued

Preparation of HKMTi compounds.

| Name | Structure | Intermediate | Method | Calculated Mass | Found Mass |
|---|---|---|---|---|---|
| HKMTi-1-091 | 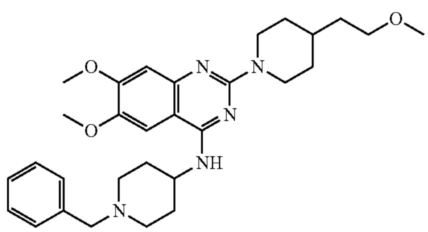 [SMILES: COCCC1CCN(c2nc(NC3CCN(Cc4ccccc4)CC3)c3cc(OC)c(OC)cc3n2)CC1] | | 3 | 520.1 | 520.1 |
| HKMTi-1-092 | 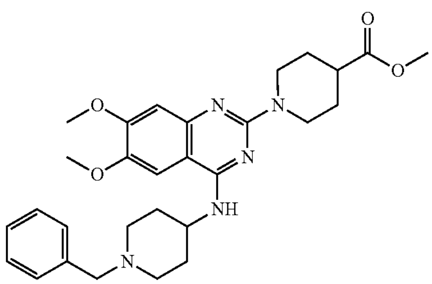 [SMILES: COC(=O)C1CCN(c2nc(NC3CCN(Cc4ccccc4)CC3)c3cc(OC)c(OC)cc3n2)CC1] | | 3 | 520.4 | 520.4 |
| HKMTi-1-093 | 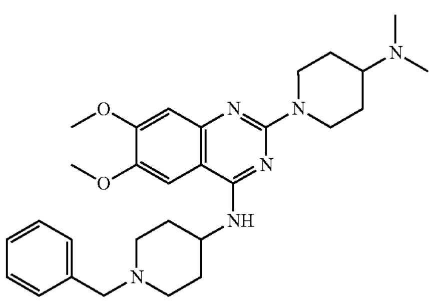 [SMILES: COc1cc2nc(N3CCC(N(C)C)CC3)nc(NC3CCN(Cc4ccccc4)CC3)c2cc1OC] | | 3 | 505.3291 | 505.3286 |
| HKMTi-1-094 | 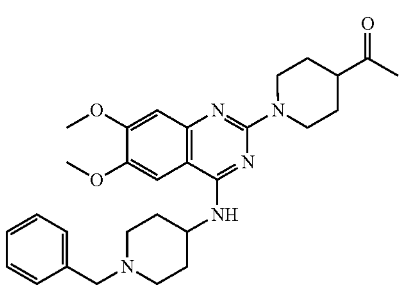 [SMILES: COc1cc2nc(N3CCC(C(C)=O)CC3)nc(NC3CCN(Cc4ccccc4)CC3)c2cc1OC] | | 3 | 505.1 | 505.1 |
| HKMTi-1-095 | 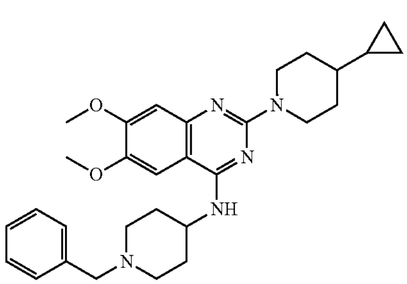 [SMILES: COc1cc2nc(N3CCC(C4CC4)CC3)nc(NC3CCN(Cc4ccccc4)CC3)c2cc1OC] | | 3 | 503.5 | 503.5 |

TABLE 2-continued

Preparation of HKMTi compounds.

| Name | Structure | Intermediate | Method | Calculated Mass | Found Mass |
|---|---|---|---|---|---|
| HKMTi-1-096 | 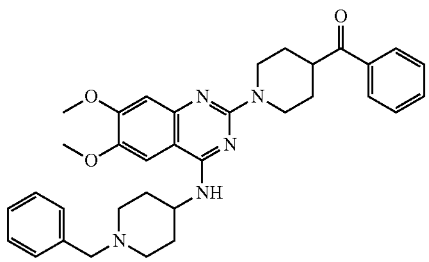 [SMILES: COc1cc2nc(N3CCC(C(=O)c4ccccc4)CC3)nc(NC3CCN(Cc4ccccc4)CC3)c2cc1OC] | | 3 | 567.4 | 567.4 |
| HKMTi-1-097 | 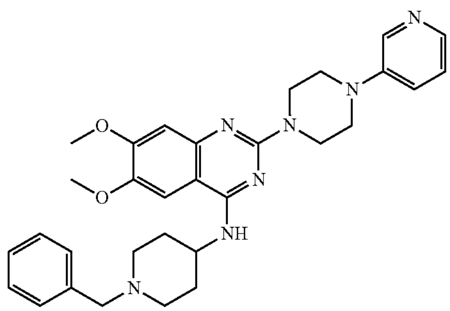 [SMILES: COc1cc2nc(N3CCN(c4cccnc4)CC3)nc(NC3CCN(Cc4ccccc4)CC3)c2cc1OC] | | 3 | 540.5 | 540.5 |
| HKMTi-1-098 | 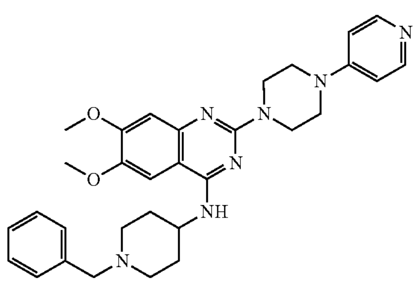 [SMILES: COc1cc2nc(N3CCN(c4ccncc4)CC3)nc(NC3CCN(Cc4ccccc4)CC3)c2cc1OC] | | 3 | 540.5 | 540.5 |
| HKMTi-1-099 | 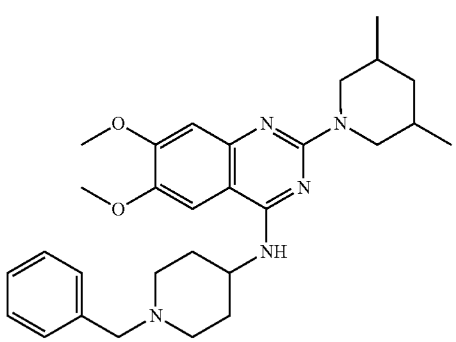 [SMILES: COc1cc2nc(N3CC(C)CC(C)C3)nc(NC3CCN(Cc4ccccc4)CC3)c2cc1OC] | | 3 | 490.3 | 490.3 |
| HKMTi-1-100 | 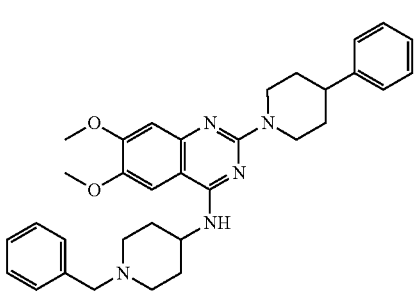 [SMILES: COc1cc2nc(N3CCC(c4ccccc4)CC3)nc(NC3CCN(Cc4ccccc4)CC3)c2cc1OC] | | 3 | 538.5 | 538.5 |

TABLE 2-continued

Preparation of HKMTi compounds.

| Name | Structure | Intermediate | Method | Calculated Mass | Found Mass |
|---|---|---|---|---|---|
| HKMTi-1-101 | 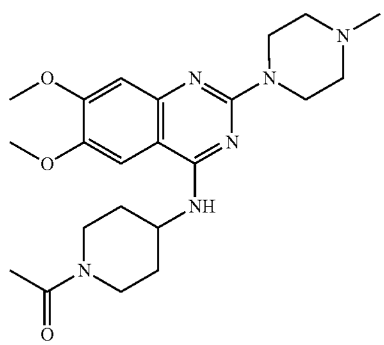 | | 3 | 429.3 | 429.3 |
| HKMTi-1-102 | 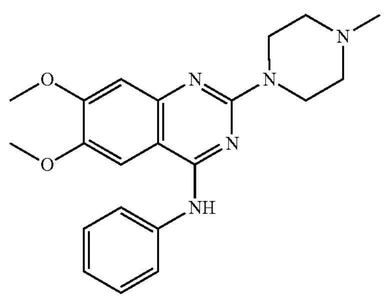 | | 3 | 380.3 | 380.3 |
| HKMTi-1-103 | 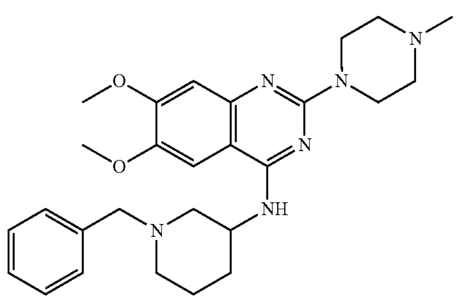 [SMILES: COc1cc2nc(N3CCN(C)CC3)nc(NC3CCCN(Cc4ccccc4)C3)c2cc1OC] | | 3 | 477.4 | 477.4 |
| HKMTi-1-104 | 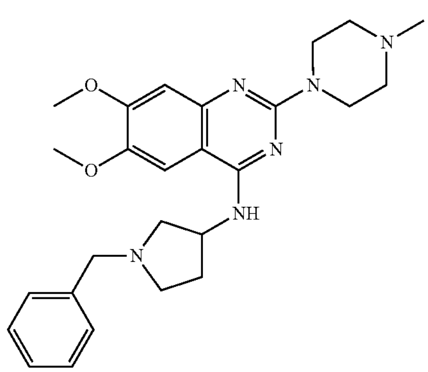 [SMILES: COc1cc2nc(N3CCN(C)CC3)nc(NC3CCN(Cc4ccccc4)C3)c2cc1OC] | | 2 | 463.2821 | 463.2825 |

TABLE 2-continued

Preparation of HKMTi compounds.

| Name | Structure | Intermediate | Method | Calculated Mass | Found Mass |
|---|---|---|---|---|---|
| HKMTi-1-105 | 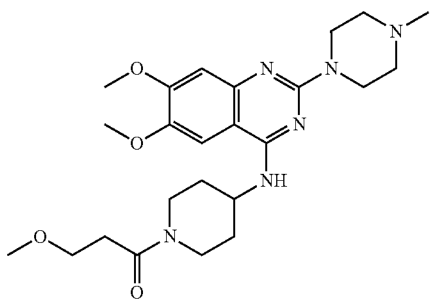 | | 3 | 473.3 | 473.3 |
| HKMTi-1-106 | 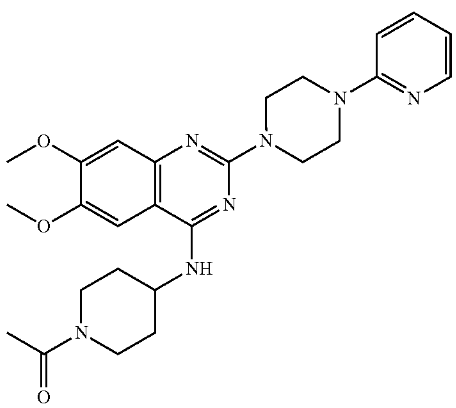 [SMILES: COc1cc2nc(N3CCN(c4ccccn4)CC3)nc(NC3CCN(C(C)=O)CC3)c2cc1OC] | | 2 | 492.0 | 492.0 |
| HKMTi-1-107 | 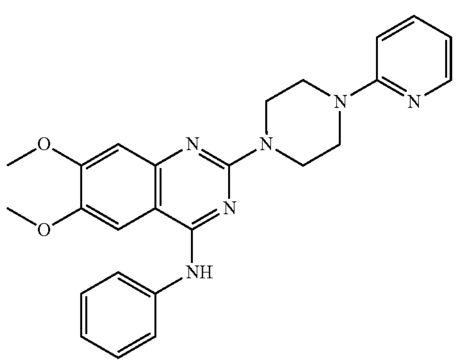 [SMILES: COc1cc2nc(N3CCN(c4ccccn4)CC3)nc(Nc3ccccc3)c2cc1OC] | | 3 | 443.1 | 443.1 |
| HKMTi-1-108 | 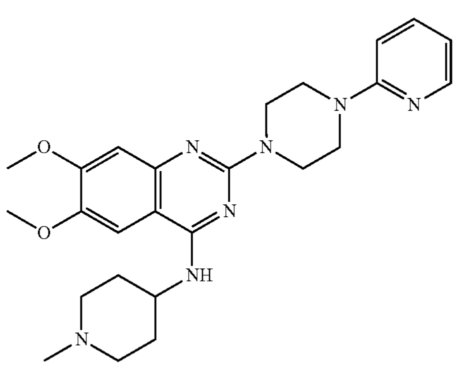 [SMILES: COc1cc2nc(N3CCN(c4ccccn4)CC3)nc(NC3CCN(C)CC3)c2cc1OC] | | 3 | 464.2774 | 464.2774 |

TABLE 2-continued

Preparation of HKMTi compounds.

| Name | Structure | Intermediate | Method | Calculated Mass | Found Mass |
|---|---|---|---|---|---|
| HKMTi-1-109 | 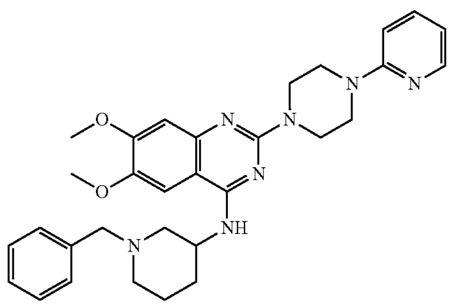 [SMILES: COc1cc2nc(N3CCN(c4ccccn4)CC3)nc(NC3CCCN(Cc4ccccc4)C3)c2cc1OC] | | 3 | 540.2 | 540.2 |
| HKMTi-1-110 | 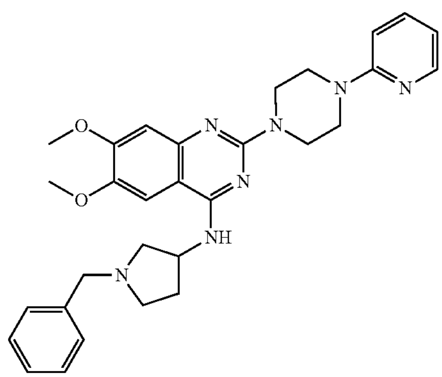 [SMILES: COc1cc2nc(N3CCN(c4ccccn4)CC3)nc(NC3CCN(Cc4ccccc4)C3)c2cc1OC] | | 2 | 526.2 | 526.2 |
| HKMTi-1-111 | 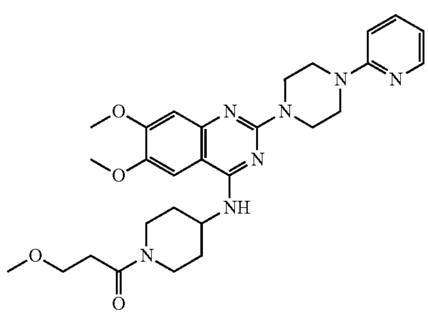 [SMILES: COCCC(=O)N1CCC(Nc2nc(N3CCN(c4ccccn4)CC3)nc3cc(OC)c(OC)cc23)CC1] | | 3 | 537.2 | 537.2 |
| HKMTi-1-112 | 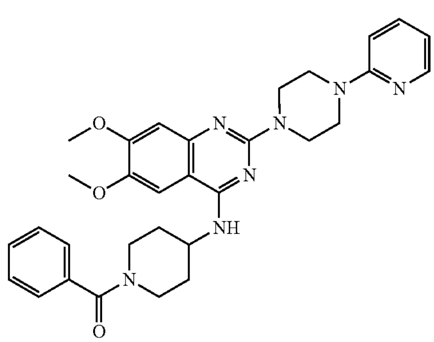 [SMILES: COc1cc2nc(N3CCN(c4ccccn4)CC3)nc(NC3CCN(C(=O)c4ccccc4)CC3)c2cc1OC] | | 3 | 554.1 | 554.1 |

TABLE 2-continued

Preparation of HKMTi compounds.

| Name | Structure | Intermediate | Method | Calculated Mass | Found Mass |
|---|---|---|---|---|---|
| HKMTi-1-113 | 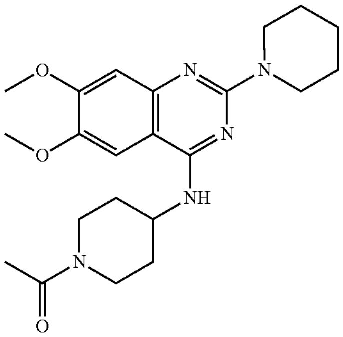 [SMILES: COc1cc2nc(N3CCCCC3)nc(NC3CCN(C(C)=O)CC3)c2cc1OC] | | 3 | 414.1 | 414.1 |
| HKMTi-1-114 | 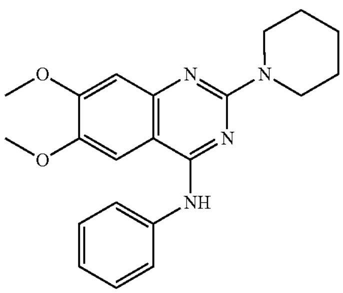 [SMILES: COc1cc2nc(N3CCCCC3)nc(Nc3ccccc3)c2cc1OC] | | 3 | 365.3 | 365.3 |
| HKMTi-1-115 | 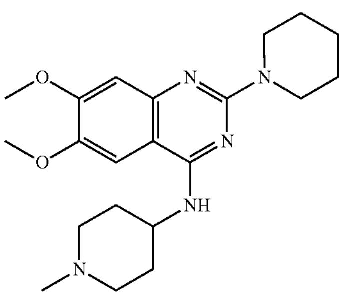 [SMILES: COc1cc2nc(N3CCCCC3)nc(NC3CCN(C)CC3)c2cc1OC] | | 2 | 386.2 | 386.2 |
| HKMTi-1-116 | 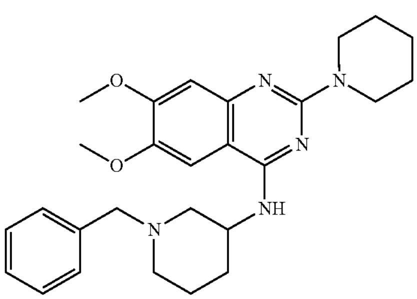 [SMILES: COc1cc2nc(N3CCCCC3)nc(NC3CCCN(Cc4ccccc4)C3)c2cc1OC] | | 3 | 462.2869 | 462.2851 |

TABLE 2-continued

Preparation of HKMTi compounds.

| Name | Structure | Intermediate | Method | Calculated Mass | Found Mass |
|---|---|---|---|---|---|
| HKMTi-1-117 | 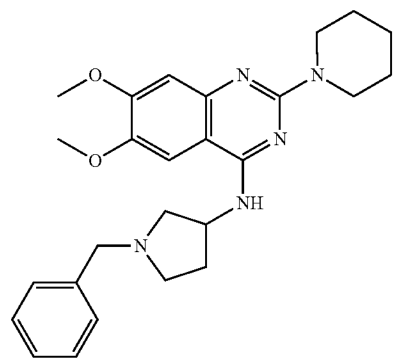 [SMILES: COc1cc2nc(N3CCCCC3)nc(NC3CCN(Cc4ccccc4)C3)c2cc1OC] | | 3 | 448.2713 | 448.2720 |
| HKMTi-1-118 | 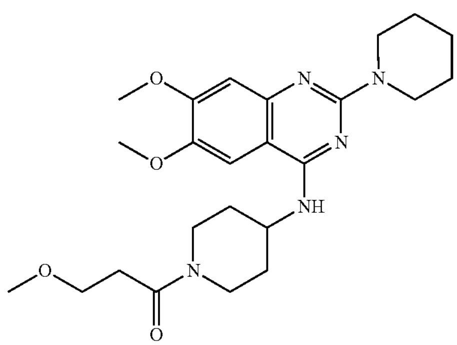 [SMILES: COCCC(=O)N1CCC(Nc2nc(N3CCCCC3)nc3cc(OC)c(OC)cc23)CC1] | | 3 | 458.4 | 458.4 |
| HKMTi-1-119 | 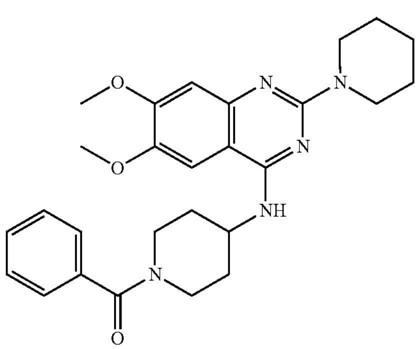 [SMILES: COc1cc2nc(N3CCCCC3)nc(NC3CCN(C(=O)c4ccccc4)CC3)c2cc1OC] | | 3 | 576.1 | 576.1 |
| HKMTi-1-120 | 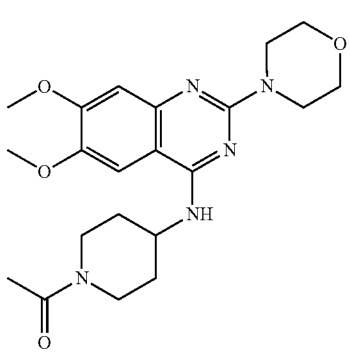 [SMILES: COc1cc2nc(N3CCOCC3)nc(NC3CCN(C(C)=O)CC3)c2cc1OC] | | 3 | 416.1 | 416.1 |

TABLE 2-continued

*Preparation of HKMTi compounds.*

| Name | Structure | Intermediate | Method | Calculated Mass | Found Mass |
|---|---|---|---|---|---|
| HKMTi-1-121 | 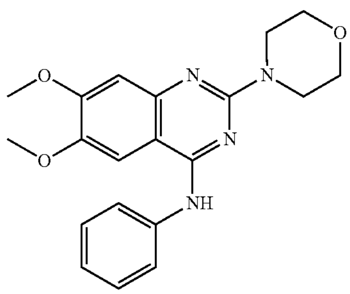 [SMILES: COc1cc2nc(N3CCOCC3)nc(Nc3ccccc3)c2cc1OC] | | 3 | 367.0 | 367.0 |
| HKMTi-1-122 | 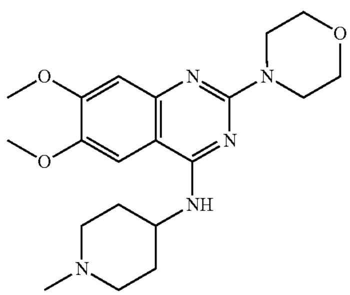 [SMILES: COc1cc2nc(N3CCOCC3)nc(NC3CCN(C)CC3)c2cc1OC] | | 3 | 388.0 | 388.0 |
| HKMTi-1-123 | 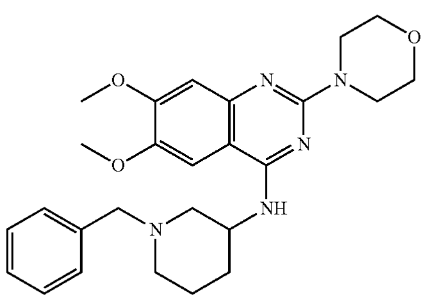 [SMILES: COc1cc2nc(N3CCOCC3)nc(NC3CCCN(Cc4ccccc4)C3)c2cc1OC] | | 3 | 464.2 | 464.2 |
| HKMTi-1-124 | 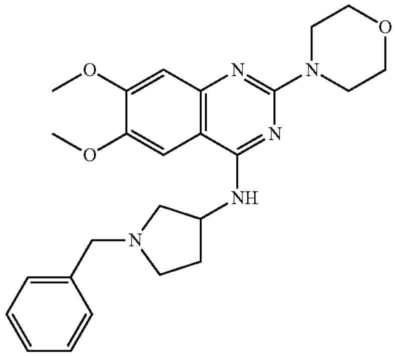 [SMILES: COc1cc2nc(N3CCOCC3)nc(NC3CCN(Cc4ccccc4)C3)c2cc1OC] | | 2 | 540.1 | 540.1 |

TABLE 2-continued

Preparation of HKMTi compounds.

| Name | Structure | Intermediate | Method | Calculated Mass | Found Mass |
|---|---|---|---|---|---|
| HKMTi-1-125 | 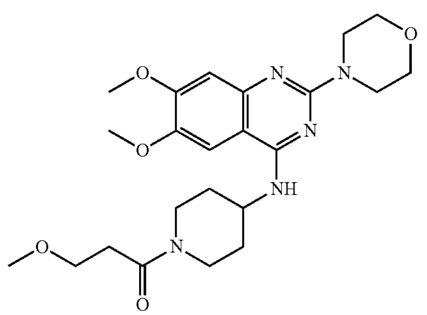 [SMILES: COCCC(=O)N1CCC(Nc2nc(N3CCOCC3)nc3cc(OC)c(OC)cc23)CC1] | | 3 | 460.1 | 460.1 |
| HKMTi-1-126 | 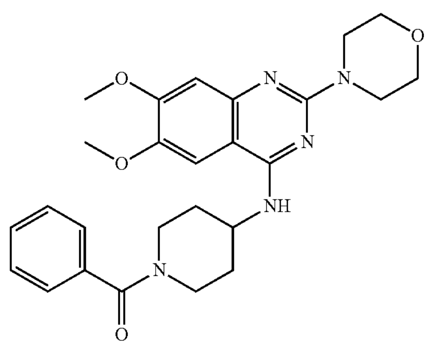 [SMILES: COc1cc2nc(N3CCOCC3)nc(NC3CCN(C(=O)c4ccccc4)CC3)c2cc1OC] | | 3 | 478.3 | 478.3 |
| HKMTi-1-127 | 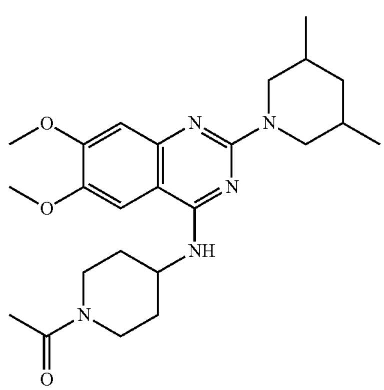 | | 3 | 442.4 | 442.4 |
| HKMTi-1-128 | 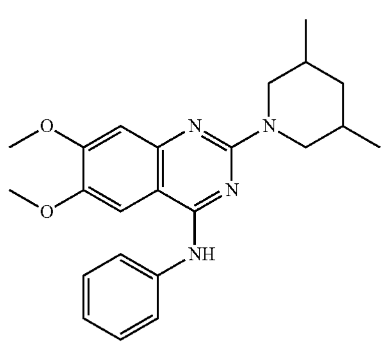 | | 3 | 393.3 | 393.3 |

TABLE 2-continued

Preparation of HKMTi compounds.

| Name | Structure | Intermediate | Method | Calculated Mass | Found Mass |
|------|-----------|--------------|--------|-----------------|------------|
| HKMTi-1-129 | 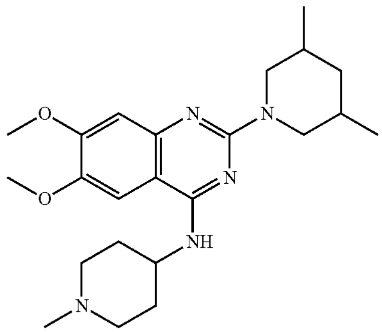 | | 2 | 414.4 | 414.4 |
| HKMTi-1-130 | 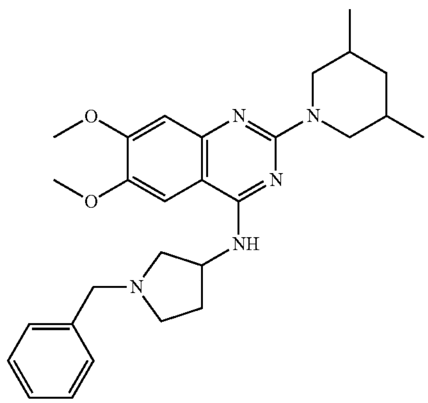 [SMILES: COc1cc2nc(N3CC(C)CC(C)C3)nc(NC3CCN(Cc4ccccc4)C3)c2cc1OC] | | 2 | 476.3026 | 476.3031 |
| HKMTi-1-131 | 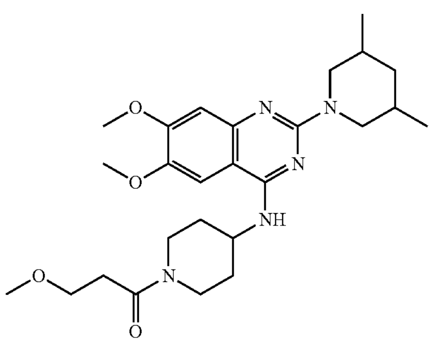 | | 3 | 486.2 | 486.2 |
| HKMTi-1-132 | 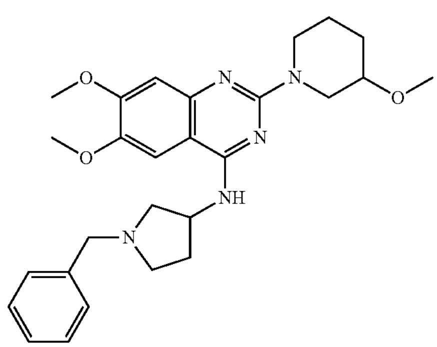 [SMILES: COc1cc2nc(N3CCCC(OC)C3)nc(NC3CCN(Cc4ccccc4)C3)c2cc1OC] | | 2 | 478.1 | 478.1 |

TABLE 2-continued
Preparation of HKMTi compounds.
| Name | Structure | Intermediate | Method | Calculated Mass | Found Mass |
|---|---|---|---|---|---|
| HKMTi-1-133 | 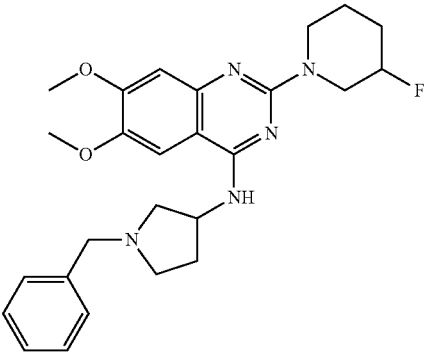 [SMILES: COc1cc2nc(N3CCCC(F)C3)nc(NC3CCN(Cc4ccccc4)C3)c2cc1OC] | 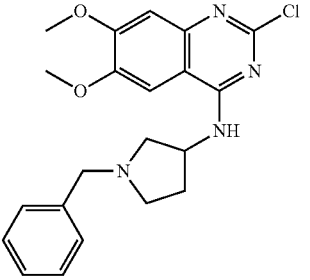 [SMILES: COc1cc2nc(Cl)nc(NC3CCN(Cc4ccccc4)C3)c2cc1OC] | 2 | 466.2 | 466.2 |
| HKMTi-1-134 | 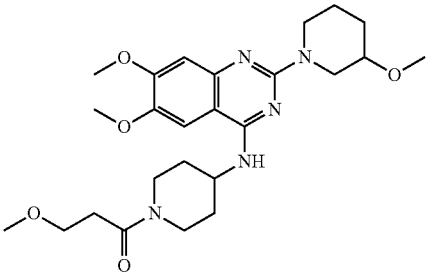 | 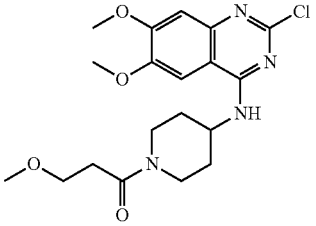 [SMILES: COCCC(=O)N1CCC(Nc2nc(Cl)nc3cc(OC)c(OC)cc23)CC1] | 3 | 488.1 | 488.1 |
| HKMTi-1-135 | 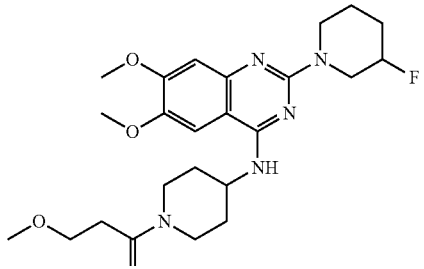 | 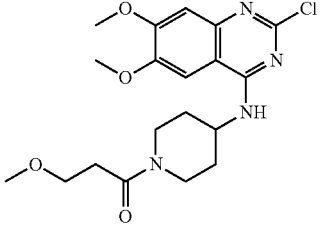 [SMILES: COCCC(=O)N1CCC(Nc2nc(Cl)nc3cc(OC)c(OC)cc23)CC1] | 3 | 476.5 | 476.5 |
| HKMTi-1-136 | 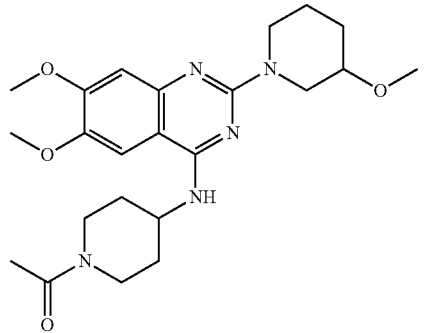 | 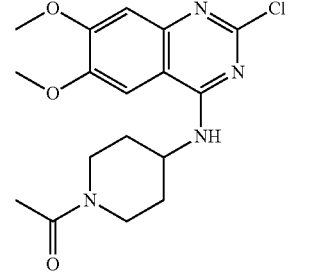 [SMILES: COc1cc2nc(Cl)nc(NC3CCN(C(C)=O)CC3)c2cc1OC] | 3 | 444.4 | 444.4 |

TABLE 2-continued

Preparation of HKMTi compounds.

| Name | Structure | Intermediate | Method | Calculated Mass | Found Mass |
|---|---|---|---|---|---|
| HKMTi-1-137 | 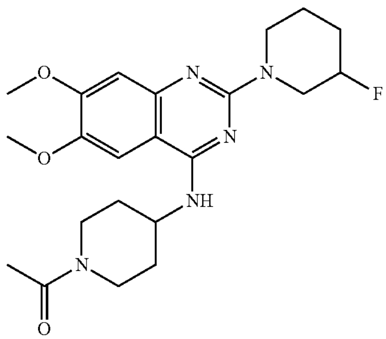 [SMILES: COc1cc2nc(N3CCCC(F)C3)nc(NC3CCN(C(C)=O)CC3)c2cc1OC] | | 3 | 432.4 | 432.4 |
| HKMTi-1-138 | 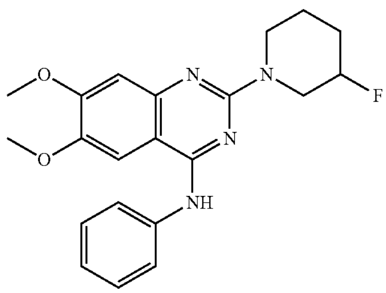 [SMILES: COc1cc2nc(N3CCCC(F)C3)nc(Nc3ccccc3)c2cc1OC] | | 3 | 383.2 | 383.2 |
| HKMTi-1-139 | 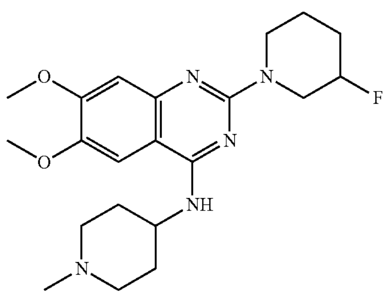 [SMILES: COc1cc2nc(N3CCCC(F)C3)nc(NC3CCN(C)CC3)c2cc1OC] | | 3 | 404.3 | 404.3 |
| HKMTi-1-140 | 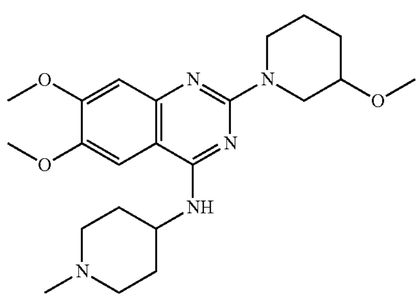 | | 3 | 416.1 | 416.1 |
| HKMTi-1-141 | 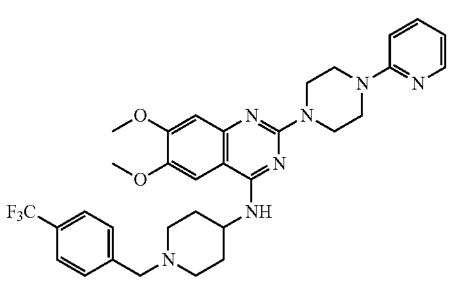 [SMILES: COc1cc2nc(N3CCN(c4ccccn4)CC3)nc(NC3CCN(Cc4ccc(C(F)(F)F)cc4)CC3)c2cc1OC] | | 4 | 608.2961 | 608.2974 |

TABLE 2-continued
Preparation of HKMTi compounds.
| Name | Structure | Intermediate | Method | Calculated Mass | Found Mass |
|---|---|---|---|---|---|
| HKMTi-1-142 | 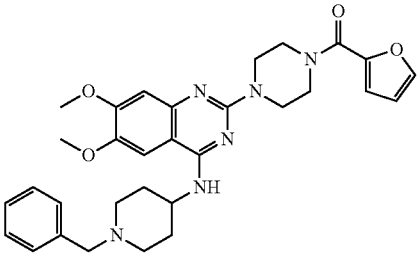 [SMILES: COc1cc2nc(N3CCN(C(=O)c4ccco4)CC3)nc(NC3CCN(Cc4ccccc4)CC3)c2cc1OC] | 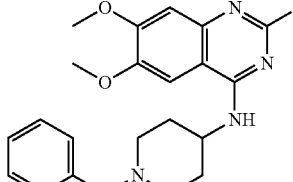 | 4 | 557.2876 | 557.2883 |
| HKMTi-1-152 | 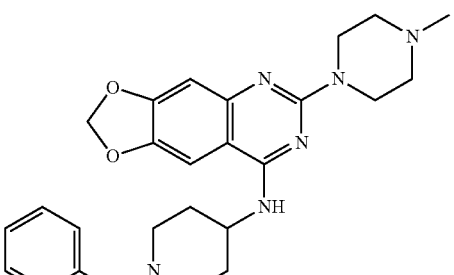 | 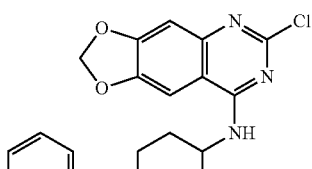 | 5 | 461.2665 | 461.2647 |
| HKMTi-1-153 | 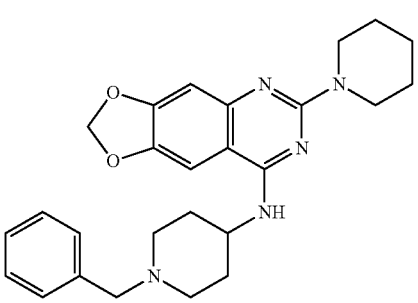 [SMILES: c1ccc(CN2CCC(Nc3nc(N4CCCCC4)nc4cc5c(cc34)OCO5)CC2)cc1] | 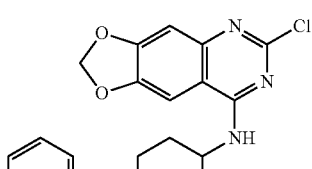 | 5 | 446.2556 | 446.2548 |
| HKMTi-1-154 | 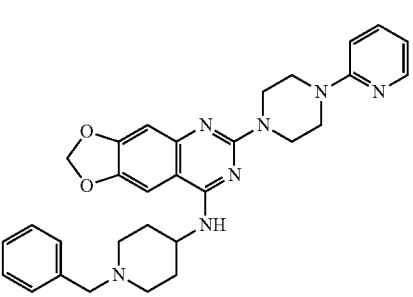 [SMILES: c1ccc(CN2CCC(Nc3nc(N4CCN(c5ccccn5)CC4)nc4cc5c(cc34)OCO5)CC2)cc1] | 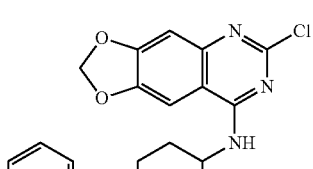 | 5 | 524.2774 | 524.2766 |
| HKMTi-1-155 | 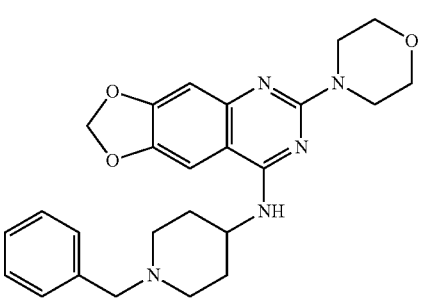 [SMILES: c1ccc(CN2CCC(Nc3nc(N4CCOCC4)nc4cc5c(cc34)OCO5)CC2)cc1] | 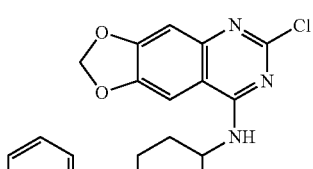 | 5 | 448.2349 | 448.2358 |

TABLE 2-continued

Preparation of HKMTi compounds.

| Name | Structure | Intermediate | Method | Calculated Mass | Found Mass |
|---|---|---|---|---|---|
| HKMTi-1-156 | 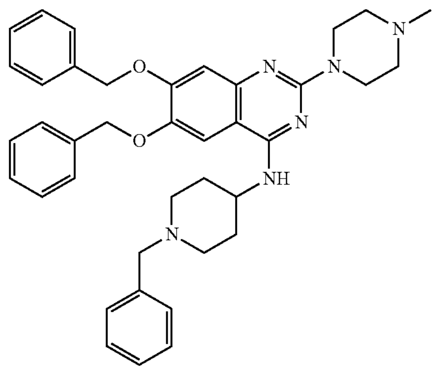 [SMILES: CN1CCN(c2nc(NC3CCN(Cc4ccccc4)CC3)c3cc(OCc4ccccc4)c(OCc4ccccc4)cc3n2)CC1] | | 5 | 629.3604 | 629.3628 |
| HKMTi-1-157 | 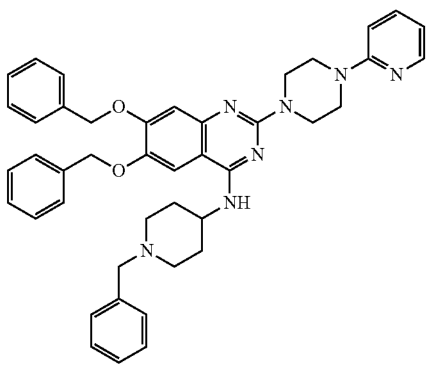 [SMILES: c1ccc(COc2cc3nc(N4CCN(c5ccccn5)CC4)nc(NC4CCN(Cc5ccccc5)CC4)c3cc2OCc2ccccc2)cc1] | | 5 | 692.3719 | 692.3727 |
| HKMTi-1-158 | 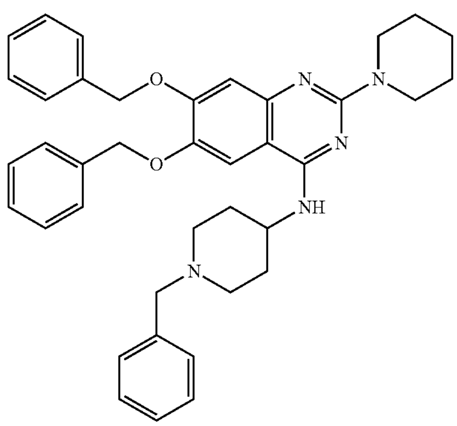 [SMILES: c1ccc(COc2cc3nc(N4CCCCC4)nc(NC4CCN(Cc5ccccc5)CC4)c3cc2OCc2ccccc2)cc1] | | 5 | 614.3495 | 614.3484 |
| HKMTi-1-159 | 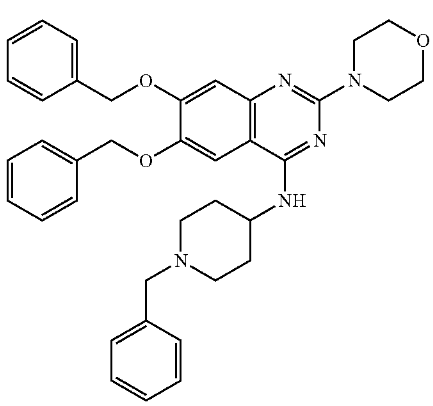 [SMILES: c1ccc(COc2cc3nc(N4CCOCC4)nc(NC4CCN(Cc5ccccc5)CC4)c3cc2OCc2ccccc2)cc1] | | 5 | 616.3288 | 616.3260 |

TABLE 2-continued

Preparation of HKMTi compounds.

| Name | Structure | Intermediate | Method | Calculated Mass | Found Mass |
|---|---|---|---|---|---|
| HKMTi-1-160 | 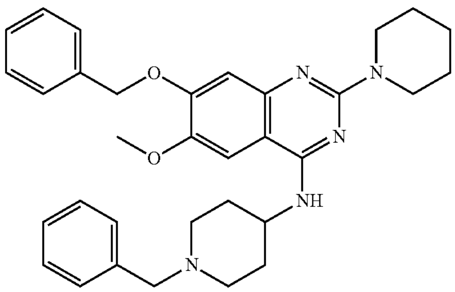 [SMILES: COc1cc2c(NC3CCN(Cc4ccccc4)CC3)nc(N3CCCCC3)nc2cc1OCc1ccccc1] | | 5 | 538.2706 | 538.2725 |
| HKMTi-1-161 | 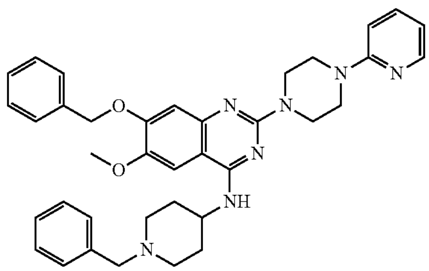 [SMILES: COc1cc2c(NC3CCN(Cc4ccccc4)CC3)nc(N3CCN(c4ccccn4)CC3)nc2cc1OCc1ccccc1] | | 5 | 616.3400 | 616.3408 |
| HKMTi-1-162 | 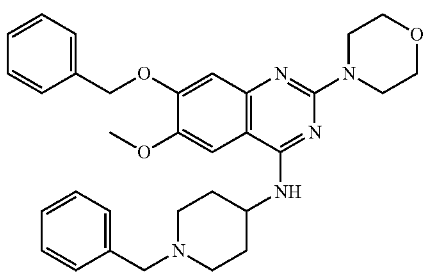 [SMILES: COc1cc2c(NC3CCN(Cc4ccccc4)CC3)nc(N3CCOCC3)nc2cc1OCc1ccccc1] | | 5 | 540.2975 | 540.2951 |
| HKMTi-1-163 | 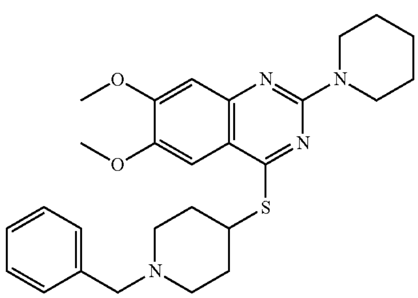 [SMILES: COc1cc2nc(N3CCCCC3)nc(SC3CCN(Cc4ccccc4)CC3)c2cc1OC] | | 4 | 479.2481 | 479.2480 |
| HKMTi-1-164 | 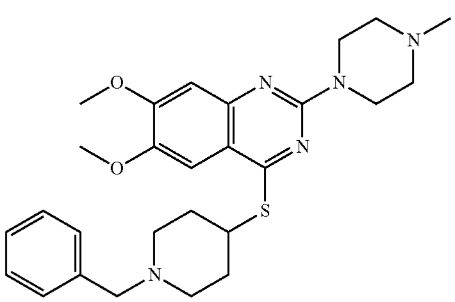 [SMILES: COc1cc2nc(N3CCN(C)CC3)nc(SC3CCN(Cc4ccccc4)CC3)c2cc1OC] | | 4 | 494.2590 | 494.2589 |

TABLE 2-continued

Preparation of HKMTi compounds.

| Name | Structure | Intermediate | Method | Calculated Mass | Found Mass |
|---|---|---|---|---|---|
| HKMTi-1-165 | 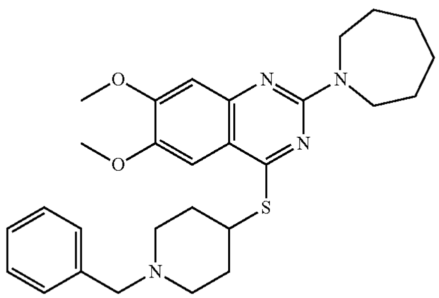 [SMILES: COc1cc2nc(N3CCCCCC3)nc(SC3CCN(Cc4ccccc4)CC3)c2cc1OC] | | 4 | 493.2637 | 493.2617 |
| HKMTi-1-166 | 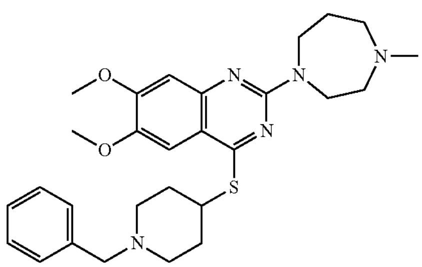 [SMILES: COc1cc2nc(N3CCCN(C)CC3)nc(SC3CCN(Cc4ccccc4)CC3)c2cc1OC] | | 4 | 508.2746 | 508.2742 |
| HKMTi-1-167 | 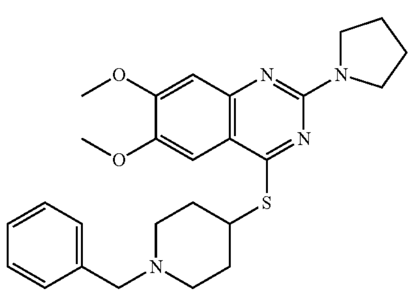 [SMILES: COc1cc2nc(N3CCCC3)nc(SC3CCN(Cc4ccccc4)CC3)c2cc1OC] | | 4 | 465.2324 | 465.2328 |
| HKMTi-1-168 | 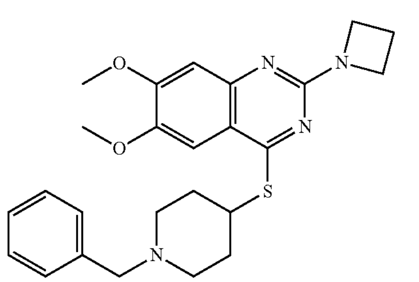 [SMILES: COc1cc2nc(N3CCC3)nc(SC3CCN(Cc4ccccc4)CC3)c2cc1OC] | | 4 | 451.2168 | 451.2159 |

Comparative Example 1

BIX-01294

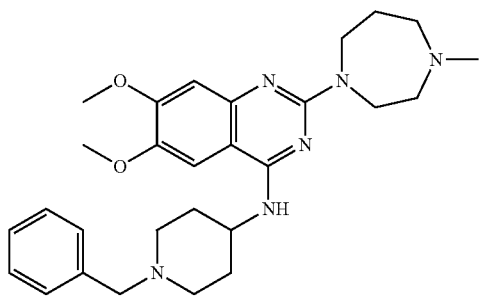

Comparative Example 2

UNC0224

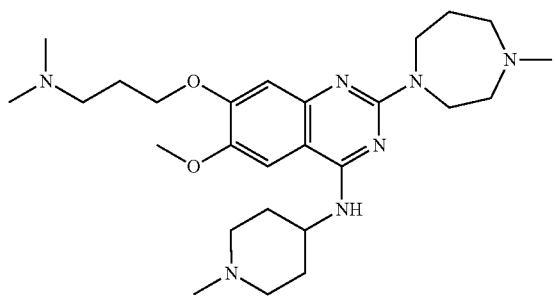

Comparative Example HICNITi-1-012

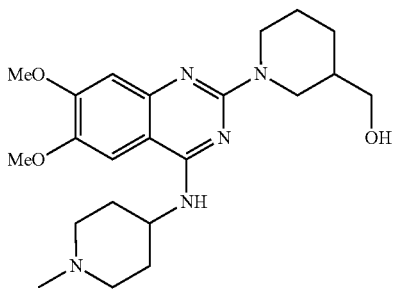 [SMILES: COc1cc2nc(N3CCCC(CO)C3)nc(NC3CCN(C)CC3)c2cc1OC]

Identification of Compounds that Up-Regulate H3K27me3 Silenced Genes by Real-Time RT-PCR.

In order to monitor the reversal of epigenetic silencing associated with H3K27me3, a cell based assay was established using the breast-cancer cell line MDA-MB-231 for which EZH2 expression levels as well as EZH2 target genes have been characterised (17). For initial characterisation of compound activity two genes (KRT17, FBXO32) were selected which are primarily silenced by H3K27me3 in combination with H3K9me2/3 but are not DNA methylated. Furthermore, the DNA methylated gene (RUNX3) was selected to control for effects at loci that are silenced by H3K27me3 in combination with CpG island DNA methylation. The two enzymes which perform H3K27 methylation (EZH2) and demethylation (JMJD3) were also included. Cell death can lead to the down-regulation of EZH2 and up-regulation of JMJD3 in cells (36) and is therefore important to control for indirect effects due to cell death in such a cell-based assay.

Figure 1C:
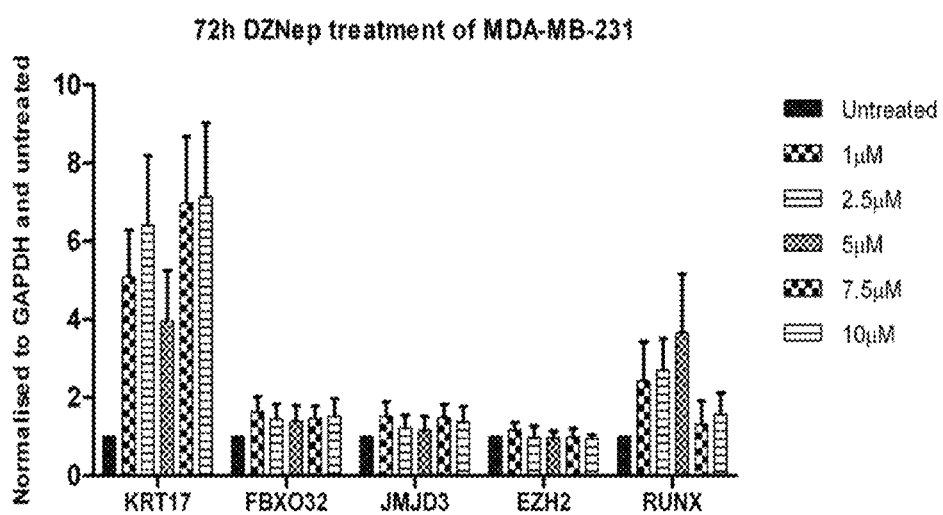
FIG. 1c) Real-time measurement of MDA-MB-231 treated cell lines with DZNep at various concentrations, for 48 and 72 h.

Initially siRNA knockdown experiments against EZH2, G9a and SUV39H1 were performed in order to validate the importance of EZH2 in up-regulation at our selected target genes (FIG. 1b). MDA-MB-231 cells were treated for 48 h with siRNAs at a concentration of 50 nM and monitored for mRNA levels of KRT17, FBXO32, RUNX3, JMJD3 as well as EZH2, G9a and SUV39H1 by real-time RT-PCR. As depicted in FIG. 1b, a target gene knockdown ranging from 70 up to 90% was achieved depending on the siRNA used and HKMT targeted. Importantly, only siRNAs targeting EZH2 were able to up-regulate KRT17 as well as FBXO32. RUNX3 was unaffected (not shown) by any of the siRNAs tested. Although G9a knock-down affected the up-regulation of JMJD3, FBXO32 as well as KRT17 were unaffected. Interestingly, although the siRNA against SUV39H1 was able to decrease levels of EZH2 and up-regulate FBXO32 gene expression, KRT17 was unaffected, again helping to validate the chosen approach for the identification of compounds. These data argue that up-regulation of both KRT17 and FBXO32, with no change at RUNX3, should identify compounds which mediate their effects through inhibition of EZH2 function. Lastly, MDA-MB-231 was treated with DZNep at various concentrations for 48 and 72 h. DZNep is known to non-selectively decrease H3K27me3 levels via depletion of components of the PRC2 complex, while not affecting mRNA expression (17) (FIG. 1c). Only KRT17 was consistently up-regulated, whereas mRNA levels of FBXO32, JMJD3 as well as EZH2 were unaffected. Moreover, expression of the DNA methylated gene RUNX3 was increased under certain conditions although not in a dose dependent manner. This is consistent with the previously reported lack of specificity of DZNep (18).

In order to identify compounds which can mediate the reactivation of PRC2 silenced genes, MDA-MB-231 cells were treated for 48 h at a concentration of 10 μM of Example compounds 3 (HKMTi-1-005), 4 (HKMTi-1-022) or 5 (HKMTi-1-011), as well as with the comparative examples BIX-01294 or UNC0224, and mRNA levels of KRT17, FBXO32, RUNX3, as well as EZH2 and JMJD3 were measured by real-time RT-PCR. The data were normalised against the housekeeping gene GAPDH as well as RNA pol II (only results for GAPDH are shown, although consistent results were obtained with RNA pol II normalisation). Example compounds 3 (HKMTi-1-005), 4 (HKMTi-1-022) and 5 (HKMTi-1-011) were found to up-regulate KRT17 and FBXO32 RNA levels, while not effecting RUNX3 expression. The data for these compounds along with the comparative example compounds BIX01294 and UNC0224 are shown in FIG. 4 (Table 1). The reported G9a/GLP specific inhibitors BIX01294 and UNC0224 have a very different activity profile on gene expression. Indeed, BIX01294 (FIG. 4 (Table 1), entry 1) does not up-regulate KRT17, but does up-regulate FBXO32. As seen for the siRNA experiments (FIG. 1b) this profile is not consistent with direct H3K27me3 inhibition, but is compatible with the observation that FBXO32 is regulated via multiple mechanisms, potentially responding to a variety of factors (38). In contrast UNC0224 (FIG. 4 (Table 1), entry 2) shows very little effect on both KRT17 and FBX032, consistent with the G9a siRNA data. Similar results to those observed for example compounds 3 (HKMTi-1-005), 4 (HKMTi-1-022) and 5 (HKMTi-1-011) in the cell assay were observed for HKMTi-1-169 and further compounds, as shown in Table 1 in FIG. 4. This indicates that each of the example compounds of the invention are inhibitors of EZH2.

Figure 1D:
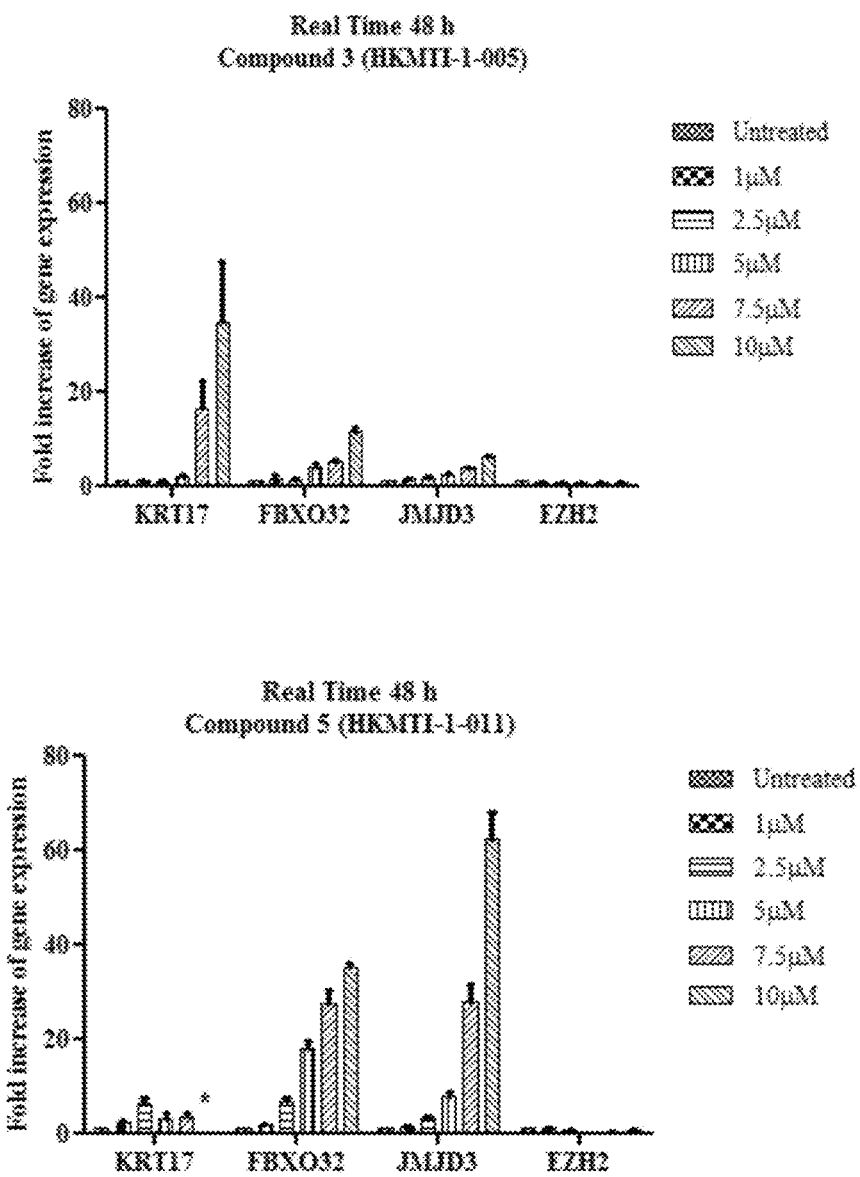
FIG. 1d+e) Sybr green real-time mRNA level measurement of EZH2 target genes and executing enzymes following a (d) 48 h or (e) 72 h compound treatment at different concentrations of MDA-MB-231 cells. All compounds tested consistently increase mRNA levels of KRT17, FBXO32 and JMJD3 in a dose dependent manner and display a decrease in EZH2 levels. Measurements marked with an are below detection limit, most likely due to cell death. Error bars represent standard errors. All RT-PCR experiments were performed in triplicate, normalised to GAPDH and displayed as fold difference to the untreated sample.
Figure 1E:
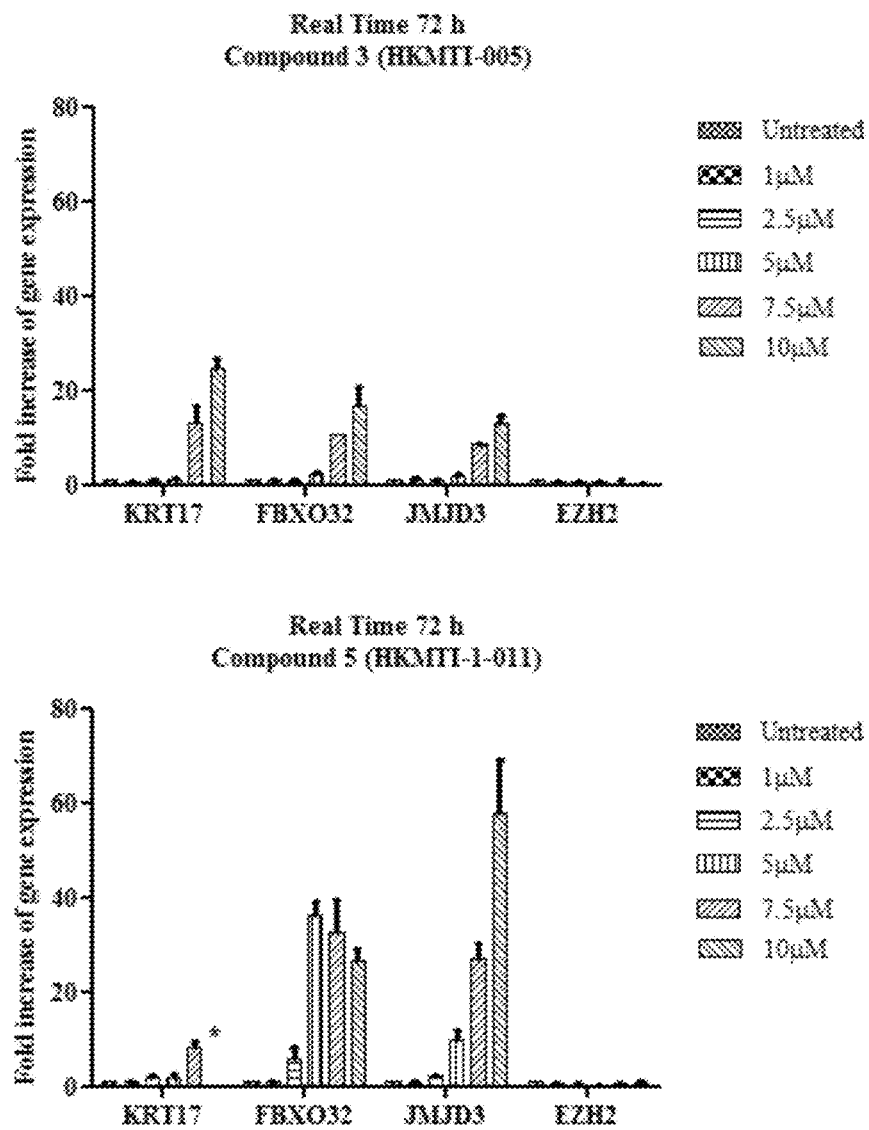
FIG. 1b) siRNA experiments against EZH2, G9a and SUV39H1 using 50 nM of siRNA transfected onto MDA-MB-231 breast cancer cell lines. A knockdown between 70 and up to 90% depending on target genes was achieved.

To characterise example compounds 3 (HKMTi-1-005), 4 (HKMTi-1-022) and 5 (HKMTi-1-011) further, MDA-MB-231 cells were treated for 48 h and 72 h at various concentrations (FIGS. 1d and e). Example 3 (HKMTi-1-005) showed a dose-dependent increase of KRT17, FBXO32 as well as JMJD3 with constant GAPDH levels. Example compounds 4 (HKMTi-1-022) and 5 (HKMTi-1-011) also displayed an increase in a dose dependent manner, although FBXO32 levels increased to more than 20 fold at higher doses. At higher doses of compounds cell death started to occur, particularly at 72 h, which coincides with a dramatic drop in GAPDH levels. At these doses, expression of KRT17 was often below the detection limit of low-expressed genes due to cell death (indicated as "*" in FIGS. 1d and e). Independently synthesised batches of Example compounds 3 (HKMTi-1-005), 4 (HKMTi-1-022) and 5 (HKMTi-1-011) were prepared and assessed to ensure reproducibility of our results and indeed confirmed that those compounds could induce gene re-expression of KRT17 and FBXO32.

Figure 2A:
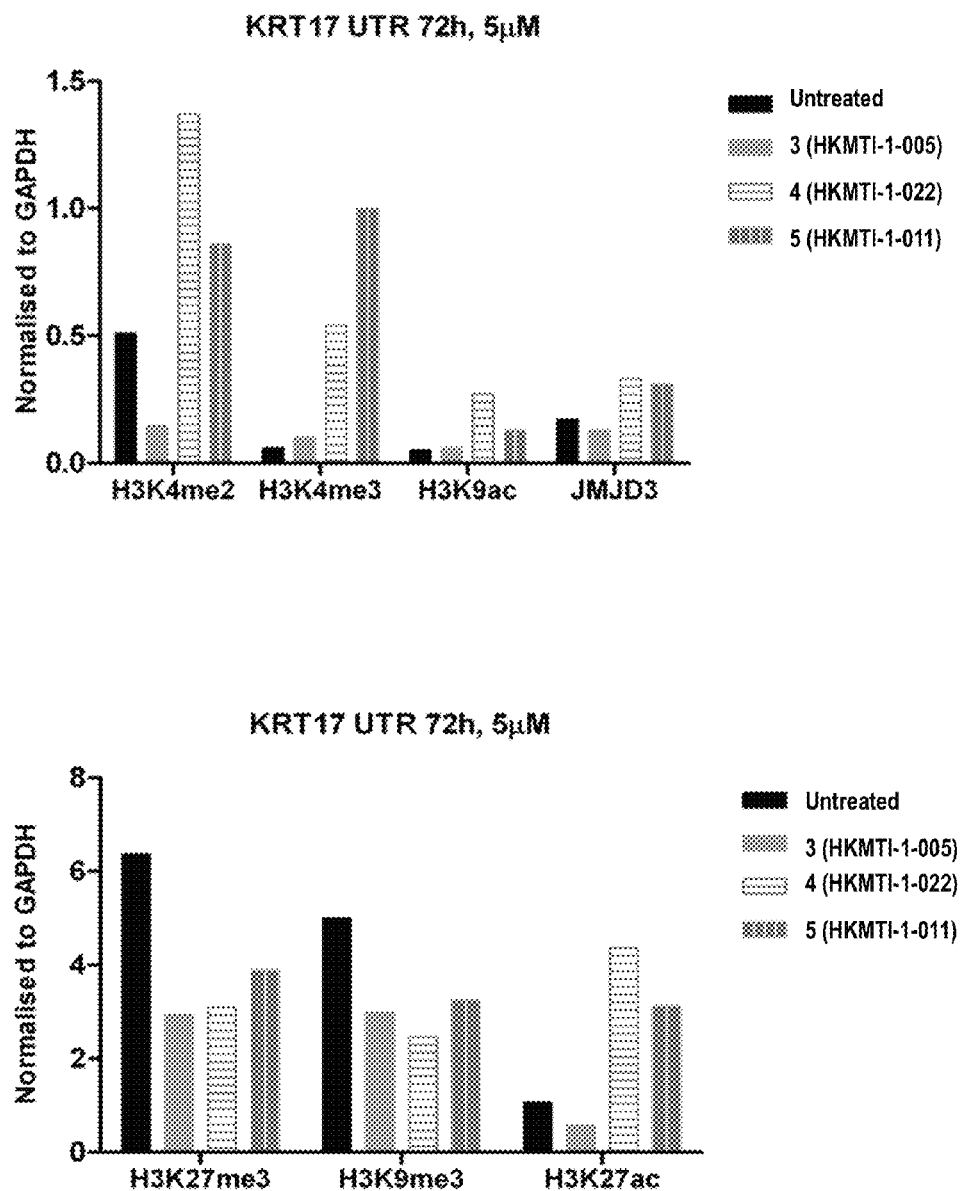
FIG. 2 shows compound-induced changes in histone marks Sybr green real-time measurement of the (a) KRT17 and (b) FBXO32 promoter region following Chromatin Immunoprecipitation, using antibodies to the histone marks shown, of MDA-MB-231 cells treated with 3 selected compounds at 5 µM for 72 h. Shown are representative examples of a series of ChIP experiments which consistently showed similar changes. The fold difference to the untreated sample is shown. Each IP-value has been determined as the relative increase to the no-antibody control and then normalised to GAPDH levels.
Figure 2B:
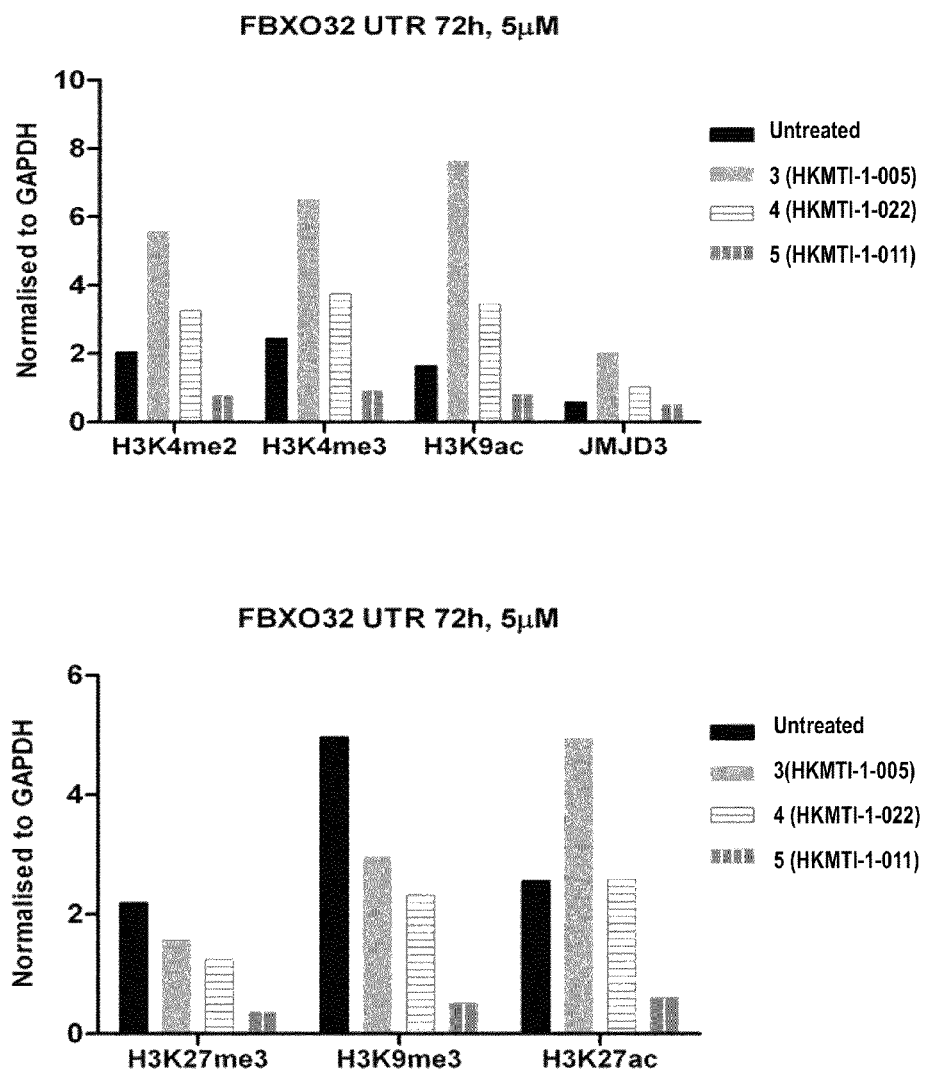

ChIP Shows Decrease of Silencing and Increase of Activating Marks at KRT17 and FBXO32 Promoter Chromatin Immunoprecipitation (ChIP) experiments were carried out on treated MDA-MB-231 cells to verify that the detected gene up-regulation is indeed due to chromatin remodelling (FIG. 2). For this, typical silencing marks such as H3K9me3 and H3K27me3 were tested as well as activating marks such as H3K4me3, H3K27ac and H3K9ac. All three example compounds 3 (HKMTi-1-005), 4 (HKMT-1-022) and 5 (HKMT-1-011) showed a clear decrease in repressive chromatin marks (H3K27me3, H3K9me3) at both genes, FIGS. 2 a and b. Compound 4 (HKMT-1-022) showed a concomitant increase in all permissive chromatin marks examined (H3K4me3, H3K4me2, H3K9ac and H3K27ac) as well as an increase in JMJD3 binding (FIG. 2). Compounds 3 (HKMTi-1-005) and 5 (HKMTi-1-011) (TG3-178-2) showed an increase in most permissive marks, but compound 3 (HKMTi-1-005) did not gain all active marks at KRT17, while compound 5 (HKMTi-1-011) did not gain all active marks at FBXO32. It should be noted that greater than 50% cell death is observed for compound 5 (HKMTi-1-011) at this concentration, but not for the others, and the changes observed in histone marks for compound 5 (HKMT-1-011) may reflect ongoing cell death.

Growth Inhibition of Breast Cell Lines

Figure 3A:
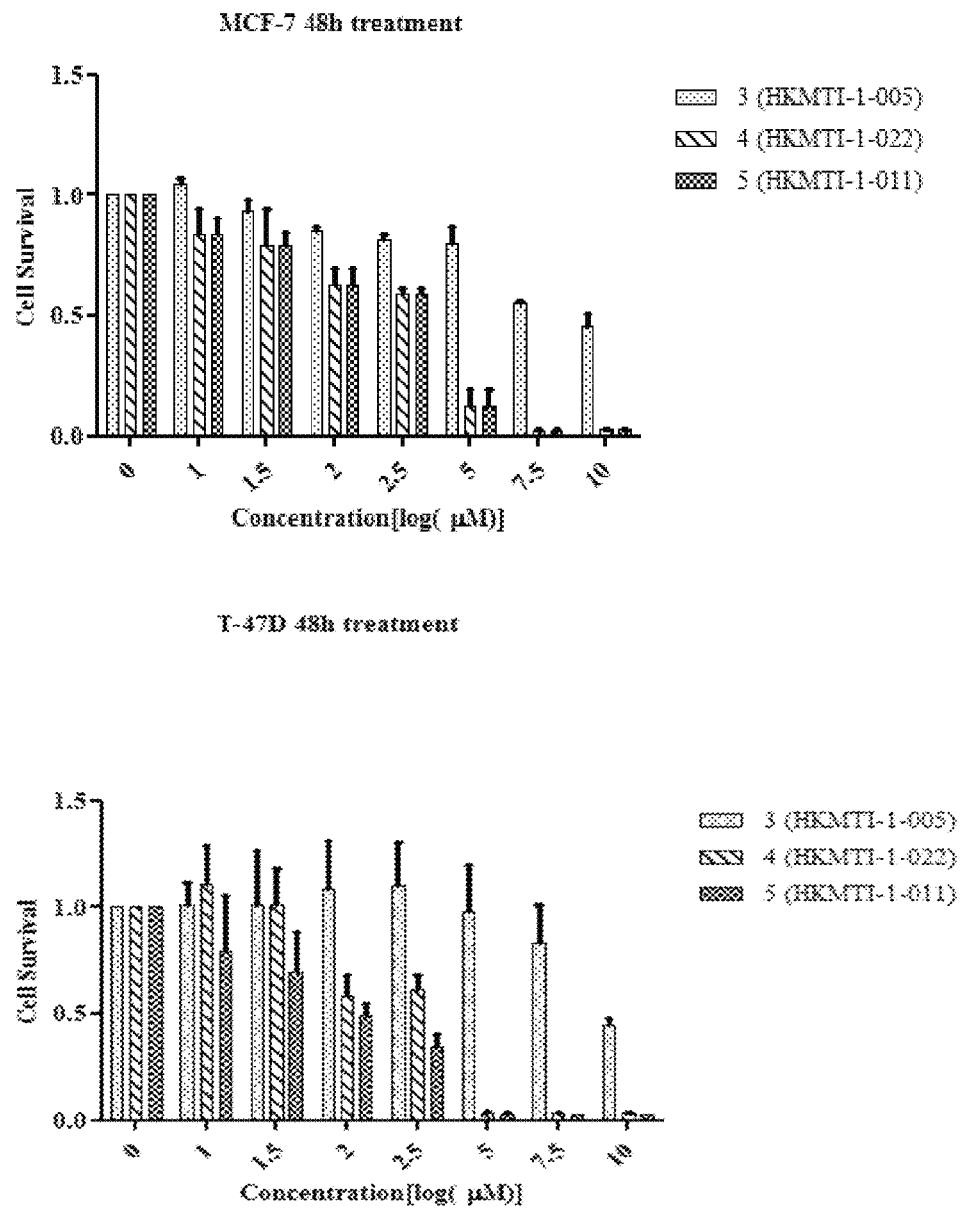
FIG. 3a) MTT cell viability assay results for breast cancer cells lines and the 'normal' breast cell line MCF10a under growth stimulating conditions (EGF). All MTT assays were done in triplicate. Error bars are standard errors.

In order to test whether Example compounds 3 (HKMTi-1-005), 4 (HKMT-1-022) and 5 (HKMT-1-011) would show growth inhibition in a series of breast cancer cell lines cell viability assays were performed (FIG. 3a). The panel of cell lines included ER positive and negative breast cancer cell lines (ER-pos [T47D, MCF7, BT474], ER-neg [MDA-MB-231, BT549, SKBR3]). To test whether an untransformed epithelial breast cell line would also be affected by the compounds identified, we included the breast cell line MCF-10a for comparison. Generally, the normal MCF$_{10}$a cell line (under EGF growth stimulated condition) was more resistant (IC$_{50}$ values range from 14 to 45 µM) to compound treatment than the other breast cancer cell lines tested. The most sensitive cell lines were BT474 and SKBR3, showing low IC$_{50}$ values of 1 to 2 µM. Interestingly both these lines have the lowest expression of EZH2 protein levels by Western analysis (FIG. 3b).

Genome-Wide Changes in Gene Expression of EZH2 Target Genes Induced by Compounds.

Agilent two-colour microarrays were used to profile gene expression changes induced 24 h and 48 h after 10 µM treatment with example compound 3 (HKMTi-1-005) compared to compound HKMTi-1-012. Using LIMMA to assess statistical significance of differential expression upon treatment of MDA MB-231 cells with each drug, the number of significantly up-regulated and down-regulated genes following each drug treatment is given in FIG. 5 (Table 2). The effects of EZH2 knockdown on MDA MB-231 cells have previously been studied, with gene expression microarray profiling upon EZH2 siRNA treatment being used to define lists of genes repressed or transcriptionally upregulated by EZH2 (Lee et al 2011). Many of these EZH2 target genes are clearly differentially expressed following treatment with example compound 3 (HKMTi-1-005) compared to compound HKMTi-1-012, as shown in Table 2 in FIG. 5. Statistical enrichment of EZH2-target genes (Lee et al 2011) in the lists of differentially expressed genes was evaluated using the hypergeometric distribution. Example compound 3 (HKMTi-1-005) results in significant upregulation (p=$3.3^{-33}$ at 24 h and p=$3.2^{-21}$ at 48 h) and significant down-regulation (p=$3.5^{-37}$ at 24 h and p=$3.8^{-61}$ at 48 h) of EZH2 target genes.

Following analysis of changes in expression of EZH2 target genes induced by example compound 3 (HKMTi-1-005), significant changes in other relevant pathways was examined using DAVID to look at functional enrichments. The most significant associations are an upregulation of apoptosis genes and the lysosome pathway, and a down-regulation of a number of processes related to cell cycle & cell division.

Discussion:

Compounds have been identified which reverse epigenetic silencing at endogenous KRT17 and FBXO32 genes in breast cancer cells where the H3K27me3 epigenetic mark is known to be maintained by EZH2 histone methyltransferase activity and involved in the establishment of transcriptional silencing. Subsequent ChIP experiments confirmed that the observed re-expression was accompanied by a decrease of H3K27me3 as well as H3K9me3 silencing marks for all three compounds at the promotor regions of KRT17/FBX032, and an increase of the activating marks H3K4me3, H3K27ac and H3K9ac for compound 4 (HKMTi-1-022).

The comparative example BIX01294 has been shown to have relatively high selectivity towards G9a and GLP (21). BIX01294 does not up-regulate KRT17, which is consistent with the previously published inability to target PRC2 mediated gene silencing and our siRNA data. Another known G9a/GLP inhibitor, UNC0224, had very little effect in our assay. The results for the example compounds of the invention are not consistent with selective G9a inhibition. The data for the example compounds of the invention is consistent with inhibition of the function of PRC2, which is believed to be via direct inhibition of EZH2 in cells. The global changes in expression induced at genes known to be EZH2 targets from siRNA knockdown in MDA-MB231 cells is consistent with this interpretation of inhibition of EZH2 activity.

The MDA-MB-231 cell based assay focusing on the reversal of EZH2 related gene silencing suggests HKMT inhibition leads to reactivation of gene expression which in turn triggers cell death. Gene Ontology analysis by DAVID shows functional enrichment for apoptosis pathways for genes which show significant changes in gene expression following hit compound treatment. While these effects are observed already at 24 h, they nevertheless could represent secondary indirect alterations following changes at EZH2 targets. However, direct effects are also possible. For instance, up-regulation of FBXO32 has been established to trigger apoptosis (40). Treatment of cells with active compounds results in up-regulation of FBXO32 and KRT17, accompanied by chromatin changes detected at the promoter regions via ChIP (FIG. 2b) prior to any detectable cell death. In contrast to DZNep which leads to a depletion of PRC2 and the concomitant reduction of H3K27me3 levels, the active compounds we have identified do not deplete EZH2 levels per se but rather lead initially to a local H3K27me3 and H3K9me3 reduction on EZH2 target promoter regions rather than reducing all histone methylation marks. However, once cell death is initiated this will lead to reduced levels of EZH2.

Knock-down of EZH2 expression in tumour cells blocks tumour cell growth (14-16). The example compounds of the invention show cellular growth inhibition. It is encouraging that the normal breast epithelial line is the most resistant to the compounds. The trend of sensitivity of breast cancer cell lines with low EZH2 levels is consistent with growth inhibition being dependent on EZH2 levels.

Taken together, the data is consistent with the identification of small molecule compounds which reactivate gene expression through the targeting of negative chromatin remodelers, allowing establishment of permissive chromatin marks and, hence, leading to reversal of epigenetic silencing of genes in tumour cells by inhibiting maintenance of the repressive state leading to cell death.

Experimental Procedures

Cell culture and compound treatment: MDA-MB-231, T47D, MCF7, BT474, BT549 and SKBR3 breast cancer cell lines were cultured in DMEM-Medium supplemented with 10% FCS (#02.00.830, First Link (UK), 2 mM L-Glutamine (#25030-024, Invitrogen), 100 U/ml Penicillin and 100 μg/ml Streptavidin (#15070-063, Invitrogen) until they were ~60% confluent and then treated for either 48 h or 72 h with a compound. Compounds were diluted in DMSO at Stocks of 10 mM. MCF-10a breast cell lines were cultured in DMEM/F12-Medium supplemented with 5% horse serum, EGF (20 ng/ml), Hydrocortizone (0.5 mg/ml), Cholera Toxin (100 ng/ml), Insulin (10 μg/ml) as well as 100 U/ml Penicillin and 100 μg/ml Streptavidin (#15070-063, Invitrogen). For MTT experiments, cells were either kept in DMEM/F12 growth medium or in normal DMEM-Medium to mimic the 'normal' non-dividing cell state.

Real-Time Measurements for Cell Based Screening:

Following compound treatment for 48 h (in 6-well plates), media was removed and 1.5 ml of TRIzol (#155966018, Invitrogen) was added directly to lyse cells. Once cells were lysed, the protocol was continued with 1 ml (TRIzol, cell lysate) according to the manufactures instructions. Purified RNA was dissolved in 35 μl of UltraPure DNase/RNase-free distilled water (#10977049, Invitrogen). Reverse transcription was done using the SuperScript III First-Strand Synthesis System (#18080-051, Invitrogen) according to the manufactures instructions, using 7 μl of the purified RNA as starting material. For real-time measurements the 2×iQ SYBR Green Supermix (#170-8882, Bio-Rad), 200 nM Primers and 0.4 μl of cDNA/per 20 μl reaction was used. The measurement was done in low-white 96-well plates (#MLL9651, Bio-Rad) on a CFX96 Real-time System/ C1000 Thermal Cycler (Bio-Rad) with the following protocol: 95° C. for 3'; 95° C. for 10", 56° C. for 10", 72° C. for 30" 42 cycles followed by a melting curve from 72° C. to 95° C. in order to control for primer dimer or unwanted products. Each measurement was done in triplicate, and the List of Primers can be found in FIG. 6 (Supplementary Table 1). For normalisation we have tested numerous 'housekeeping genes' such as β-actin, HPRT1 as well as TBP, but in our hands, for drug treatment purposes only GAPDH as well as RNA pol II seem to be a reliable constant normaliser. In order to account for preparation/handling differences during drug treatment and real-time measurement, we are using a second GAPDH (GAPDH_2) primer pair, and would count an experiment as valid if the difference between these primer pairs is not greater than +/−0.15 fold for each real-time run.

Real-Time Measurement Using Cell-to-CT-Kit:

Experiments were done with the 'Fast Sybr Green Cell-to-CT™-Kit' (4402957M) according to the manufacture's instructions (Applied Biosystem). Per 96 well/15,000 cells were plated and after 24 h treated with compounds at various concentrations. We believe this is crucial in order to detect the effect of the compound tested as higher cell concentrations of 30,000 tend to mask the effect otherwise seen. Conditions were used as described above for real-time measurement.

SiRNA Experiments:

SiRNA experiments were done on the MDA-MB-231 cell line using Qiagen reagents, according to the manufactures instructions. In brief, cells were seeded at a density of $1\times10^5$ cells/6 cm well and siRNA treated for 48 h. HiPerfect, Optimem and 50 nM of G9a (SI00091189 HS_BAT8 1, SI03083241 HS_EHMT2), SUV39H1 (SI02665019 HS_SUV39H1 6, SI00048685 HS_SUV39H1 4) and EZH2 (SI00063973 HS_EZH2 4, SI02665166 HS_EZH2 7) siRNA were used for transfections according to the manufactures instructions (Supplementary Table 3 of FIG. 8). The transfection mixture was added drop-wise onto 30% confluent cells and incubated for 48 h after which RNA was extracted as described above.

Chromatin Immunoprecipitation (ChIP) Assay:

ChIP was accomplished using Dynabeads Protein A (Invitrogen #100-01D.) according to (41), except that following the Chelex-DNA purification an additional purification with QIAquick PCR Purification Kit (#28106, Qiagen) was carried out, here the ChIP-products were eluted in 50 μl and for subsequent real-time measurements (as described above) 1.5 μl per reaction was used. The list of Primers can be found in FIG. 7 (Supplementary Table 2). Results were calculated as a fold increase of the No-antibody control and then normalised to GAPDH (active marks) and beta-globin (inactive marks).

MTT-Assay:

MDA-MB-231 cells were seeded at a density of 10000 cells/well in a sterile 96 clear-well plate with 150 μl of DMEM (+10% FCS and 2 mM L-Glutamine). Cells were grown for 24 hr at 37° C. in a $CO_2$ incubator until cells were ~70-90% confluent. Each compound treatment was performed in triplicate for 72 h at concentrations of 100 nM, 1 μM, 5 μM, 10 μM and 50 μM in 100 μl of full-medium. After 72 h, 20 μl of MTT solution (3 mg of MTT Formazan #M2003, Sigma/1 ml PBS (in house) was added to the medium, thoroughly mixed and incubated for 4 h at 37° C. in a $CO_2$-incubator. Media was removed and paper towel tapped-dry, the MTT-product was solubilised with 100 μl DMSO and for 1 h incubated in the dark at room-temperature. The optical density was read at 570 nm with PHERAstar.

Westernblot:

MDA-MB-231 were treated with compounds at various concentrations for 72 h, then washed twice with ice-cold PBS and subsequently lysed in RIPA buffer (Thermo Scientific Pierce) containing Protease (Sigma) for 15 min on ice, harvested, and spun down for 15 min at 14.800 rpm. For each SDS-gel 30 µg of protein extract was loaded and afterwards blotted onto a Nitrocellulose membrane (Bio-Rad). Following the transfer, the membrane was blocked for an hour with 5% milk in TBS and then incubated with the first antibody overnight at 4° C. First antibodies were used at the following concentrations: β-Actin (Abeam, ab6276) 1/10000, EZH2 (Cell signalling, #3147) 1/1000, H3K27me3 (Millipore, #07-449). Secondary antibodies used were incubated for 1 hour as follows: Mouse IGg HRP (Santa Cruz Biotechnology, SC-2005) 1/200, Goat anti Rabbit IGg HRP (Millipore, #12-348) 1/5000, Goat anti Rabbit IGg HRP (Dako, Po448) 1/2000.

Gene Expression Microarrays:

Agilent 80 k two-colour microarrays were used to profile gene expression changes induced by treatment with drug compounds in MDA MB-231 cells, both at 24 h and 48 h. 4 replicates were used for each drug, time combination. A separate untreated control sample was used for comparison with each replicate. Sample labelling, array hybridization and scanning were performed by Oxford Gene Technologies, according to manufacturer's instructions. Feature Extracted files were imported into GeneSpring (Agilent) and data was normalised to produce log 2 ratios of treated/ untreated for each replicate of each drug, time combination.

Statistical Analysis:

Differential Expression

Normalised log 2 gene expression ratios were analysed using LIMMA (Smyth 2004) to obtain empirical Bayes moderated t-statistics reflecting statistical significance of differential expression across the 4 replicates for each drug, time combination. Multiple testing adjustment was made using the Benjamini-Hochberg method, following which a threshold of $p<0.05$ was used to denote significant differential expression.

Enrichment Analysis

A list of EZH2 targets in the MDA MB-231 cell line was obtained from a previous study (Lee et al 2011), and separated into genes repressed by EZH2 (upregulated on EZH2 knockdown) and genes transcriptionally activated by EZH2 (downregulated on EZH2 knockdown). Statistical significance of overlap between these lists of EZH2 targets and the genes differentially expressed upon drug treatment in our microarray study was assessed using the hypergeometric distribution.

REFERENCE LIST (1) Sharma S, Kelly T K, Jones P A. Epigenetics in cancer. Carcinogenesis 2010; 31:27-36.
(2) Jones P A, Baylin S B. The fundamental role of epigenetic events in cancer. Nat Rev Genet 2002; 3:415-28.
(3) Kondo Y, Shen L, Cheng A S, Ahmed S, Boumber Y, Charo C, et al. Gene silencing in cancer by histone H3 lysine 27 trimethylation independent of promoter DNA methylation. Nat Genet. 2008; 40:741-50.
(4) Chapman-Rothe N, Brown R. Approaches to target the genome and its epigenome in cancer. Future Med Chem 2009; 1:1481-95.
(5) Cao R, Zhang Y. The functions of E(Z)/EZH2-mediated methylation of lysine 27 in histone H3. Curr Opin Genet Dev 2004; 14:155-64.
(6) Hansen K H, Bracken A P, Pasini D, Dietrich N, Gehani S S, Monrad A, et al. A model for transmission of the H3K27me3 epigenetic mark. Nat Cell Biol 2008; 10:1291-300.
(7) Margueron R, Li G, Sarma K, Blais A, Zavadil J, Woodcock C L, et al. Ezh1 and Ezh2 maintain repressive chromatin through different mechanisms. Mol Cell 2008; 32:503-18.
(8) Shen X, Liu Y, Hsu Y J, Fujiwara Y, Kim J, Mao X, et al. EZH1 mediates methylation on histone H3 lysine 27 and complements EZH2 in maintaining stem cell identity and executing pluripotency. Mol Cell 2008; 32:491-502.
(9) Pietersen A M, Horlings H M, Hauptmann M, Langerod A, Ajouaou A, Cornelissen-Steijger P, et al. EZH2 and BMI1 inversely correlate with prognosis and TP53 mutation in breast cancer. Breast Cancer Res 2008; 10:R109.
(10) Yu J, Yu J, Rhodes D R, Tomlins S A, Cao X, Chen G, et al. A polycomb repression signature in metastatic prostate cancer predicts cancer outcome. Cancer Res 2007; 67:10657-63.
(11) Rao Z Y, Cai M Y, Yang G F, He L R, Mai S J, Hua W F, et al. EZH2 supports ovarian carcinoma cell invasion and/or metastasis via regulation of TGF-beta1 and is a predictor of outcome in ovarian carcinoma patients. Carcinogenesis 2010; 31:1576-83.
(12) Lu C, Han H D, Mangala L S, Ali-Fehmi R, Newton C S, Ozbun L, et al. Regulation of tumor angiogenesis by EZH2. Cancer Cell 2010; 18:185-97.
(13) Min J, Zaslaysky A, Fedele G, McLaughlin S K, Reczek E E, De R T, et al. An oncogene-tumor suppressor cascade drives metastatic prostate cancer by coordinately activating Ras and nuclear factor-kappaB. Nat Med 2010; 16:286-94.
(14) Fussbroich B, Wagener N, Macher-Goeppinger S, Benner A, Faith M, Sultmann H, et al. EZH2 depletion blocks the proliferation of colon cancer cells. PLoS One 2011; 6:e21651.
(15) Kamminga L M, Bystrykh L V, de B A, Houwer S, Douma J, Weersing E, et al. The Polycomb group gene Ezh2 prevents hematopoietic stem cell exhaustion. Blood 2006; 107:2170-9.
(16) Rizzo S, Hersey J M, Mellor P, Dai W, Santos-Silva A, Liber D, et al. Ovarian cancer stem cell-like side populations are enriched following chemotherapy and overexpress EZH2. Mol Cancer Ther 2011; 10:325-35.
(17) Tan J, Yang X, Zhuang L, Jiang X, Chen W, Lee P L, et al. Pharmacologic disruption of Polycomb-repressive complex 2-mediated gene repression selectively induces apoptosis in cancer cells. Genes Dev 2007; 21:1050-63.
(18) Miranda T B, Cortez C C, Yoo C B, Liang G, Abe M, Kelly T K, et al. DZNep is a global histone methylation inhibitor that reactivates developmental genes not silenced by DNA methylation. Mol Cancer Ther 2009; 8:1579-88.
(19) Daigle S R, Olhava E J, Therkelsen C A, Majer C R, Sneeringer C J, Song J, et al. Selective killing of mixed lineage leukemia cells by a potent small-molecule DOT1L inhibitor. Cancer Cell 2011; 20:53-65.
(20) Yao Y, Chen P, Diao J, Cheng G, Deng L, Anglin J L, et al. Selective inhibitors of histone methyltransferase DOT1L: design, synthesis, and crystallographic studies. J Am Chem Soc 2011; 133:16746-9.
(21) Kubicek S, O'Sullivan R J, August E M, Hickey E R, Zhang Q, Teodoro M L, et al. Reversal of H3K9me2 by a small-molecule inhibitor for the G9a histone methyltransferase. Mol Cell 2007; 25:473-81.
(22) Shi Y, Do J T, Desponts C, Hahm H S, Scholer H R, Ding S. A combined chemical and genetic approach for the generation of induced pluripotent stem cells. Cell Stem Cell 2008; 2:525-8.

(23) Shi Y, Desponts C, Do J T, Hahm H S, Scholer H R, Ding S. Induction of pluripotent stem cells from mouse embryonic fibroblasts by Oct4 and Klf4 with small-molecule compounds. Cell Stem Cell 2008; 3:568-74.

(24) Imai K, Togami H, Okamoto T. Involvement of histone H3 lysine 9 (H3K9) methyltransferase G9a in the maintenance of HIV-1 latency and its reactivation by BIX01294. J Biol Chem 2010; 285:16538-45.

(25) Liu F, Chen X, Allali-Hassani A, Quinn A M, Wasney G A, Dong A, et al. Discovery of a 2,4-diamino-7-aminoalkoxyquinazoline as a potent and selective inhibitor of histone lysine methyltransferase G9a. J Med Chem 2009; 52:7950-3.

(26) Liu F, Chen X, Allali-Hassani A, Quinn A M, Wigle T J, Wasney G A, et al. Protein lysine methyltransferase G9a inhibitors: design, synthesis, and structure activity relationships of 2,4-diamino-7-aminoalkoxy-quinazolines. J Med Chem 2010; 53:5844-57.

(27) Liu F, Barsyte-Lovejoy D, Allali-Hassani A, He Y, Herold J M, Chen X, et al. Optimization of cellular activity of G9a inhibitors 7-aminoalkoxy-quinazolines. J Med Chem 2011; 54:6139-50.

(28) Vedadi M, Barsyte-Lovejoy D, Liu F, Rival-Gervier S, Allali-Hassani A, Labrie V, et al. A chemical probe selectively inhibits G9a and GLP methyltransferase activity in cells. Nat Chem Biol 2011; 7:566-74.

(29) Chang Y, Zhang X, Horton J R, Upadhyay A K, Spannhoff A, Liu J, et al. Structural basis for G9a-like protein lysine methyltransferase inhibition by BIX-01294. Nat Struct Mol Biol 2009; 16:312-7.

(30) Wu H, Chen X, Xiong J, Li Y, Li H, Ding X, et al. Histone methyltransferase G9a contributes to H3K27 methylation in vivo. Cell Res 2011; 21:365-7.

(31) Pasini D, Bracken A P, Jensen M R, Lazzerini D E, Helin K. Suz12 is essential for mouse development and for EZH2 histone methyltransferase activity. EMBO J. 2004; 23:4061-71.

(32) Sarma K, Margueron R, Ivanov A, Pirrotta V, Reinberg D. Ezh2 requires PHF1 to efficiently catalyze H3 lysine 27 trimethylation in vivo. Mol Cell Biol 2008; 28:2718-31.

(33) Wang Z, Zang C, Rosenfeld J A, Schones D E, Barski A, Cuddapah S, et al. Combinatorial patterns of histone acetylations and methylations in the human genome. Nat Genet. 2008; 40:897-903.

(34) Bannister A J, Kouzarides T. Regulation of chromatin by histone modifications. Cell Res 2011; 21:381-95.

(35) Ringrose L, Paro R. Epigenetic regulation of cellular memory by the Polycomb and Trithorax group proteins. Annu Rev Genet. 2004; 38:413-43.

(36) Barradas M, Anderton E, Acosta J C, Li S, Banito A, Rodriguez-Niedenfuhr M, et al. Histone demethylase JMJD3 contributes to epigenetic control of INK4a/ARF by oncogenic RAS. Genes Dev 2009; 23:1177-82.

(37) Chang Y, Ganesh T, Horton J R, Spannhoff A, Liu J, Sun A, et al. Adding a lysine mimic in the design of potent inhibitors of histone lysine methyltransferases. J Mol Biol 2010; 400:1-7.

(38) Foletta V C, White L J, Larsen A E, Leger B, Russell A P. The role and regulation of MAFbx/atrogin-1 and MuRF1 in skeletal muscle atrophy. Pflugers Arch 2011; 461:325-35.

(39) Greiner D, Bonaldi T, Eskeland R, Roemer E, Imhof A. Identification of a specific inhibitor of the histone methyltransferase SU(VAR)$_{3-9}$. Nat Chem Biol 2005; 1:143-5.

(40) Chou J L, Su H Y, Chen L Y, Liao Y P, Hartman-Frey C, Lai Y H, et al. Promoter hypermethylation of FBXO32, a novel TGF-beta/SMAD4 target gene and tumor suppressor, is associated with poor prognosis in human ovarian cancer. Lab Invest 2010; 90:414-25.

(41) Nelson J D, Denisenko O, Bomsztyk K. Protocol for the fast chromatin immunoprecipitation (ChIP) method. Nat Protoc 2006; 1:179-85.

The invention claimed is:

1. A compound having formula (IA)

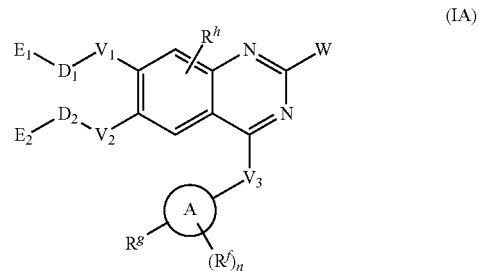

or a pharmaceutically acceptable salt thereof;
wherein W is

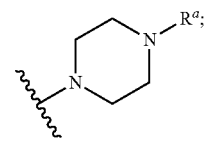

$R^a$ is selected from the group consisting of hydrogen, $C_{1-8}$ alkyl, and pyridyl;

either $V_1$ and $D_1$ are both absent and $E_1$ is hydrogen; or $V_1$ is O;

$D_1$ is absent or $C_{1-8}$ alkylene;

$E_1$ is selected from the group consisting of hydrogen and 6-membered carbocyclyl;

either $V_2$ and $D_2$ are both absent and $E_2$ is hydrogen; or $V_2$ is O;

$D_2$ is absent or $C_{1-8}$ alkylene;

$E_2$ is selected from the group consisting of hydrogen and 6-membered carbocyclyl;

$V_3$ is $NR^e$;

$R^e$ is hydrogen;

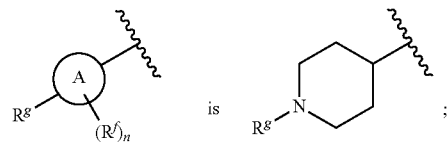

n is 0;

$R^g$ is selected from the group consisting of hydrogen and optionally substituted 5 to 10-membered carbocyclyl-$C_{1-6}$ alkyl, said carbocyclyl being optionally substituted with up to 3 $C_{1-4}$ alkyl groups optionally substituted with up to 3 halogens; and $R^h$ is absent.

2. A compound as claimed in claim 1, wherein $R^a$ is selected from the group consisting of $C_{1-6}$ alkyl, and pyridyl.

3. A compound as claimed in claim 1, wherein $V_1$ is O; $D_1$ is $C_{1-6}$ alkylene; and $E_1$ is hydrogen or 6-membered aryl.

4. A compound as claimed in claim 1, wherein $R^g$ is selected from the group consisting of hydrogen and optionally substituted 6 to 10-membered aryl-$C_{1-2}$ alkyl, said aryl being optionally substituted with up to 3 $C_{1-4}$ alkyl groups optionally substituted by up to three halogens.

5. A composition comprising a compound as claimed in claim 1 and a pharmaceutically acceptable excipient.

6. A compound which is any one of the following compounds, or a pharmaceutically acceptable salt thereof:

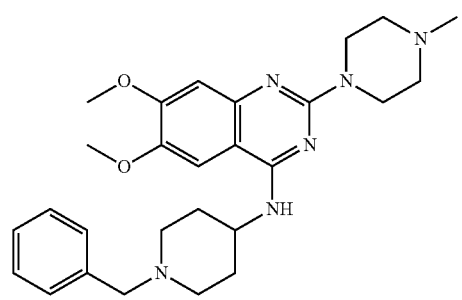

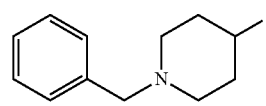

or

7. A compound which is any one of the following compounds, or a pharmaceutically acceptable salt thereof:

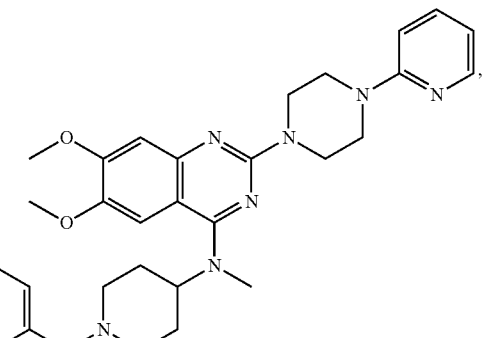

-continued

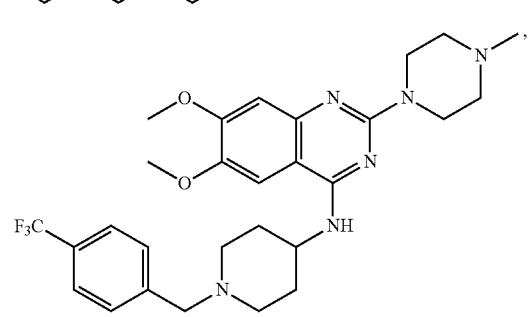

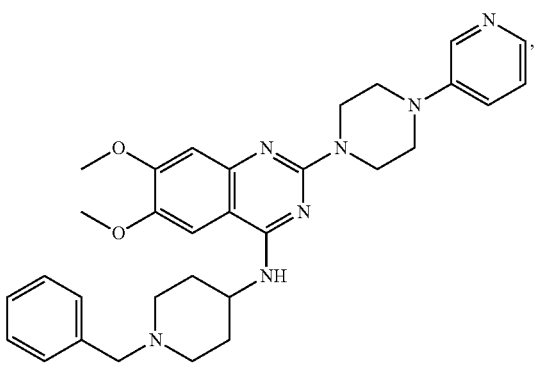

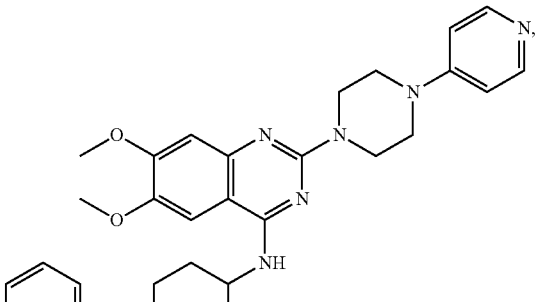

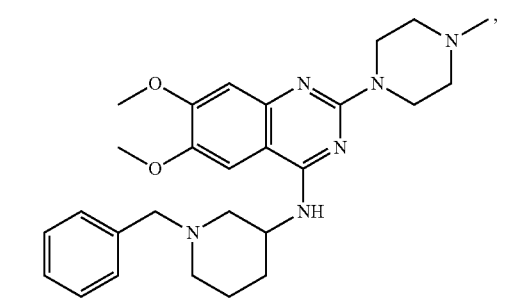

109
-continued
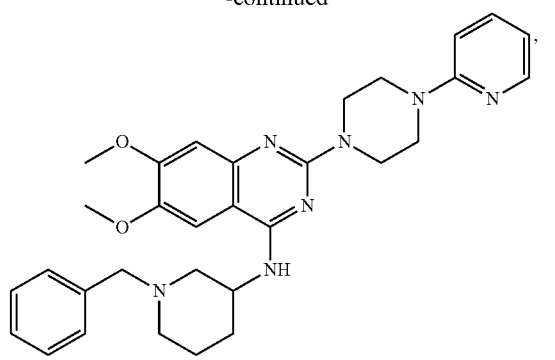
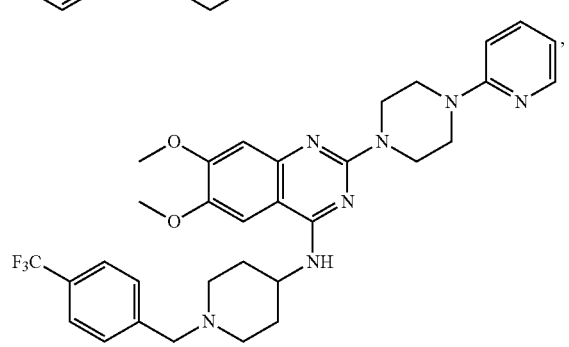
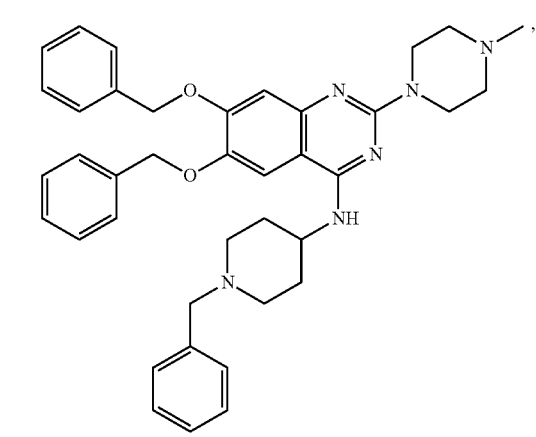
110
-continued
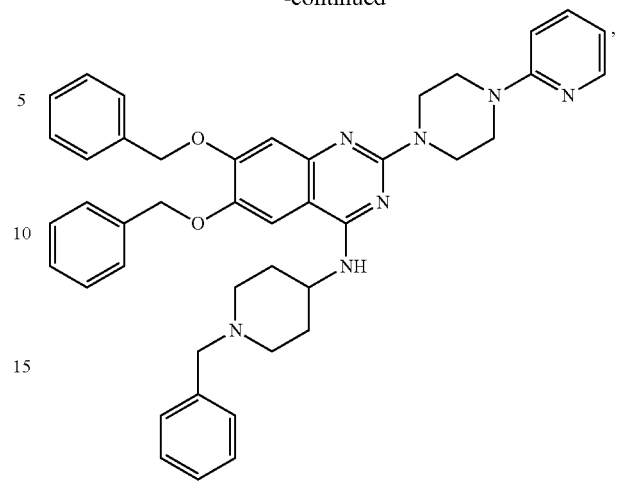
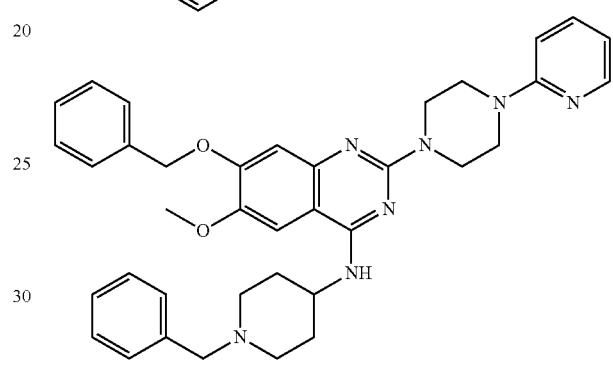
and
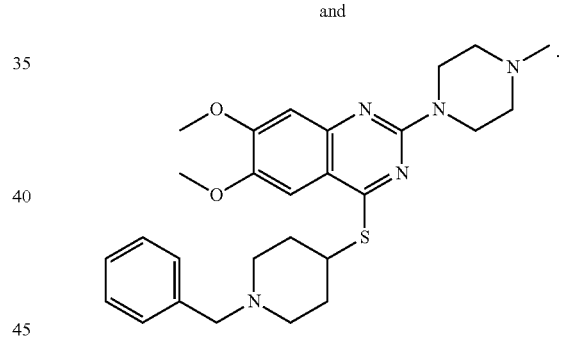
* * * * *